United States Patent
Tzvieli et al.

(10) Patent No.: US 10,064,559 B2
(45) Date of Patent: Sep. 4, 2018

(54) IDENTIFICATION OF THE DOMINANT NOSTRIL USING THERMAL MEASUREMENTS

(71) Applicant: Facense Ltd., Kiryat Tivon (IL)

(72) Inventors: Arie Tzvieli, Berkeley, CA (US); Gil Thieberger, Kiryat Tivon (IL); Ari M Frank, Haifa (IL)

(73) Assignee: Facense Ltd., Kiryat Tivon (IL)

( * ) Notice: Subject to any disclaimer, the term of this patent is extended or adjusted under 35 U.S.C. 154(b) by 0 days.

(21) Appl. No.: 15/832,879

(22) Filed: Dec. 6, 2017

(65) Prior Publication Data

US 2018/0092547 A1 Apr. 5, 2018

Related U.S. Application Data

(63) Continuation-in-part of application No. 15/722,434, filed on Oct. 2, 2017, and a continuation-in-part of
(Continued)

(51) Int. Cl.
*A61B 7/04* (2006.01)
*A61B 5/01* (2006.01)
(Continued)

(52) U.S. Cl.
CPC ............ *A61B 5/015* (2013.01); *A61B 5/0075* (2013.01); *A61B 5/0816* (2013.01);
(Continued)

(58) Field of Classification Search
CPC ..... A61B 5/015; A61B 5/0878; A61B 5/1118; A61B 5/6801; A61B 5/6847;
(Continued)

(56) References Cited

U.S. PATENT DOCUMENTS 5,143,086 A 9/1992 Duret et al.
5,664,578 A 9/1997 Boczan
(Continued)

FOREIGN PATENT DOCUMENTS

EP 2233071 A1 9/2013
WO WO2016025323 2/2016

OTHER PUBLICATIONS

Alghoul, K., Alharthi, S., Al Osman, H., & El Saddik, A. (2017). Heart Rate Variability extraction from videos signals: ICA vs. EVM comparison. IEEE Access, 5, 4711-4719.
(Continued)

*Primary Examiner* — David Porta
*Assistant Examiner* — Faye Boosalis
(74) *Attorney, Agent, or Firm* — Active Knowledge Ltd.

(57) ABSTRACT

Brain activity, and in particular which hemisphere is relatively more effective, is correlated with the dominant nostril (i.e., the nostril through which most of the air is exhaled when breathing through the nose). Thus, identifying which of the nostrils is dominant may have various applications. Described herein are systems and methods for identifying the dominant nostril. In one embodiment, a system includes at least one inward-facing head-mounted thermal camera (CAM) and a computer. The at least one CAM does not occlude any of the user's mouth and nostrils and is used to take thermal measurements of first and second regions below the right and left nostrils ($TH_{ROI1}$ and $TH_{ROI2}$, respectively). The computer identifies the dominant nostril based on $TH_{ROI1}$ and $TH_{ROI2}$. Optionally, the computer detects, utilizing $TH_{ROI1}$ and $TH_{ROI2}$, the three-dimensional (3D) shape of the exhale stream from at least one of the nostrils.

20 Claims, 18 Drawing Sheets

Head-mounted
thermal camera(s)
750

Related U.S. Application Data application No. 15/182,592, filed on Jun. 14, 2016, said application No. 15/722,434 is a continuation-in-part of application No. 15/231,276, filed on Aug. 8, 2016, said application No. 15/722,434 is a continuation-in-part of application No. 15/284,528, filed on Oct. 3, 2016, application No. 15/832,879, which is a continuation-in-part of application No. 15/635,178, filed on Jun. 27, 2017, application No. 15/832,879, which is a continuation-in-part of application No. 15/284,528, filed on Oct. 3, 2016, and a continuation-in-part of application No. 15/231,276, filed on Aug. 8, 2016, and a continuation-in-part of application No. 15/182,592, filed on Jun. 14, 2016, and a continuation-in-part of application No. 15/182,566, filed on Jun. 14, 2016, now Pat. No. 9,867,546.

(60) Provisional application No. 62/566,572, filed on Oct. 2, 2017, provisional application No. 62/408,677, filed on Oct. 14, 2016, provisional application No. 62/456,105, filed on Feb. 7, 2017, provisional application No. 62/480,496, filed on Apr. 2, 2017, provisional application No. 62/175,319, filed on Jun. 14, 2015, provisional application No. 62/202,808, filed on Aug. 8, 2015, provisional application No. 62/236,868, filed on Oct. 3, 2015, provisional application No. 62/354,833, filed on Jun. 27, 2016, provisional application No. 62/372,063, filed on Aug. 8, 2016.

(51) Int. Cl.
| | | |
|---|---|---|
| *A61B 5/08* | (2006.01) | |
| *A61B 5/093* | (2006.01) | |
| *A61B 7/00* | (2006.01) | |
| *A61B 5/16* | (2006.01) | |
| *G09B 19/00* | (2006.01) | |
| *G06N 99/00* | (2010.01) | |
| *G06T 7/00* | (2017.01) | |
| *G06K 9/00* | (2006.01) | |
| *G06K 9/62* | (2006.01) | |
| *G06T 7/60* | (2017.01) | |
| *G01J 5/10* | (2006.01) | |
| *A61B 5/00* | (2006.01) | |
| *H04N 5/232* | (2006.01) | |
| *H04N 5/33* | (2006.01) | |
| *G01J 5/00* | (2006.01) | |

(52) U.S. Cl.
CPC ............ *A61B 5/0935* (2013.01); *A61B 5/165* (2013.01); *A61B 5/168* (2013.01); *A61B 5/6803* (2013.01); *A61B 5/6814* (2013.01); *A61B 5/7267* (2013.01); *A61B 7/00* (2013.01); *A61B 7/003* (2013.01); *A61B 7/04* (2013.01); *G01J 5/0014* (2013.01); *G01J 5/0025* (2013.01); *G01J 5/10* (2013.01); *G06K 9/00255* (2013.01); *G06K 9/00281* (2013.01); *G06K 9/6202* (2013.01); *G06K 9/6256* (2013.01); *G06K 9/6267* (2013.01); *G06N 99/005* (2013.01); *G06T 7/0014* (2013.01); *G06T 7/60* (2013.01); *G09B 19/00* (2013.01); *H04N 5/23219* (2013.01); *H04N 5/33* (2013.01); *A61B 5/0077* (2013.01); *A61B 2562/0271* (2013.01); *G01J 2005/0077* (2013.01); *G06T 2207/30201* (2013.01)

(58) Field of Classification Search
CPC ...... A61B 5/6803; G02C 11/00; G02C 11/04; G02C 2200/16; G02C 5/14; G02C 7/02; A61F 9/04
See application file for complete search history.

(56) References Cited

U.S. PATENT DOCUMENTS

| | | |
|---|---|---|
| 6,121,953 A | 9/2000 | Walker |
| 6,286,958 B1 | 9/2001 | Koest et al. |
| 6,771,423 B2 | 8/2004 | Geist |
| 6,837,615 B2 | 1/2005 | Newman |
| 6,996,256 B2 | 2/2006 | Pavlidis |
| 7,027,621 B1 | 4/2006 | Prokoski |
| 7,135,980 B2 | 11/2006 | Moore et al. |
| 7,138,905 B2 | 11/2006 | Pavlidis et al. |
| 8,149,273 B2 | 4/2012 | Liu et al. |
| 8,289,443 B2 | 10/2012 | MacKenzie |
| 8,334,872 B2 | 12/2012 | Epps et al. |
| 8,360,986 B2 | 1/2013 | Farag et al. |
| 8,573,866 B2 | 11/2013 | Bond et al. |
| 8,585,588 B2 | 11/2013 | Kovarik et al. |
| 8,723,790 B1 | 5/2014 | Schaefer |
| 8,768,438 B2 | 7/2014 | Mestha et al. |
| 8,786,698 B2 | 7/2014 | Chen et al. |
| 8,855,384 B2 | 10/2014 | Kyal et al. |
| 8,964,298 B2 | 2/2015 | Haddick et al. |
| 9,019,174 B2 | 4/2015 | Jerauld |
| 9,020,185 B2 | 4/2015 | Mestha et al. |
| 9,194,749 B2 | 11/2015 | Pompei |
| 9,211,069 B2 | 12/2015 | Larsen et al. |
| 9,410,854 B2 | 8/2016 | Padiy |
| 9,569,734 B2 | 2/2017 | Thieberger et al. |
| 2002/0080094 A1 | 6/2002 | Biocca et al. |
| 2005/0083248 A1 | 4/2005 | Biocca et al. |
| 2005/0271117 A1 | 12/2005 | Grassl et al. |
| 2007/0047768 A1 | 3/2007 | Gordon et al. |
| 2007/0248238 A1 | 10/2007 | Abreu |
| 2007/0265507 A1 | 11/2007 | de Lemos |
| 2008/0260212 A1 | 10/2008 | Moskal et al. |
| 2009/0221888 A1 | 9/2009 | Wijesiriwardana |
| 2009/0237564 A1 | 9/2009 | Kikinis et al. |
| 2010/0191124 A1 | 7/2010 | Prokoski |
| 2010/0280334 A1 | 11/2010 | Carlson et al. |
| 2012/0062719 A1 | 3/2012 | Debevec et al. |
| 2012/0105473 A1 | 5/2012 | Bar-Zeev et al. |
| 2012/0197093 A1 | 8/2012 | LeBoeuf et al. |
| 2012/0327194 A1 | 12/2012 | Shiratori et al. |
| 2013/0124039 A1 | 5/2013 | Abreu |
| 2013/0215244 A1 | 8/2013 | Mestha et al. |
| 2013/0241805 A1 | 9/2013 | Gomez |
| 2013/0257709 A1 | 10/2013 | Raffle et al. |
| 2014/0180449 A1 | 6/2014 | Sung |
| 2014/0282911 A1 | 9/2014 | Bare et al. |
| 2014/0347265 A1 | 11/2014 | Aimone et al. |
| 2014/0366049 A1 | 12/2014 | Lehtiniemi et al. |
| 2015/0087924 A1 | 3/2015 | Li et al. |
| 2015/0148618 A1 | 5/2015 | Sitko et al. |
| 2015/0157255 A1 | 6/2015 | Nduka |
| 2015/0297126 A1 | 10/2015 | Atsumori et al. |
| 2015/0310263 A1 | 10/2015 | Zhang et al. |
| 2015/0359443 A1 | 12/2015 | Poh |
| 2016/0015289 A1 | 1/2016 | Simon et al. |
| 2016/0081622 A1 | 3/2016 | Abreu |
| 2016/0091877 A1 | 3/2016 | Fullam et al. |
| 2016/0098592 A1 | 4/2016 | Lee et al. |
| 2016/0100790 A1 | 4/2016 | Cantu et al. |
| 2016/0170996 A1 | 6/2016 | Frank et al. |
| 2016/0216760 A1 | 7/2016 | Trutna et al. |
| 2016/0224803 A1 | 8/2016 | Frank et al. |
| 2016/0235324 A1 | 8/2016 | Mershin et al. |
| 2016/0270656 A1 | 9/2016 | Samec et al. |
| 2016/0342835 A1 | 11/2016 | Kaehler |
| 2017/0007167 A1 | 1/2017 | Kostic et al. |

(56) References Cited

U.S. PATENT DOCUMENTS

2017/0231490 A1  8/2017  Toth et al.
2017/0235931 A1  8/2017  Publicover et al.

OTHER PUBLICATIONS

Al-Khalidi, F. Q., Saatchi, R., Burke, D., Elphick, H., & Tan, S. (2011). Respiration rate monitoring methods: A review. Pediatric pulmonology, 46(6), 523-529.

Appel, V. C., Belini, V. L., Jong, D. H., Magalhães, D. V., & Caurin, G. A. (Aug. 2014). Classifying emotions in rehabilitation robotics based on facial skin temperature. In Biomedical Robotics and Biomechatronics (2014 5th IEEE RAS & EMBS International Conference on (pp. 276-280). IEEE.

Aryal, A., Ghahramani, A., & Becerik-Gerber, B. (2017). Monitoring fatigue in construction workers using physiological measurements. Automation in Construction.

Boccanfuso, L., & O'Kane, J. M. (Jun. 2012). Remote measurement of breathing rate in real time using a high precision, single-point infrared temperature sensor. In Biomedical Robotics and Biomechatronics (BioRob), 2012 4th IEEE RAS & EMBS International Conference on (pp. 1704-1709). IEEE.

Cardone, D., Pinti, P., & Merla, A. (2015). Thermal infrared imaging-based computational psychophysiology for psychometrics. Computational and mathematical methods in medicine, 2015.

Carine Collé, Re-Experience Big-Data, 3 months group project with Sanya Rai Gupta and Florian Puech, UK, London, RCA, IDE, 2014, Amoeba.

Choi, J. S., Bang, J. W., Heo, H., & Park, K. R. (2015). Evaluation of Fear Using Nonintrusive Measurement of Multimodal Sensors. Sensors, 15(7), 17507-17533.

Clay-Warner, J., & Robinson, D. T. (2015). Infrared thermography as a measure of emotion response. Emotion Review, 7(2), 157-162.

Cross, C. B., Skipper, J. A., & Petkie, D. (May 2013). Thermal imaging to detect physiological indicators of stress in humans. In SPIE Defense, Security, and Sensing (pp. 87050I-87050I). International Society for Optics and Photonics.

Fei, J., & Pavlidis, I. (Aug. 2006). Analysis of breathing air flow patterns in thermal imaging. In Engineering in Medicine and Biology Society, 2006. EMBS'06. 28th Annual International Conference of the IEEE (pp. 946-952). IEEE.

Fei, J., & Pavlidis, I. (2010). Thermistor at a distance: unobtrusive measurement of breathing. IEEE Transactions on Biomedical Engineering, 57(4), 988-998.

Fernández-Cuevas, I., Marins, J. C. B., Lastras, J. A., Carmona, P. M. G., Cano, S. P., García-Concepción, M. Á., & Sillero-Quintana, M. (2015). Classification of factors influencing the use of infrared thermography in humans: A review. Infrared Physics & Technology, 71, 28-55.

Ghahramani, A., Castro, G., Becerik-Gerber, B., & Yu, X. (2016). Infrared thermography of human face for monitoring thermoregulation performance and estimating personal thermal comfort. Building and Environment, 109, 1-11.

Hawkes, P. W. (2012). Advances in Imaging and Electron Physics (vol. 171). Academic Press. Chapter 2.

Hong, K., Yuen, P., Chen, T., Tsitiridis, A., Kam, F., Jackman, J., . . . & Lightman+, F. T. S. (Sep. 2009). Detection and classification of stress using thermal imaging technique. In Proc. of SPIE Vol (vol. 7486, pp. 74860I-1).

Ioannou, S., Gallese, V., & Merla, A. (2014). Thermal infrared imaging in psychophysiology: potentialities and limits. Psychophysiology, 51(10), 951-963.

Jenkins, S. D., & Brown, R. D. H. (2014). A correlational analysis of human cognitive activity using Infrared Thermography of the supraorbital region, frontal EEG and self-report of core affective state. QIRT.

Johnson, M. L., Price, P. A., & Jovanov, E. (Aug. 2007). A new method for the quantification of breathing. In Engineering in Medicine and Biology Society, 2007. EMBS 2007. 29th Annual International Conference of the IEEE (pp. 4568-4571). IEEE.

Jovanov, E., Raskovic, D., & Hormigo, R. (2001). Thermistor-based breathing sensor for circadian rhythm evaluation. Biomedical sciences instrumentation, 37, 493-498.

Joyal, C. C., & Henry, M. (2013). Long-wave infrared functional brain imaging in human: a pilot study. The open neuroimaging journal, 7(1).

Kimura, S., Fukuomoto, M., & Horikoshi, T. (Sep. 2013). Eyeglass-based hands-free videophone. In Proceedings of the 2013 International Symposium on Wearable Computers (pp. 117-124). ACM.

Kurz, M., Hölzl, G., Riener, A., Anzengruber, B., Schmittner, T., & Ferscha, A. (Sep. 2012). Are you cool enough for Texas Hold'Em Poker?. In Proceedings of the 2012 ACM Conference on Ubiquitous Computing (pp. 1145-1149). ACM.

Lewis, G. F., Gatto, R. G., & Porges, S. W. (2011). A novel method for extracting respiration rate and relative tidal volume from infrared thermography. Psychophysiology, 48(7), 877-887.

Merla, A. (2014). Thermal expression of intersubjectivity offers new possibilities to human-machine and technologically mediated interactions.

Mizuno, T., & Kume, Y. (Aug. 2015). Development of a Glasses-Like Wearable Device to Measure Nasal Skin Temperature. In International Conference on Human-Computer Interaction (pp. 727-732). Springer International Publishing.

Mizuno, T., Sakai, T., Kawazura, S., Asano, H., Akehi, K., Matsuno, S., . . . & Itakura, N. (Jul. 2015). Facial Skin Temperature Fluctuation by Mental Work-Load with Thermography. In The International Conference on Electronics and Software Science (ICESS2015) Proceedings (pp. 212-215).

Murthy, R., & Pavlidis, I. (2006). Noncontact measurement of breathing function. IEEE Engineering in Medicine and Biology Magazine, 25(3), 57-67.

Murthy, R., Pavlidis, I., & Tsiamyrtzis, P. (Sep. 2004). Touchless monitoring of breathing function. In Engineering in Medicine and Biology Society, 2004. IEMBS'04. 26th Annual International Conference of the IEEE (vol. 1, pp. 1196-1199). IEEE.

Nagaraj, S., Quoraishee, S., Chan, G., & Short, K. R. (Apr. 2010). Biometric study using hyperspectral imaging during stress. In SPIE Defense, Security, and Sensing (pp. 76740K-76740K). International Society for Optics and Photonics.

Nhan, B. R., & Chau, T. (2010). Classifying affective states using thermal infrared imaging of the human face. IEEE Transactions on Biomedical Engineering, 57(4), 979-987.

Pavlidis, I., & Levine, J. (2002). Thermal image analysis for polygraph testing. IEEE Engineering in Medicine and Biology Magazine, 21(6), 56-64.

Pavlidis, I., Dowdall, J., Sun, N., Puri, C., Fei, J., & Garbey, M. (2007). Interacting with human physiology. Computer Vision and Image Understanding, 108(1), 150-170.

Puri, C., Olson, L., Pavlidis, I., Levine, J., & Starren, J. (Apr. 2005). StressCam: non-contact measurement of users' emotional states through thermal imaging. In CHI'05 extended abstracts on Human factors in computing systems (pp. 1725-1728). ACM.

Rajoub, B. A., & Zwiggelaar, R. (2014). Thermal facial analysis for deception detection. IEEE transactions on information forensics and security, 9(6), 1015-1023.

Ramirez, G. A., Fuentes, O., Crites Jr, S. L., Jimenez, M., & Ordonez, J. (2014). Color analysis of facial skin: Detection of emotional state. In Proceedings of the IEEE Conference on Computer Vision and Pattern Recognition Workshops (pp. 468-473).

Romera-Paredes, B., Zhang, C., & Zhang, Z. (Jul. 2014). Facial expression tracking from head-mounted, partially observing cameras. In Multimedia and Expo (ICME), 2014 IEEE International Conference on (pp. 1-6). IEEE.

Sharma, N., Dhall, A., Gedeon, T., & Goecke, R. (Sep. 2013). Modeling stress using thermal facial patterns: A spatio-temporal approach. In Affective Computing and Intelligent Interaction (ACII), 2013 Humaine Association Conference on (pp. 387-392). IEEE.

Sharma, N., Dhall, A., Gedeon, T., & Goecke, R. (2014). Thermal spatio-temporal data for stress recognition. EURASIP Journal on Image and Video Processing, 2014(1), 28.

(56) References Cited

OTHER PUBLICATIONS

Shastri, D., Papadakis, M., Tsiamyrtzis, P., Bass, B., & Pavlidis, I. (2012). Perinasal imaging of physiological stress and its affective potential. IEEE Transactions on Affective Computing, 3(3), 366-378.

Tsiamyrtzis, P., Dowdall, J., Shastri, D., Pavlidis, I. T., Frank, M. G., & Ekman, P. (2007). Imaging facial physiology for the detection of deceit. International Journal of Computer Vision, 71(2), 197-214.

Yang, M., Liu, Q., Turner, T., & Wu, Y. (Jun. 2008). Vital sign estimation from passive thermal video. In Computer Vision and Pattern Recognition, 2008. CVPR 2008. IEEE Conference on (pp. 1-8). IEEE.

Written opinion of the international searching authority, PCT/IB2017/056066, dated Jan. 29, 2018.

Written opinion of the international searching authority, PCT/IB2017/056067, dated Jan. 29, 2018.

Written opinion of the international searching authority, PCT/IB2017/056069, dated Jan. 29, 2018.

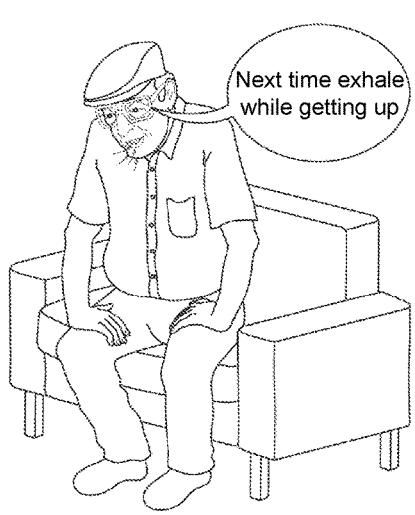
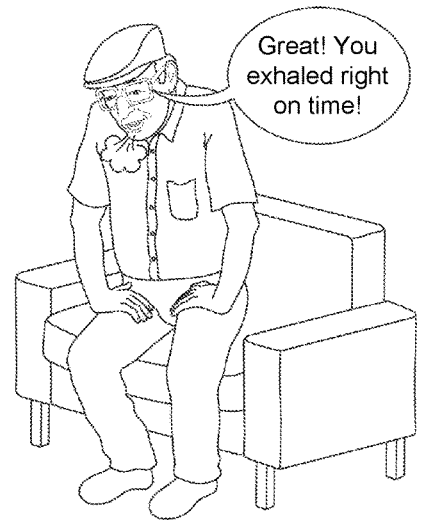
FIG. 24a  FIG. 24b
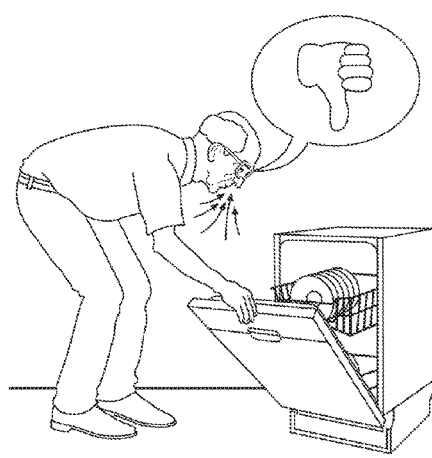
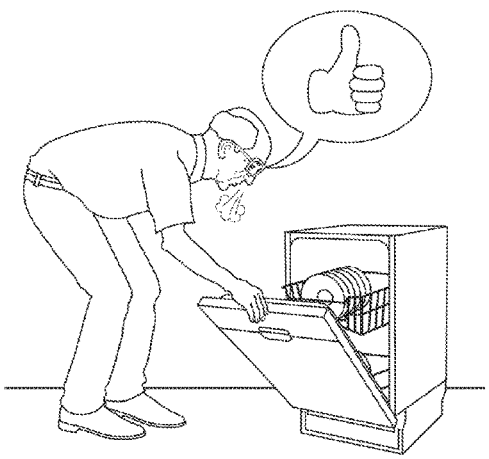
FIG. 25a  FIG. 25b
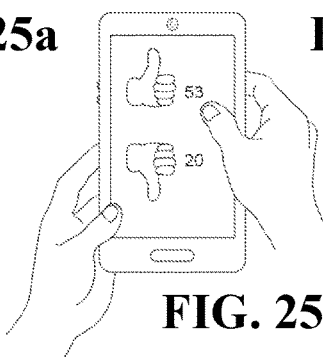
FIG. 25c

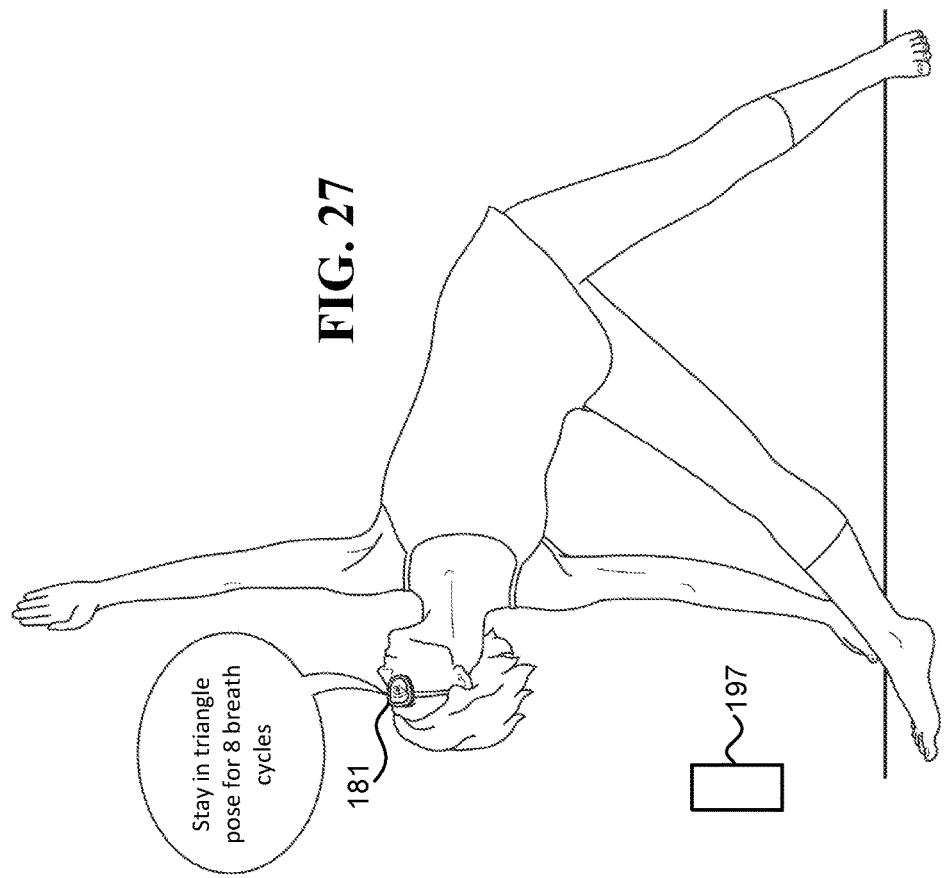
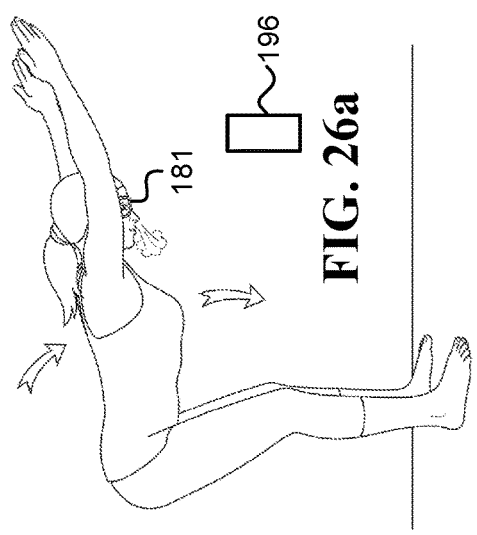
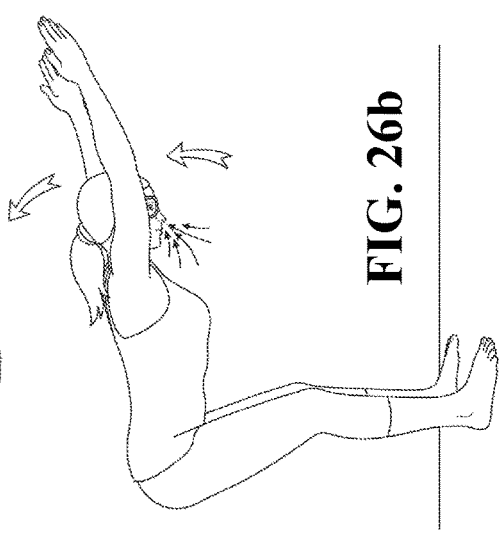

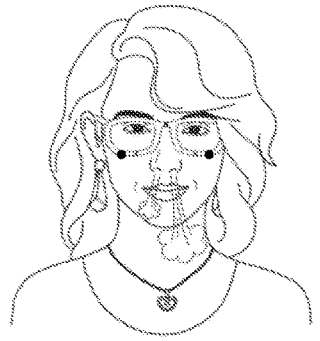 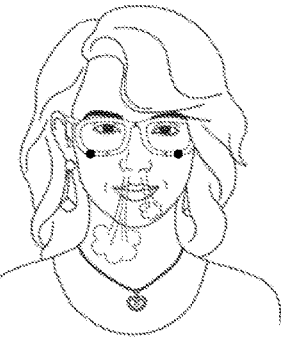 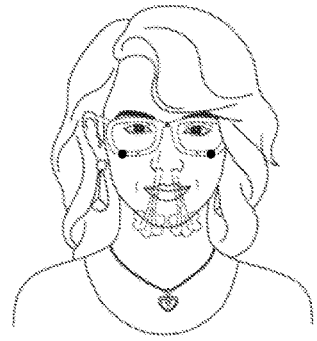
FIG. 32a   FIG. 32b   FIG. 32c
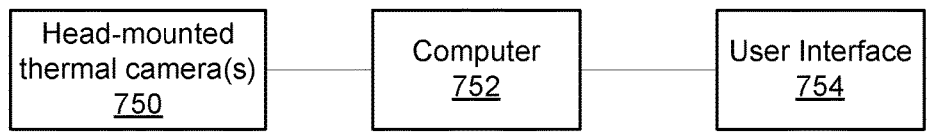
FIG. 33
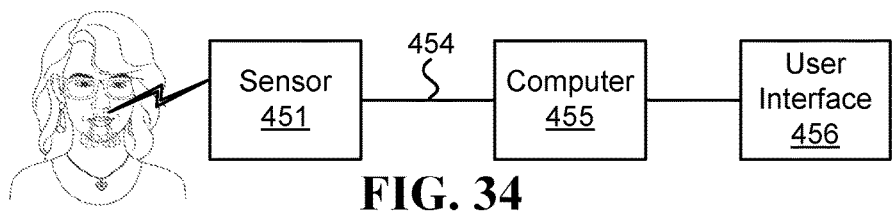
FIG. 34
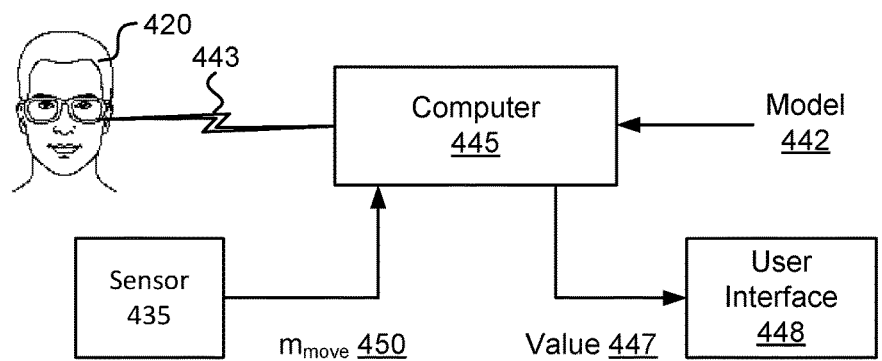
FIG. 35

IDENTIFICATION OF THE DOMINANT NOSTRIL USING THERMAL MEASUREMENTS

CROSS-REFERENCE TO RELATED APPLICATIONS

This application claims priority to U.S. Provisional Patent Application No. 62/456,105, filed Feb. 7, 2017, and U.S. Provisional Patent Application No. 62/480,496, filed Apr. 2, 2017, and U.S. Provisional Patent Application No. 62/566,572, filed Oct. 2, 2017. U.S. Provisional Patent Application No. 62/566,572 is herein incorporated by reference in its entirety.

This application is a Continuation-In-Part of U.S. application Ser. No. 15/182,566, filed Jun. 14, 2016, now U.S. Pat. No. [TBD], which claims priority to U.S. Provisional Patent Application No. 62/175,319, filed Jun. 14, 2015, and U.S. Provisional Patent Application No. 62/202,808, filed Aug. 8, 2015.

This application is also a Continuation-In-Part of U.S. application Ser. No. 15/182,592, filed Jun. 14, 2016, which claims priority to U.S. Provisional Patent Application No. 62/175,319, filed Jun. 14, 2015, and U.S. Provisional Patent Application No. 62/202,808, filed Aug. 8, 2015.

This application is also a Continuation-In-Part of U.S. application Ser. No. 15/231,276, filed Aug. 8, 2016, which claims priority to U.S. Provisional Patent Application No. 62/202,808, filed Aug. 8, 2015, and U.S. Provisional Patent Application No. 62/236,868, filed Oct. 3, 2015.

This application is also a Continuation-In-Part of U.S. application Ser. No. 15/284,528, filed Oct. 3, 2016, which claims priority to U.S. Provisional Patent Application No. 62/236,868, filed Oct. 3, 2015, and U.S. Provisional Patent Application No. 62/354,833, filed Jun. 27, 2016, and U.S. Provisional Patent Application No. 62/372,063, filed Aug. 8, 2016.

This application is also a Continuation-In-Part of U.S. application Ser. No. 15/635,178, filed Jun. 27, 2017, which claims priority to U.S. Provisional Patent Application No. 62/354,833, filed Jun. 27, 2016, and U.S. Provisional Patent Application No. 62/372,063, filed Aug. 8, 2016.

This application is also a Continuation-In-Part of U.S. application Ser. No. 15/722,434, filed Oct. 2, 2017, which claims priority to U.S. Provisional Patent Application No. 62/408,677, filed Oct. 14, 2016, and U.S. Provisional Patent Application No. 62/456,105, filed Feb. 7, 2017, and U.S. Provisional Patent Application No. 62/480,496, filed Apr. 2, 2017. U.S. Ser. No. 15/722,434 is also a Continuation-In-Part of U.S. application Ser. No. 15/182,592, filed Jun. 14, 2016, which claims priority to U.S. Provisional Patent Application No. 62/175,319, filed Jun. 14, 2015, and U.S. Provisional Patent Application No. 62/202,808, filed Aug. 8, 2015. U.S. Ser. No. 15/722,434 is also a Continuation-In-Part of U.S. application Ser. No. 15/231,276, filed Aug. 8, 2016, which claims priority to U.S. Provisional Patent Application No. 62/202,808, filed Aug. 8, 2015, and U.S. Provisional Patent Application No. 62/236,868, filed Oct. 3, 2015. And U.S. Ser. No. 15/722,434 is also a Continuation-In-Part of U.S. application Ser. No. 15/284,528, filed Oct. 3, 2016, which claims priority to U.S. Provisional Patent Application No. 62/236,868, filed Oct. 3, 2015, and U.S. Provisional Patent Application No. 62/354,833, filed Jun. 27, 2016, and U.S. Provisional Patent Application No. 62/372,063, filed Aug. 8, 2016.

This Application may include subject matter related to co-pending U.S. patent application Ser. No. 15/832,871 filed on Dec. 6, 2017.

ACKNOWLEDGMENTS

Gil Thieberger would like to thank his holy and beloved teacher, Lama Dvora-hla, for her extraordinary teachings and manifestation of wisdom, love, compassion and morality, and for her endless efforts, support, and skills in guiding him and others on their paths to freedom and ultimate happiness. Gil would also like to thank his beloved parents for raising him exactly as they did.

BACKGROUND

When a person breathes primarily through the nose (i.e., nasal breathing), one of the nostrils may be more dominant than the other nostril, with most of the exhaled air flowing through it. The right and the left nostrils may switch roles as the dominant nostril several times a day, and sometimes the breathing is essentially the same through both nostrils. Brain activity, and in particular, which hemisphere is relatively more effective, is correlated with the dominant nostril. When the left nostril is dominant, the right hemisphere ("right-brain") is typically more effective at performing certain activities associated with it, and when the right nostril is dominant, the left hemisphere ("left-brain") is typically more effective at performing certain activities associated with it.

Since each side of the brain plays a different role in different types of activities, it has long been believed by yoga practitioners that it is better to conduct certain activities when a certain nostril is dominant. For example, exercising, eating, digesting, and taking care of the body (e.g., defecating) are better done when the right nostril is dominant. Various forms of mental activity, such as planning, memorizing, writing, thinking, etc. are better done when the left nostril is dominant.

SUMMARY

A person's respiratory activity can be indicative of the person's emotional and/or physiological state. For example, the rate at which the user breathes can be indicative of whether the user is calm or stressed. While being aware of the breathing rate is something that can be achieved by most people with practice, it is more difficult to maintain awareness of other respiratory parameters that may also be indicative of a user's state. One example of such a type of respiratory parameter is the dominant nostril, which is the nostril through which most of the air is exhaled when breathing through the nose. Brain activity, and in particular, which hemisphere is relatively more effective, is correlated with the dominant nostril. Thus, it can be beneficial to know which nostril is dominant at a given time, e.g., in order to better choose when to partake in different activities that may involve different types of brain activity (e.g., "right-brain" vs. "left-brain" activities).

Some embodiments of this disclosure involve various systems that may be utilized to identify a user's dominant nostril. One approach for identifying the dominant nostril relies on taking thermal measurements of a user's face. In one embodiment, a system configured to identify the dominant nostril includes at least one inward-facing head-mounted thermal camera (denoted CAM) that takes thermal measurements of first and second regions below the right and left nostrils (denoted $TH_{ROI1}$ and $TH_{ROI2}$, respectively). The at least one CAM does not occlude any of the user's mouth and nostrils. Additionally, the system includes a computer that identifies the dominant nostril based on $TH_{ROI1}$ and $TH_{ROI2}$. Optionally, each CAM, from among the at least one CAM, is physically coupled to a frame worn on the user's head, weighs below 10 g, is located less than 15 cm from the user's face and above the user's upper lip, and comprises multiple sensing elements.

One aspect of this disclosure involves utilizing $TH_{ROI1}$ and $TH_{ROI2}$ to detect the shape of the exhale stream (denoted SHAPE). The SHAPE represents the three-dimensional (3D) shape of the exhale stream from at least one of the nostrils. The SHAPE changes during the day and may reflect the user's mental, physiological, and/or energetic state. Optionally, the SHAPE may be defined by the shape of a geometric body that confines the exhale stream from at least one of the nostrils. In one embodiment, the computer is further configured to identify the SHAPE based on $TH_{ROI1}$ and $TH_{ROI2}$, and to differentiate between at least first and second shapes of the exhale stream (SHAPEs).

BRIEF DESCRIPTION OF THE DRAWINGS

The embodiments are herein described by way of example only, with reference to the following drawings:

FIG. 24a, FIG. 24b, FIG. 25a, FIG. 25b and FIG. 25c illustrate how embodiments described herein may help train an elderly user to exhale during effort;

FIG. 26a and FIG. 26b illustrate a fitness app running on smartphone, which instructs the user to exhale while bending down, and to inhale while straightening up;

FIG. 27 illustrates a fitness app running on smartphone, which instructs the user to stay in a triangle pose for 8 breath cycles;

FIG. 32a is a schematic illustration of a left dominant nostril;

FIG. 32b is a schematic illustration of a right dominant nostril;

FIG. 32c is a schematic illustration of balanced breathing;

FIG. 33 is a schematic illustration of an embodiment of a system that identifies the dominant nostril;

FIG. 34 illustrates an embodiment of a system that suggests activities according to the dominant nostril;

FIG. 35 illustrates an embodiment of a system for calculating a respiratory parameter;

DETAILED DESCRIPTION

Figure 1A:
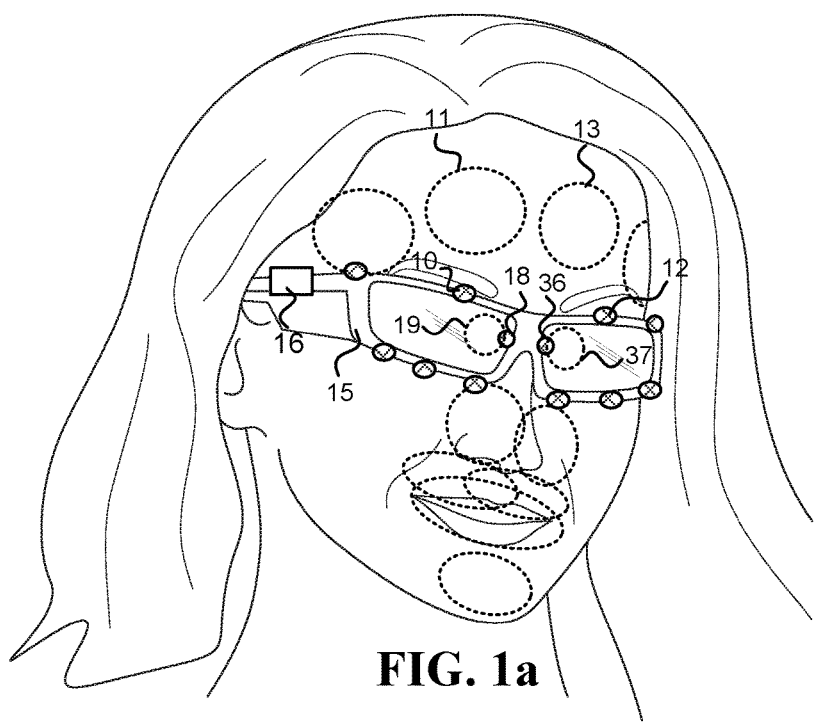
FIG. 1a and FIG. 1b illustrate various inward-facing head-mounted cameras coupled to an eyeglasses frame.

A "thermal camera" refers herein to a non-contact device that measures electromagnetic radiation having wavelengths longer than 2500 nanometer (nm) and does not touch its region of interest (ROI). A thermal camera may include one sensing element (pixel), or multiple sensing elements that are also referred to herein as "sensing pixels", "pixels", and/or focal-plane array (FPA). A thermal camera may be based on an uncooled thermal sensor, such as a thermopile sensor, a microbolometer sensor (where microbolometer refers to any type of a bolometer sensor and its equivalents), a pyroelectric sensor, or a ferroelectric sensor.

Sentences in the form of "thermal measurements of an ROI" (usually denoted $TH_{ROI}$ or some variant thereof) refer to at least one of: (i) temperature measurements of the ROI ($T_{ROI}$), such as when using thermopile or microbolometer sensors, and (ii) temperature change measurements of the ROI ($\Delta T_{ROI}$), such as when using a pyroelectric sensor or when deriving the temperature changes from temperature measurements taken at different times by a thermopile sensor or a microbolometer sensor.

In some embodiments, a device, such as a thermal camera, may be positioned such that it occludes an ROI on the user's face, while in other embodiments, the device may be positioned such that it does not occlude the ROI. Sentences in the form of "the system/camera does not occlude the ROI" indicate that the ROI can be observed by a third person located in front of the user and looking at the ROI, such as illustrated by all the ROIs in FIG. 7, FIG. 11 and FIG. 19. Sentences in the form of "the system/camera occludes the ROI" indicate that some of the ROIs cannot be observed directly by that third person, such as ROIs 19 and 37 that are occluded by the lenses in FIG. 1a, and ROIs 97 and 102 that are occluded by cameras 91 and 96, respectively, in FIG. 9.

Although many of the disclosed embodiments can use occluding thermal cameras successfully, in certain scenarios, such as when using an HMS on a daily basis and/or in a normal day-to-day setting, using thermal cameras that do not occlude their ROIs on the face may provide one or more advantages to the user, to the HMS, and/or to the thermal cameras, which may relate to one or more of the following: esthetics, better ventilation of the face, reduced weight, simplicity to wear, and reduced likelihood to being tarnished.

A "Visible-light camera" refers to a non-contact device designed to detect at least some of the visible spectrum, such as a camera with optical lenses and CMOS or CCD sensor.

The term "inward-facing head-mounted camera" refers to a camera configured to be worn on a user's head and to remain pointed at its ROI, which is on the user's face, also when the user's head makes angular and lateral movements (such as movements with an angular velocity above 0.1 rad/sec, above 0.5 rad/sec, and/or above 1 rad/sec). A head-mounted camera (which may be inward-facing and/or outward-facing) may be physically coupled to a frame worn on the user's head, may be attached to eyeglass using a clip-on mechanism (configured to be attached to and detached from the eyeglasses), or may be mounted to the user's head using any other known device that keeps the camera in a fixed position relative to the user's head also when the head moves. Sentences in the form of "camera physically coupled to the frame" mean that the camera moves with the frame, such as when the camera is fixed to (or integrated into) the frame, or when the camera is fixed to (or integrated into) an element that is physically coupled to the frame. The abbreviation "CAM" denotes "inward-facing head-mounted thermal camera", the abbreviation "$CAM_{out}$" denotes "outward-facing head-mounted thermal camera", the abbreviation "VCAM" denotes "inward-facing head-mounted visible-light camera", and the abbreviation "$VCAM_{out}$" denotes "outward-facing head-mounted visible-light camera".

Sentences in the form of "a frame configured to be worn on a user's head" or "a frame worn on a user's head" refer to a mechanical structure that loads more than 50% of its weight on the user's head. For example, an eyeglasses frame may include two temples connected to two rims connected by a bridge; the frame in Oculus Rift™ includes the foam placed on the user's face and the straps; and the frames in Google Glass™ and Spectacles by Snap Inc. are similar to eyeglasses frames. Additionally or alternatively, the frame may connect to, be affixed within, and/or be integrated with, a helmet (e.g., sports, motorcycle, bicycle, and/or combat helmets) and/or a brainwave-measuring headset.

When a thermal camera is inward-facing and head-mounted, challenges faced by systems known in the art that are used to acquire thermal measurements, which include non-head-mounted thermal cameras, may be simplified and even eliminated with some of the embodiments described herein. Some of these challenges may involve dealing with complications caused by movements of the user, image registration, ROI alignment, tracking based on hot spots or markers, and motion compensation in the IR domain.

In various embodiments, cameras are located close to a user's face, such as at most 2 cm, 5 cm, 10 cm, 15 cm, or 20 cm from the face (herein "cm" denotes to centimeters). The distance from the face/head in sentences such as "a camera located less than 15 cm from the face/head" refers to the shortest possible distance between the camera and the face/head. The head-mounted cameras used in various embodiments may be lightweight, such that each camera weighs below 10 g, 5 g, 1 g, and/or 0.5 g (herein "g" denotes to grams).

Figure 1B:
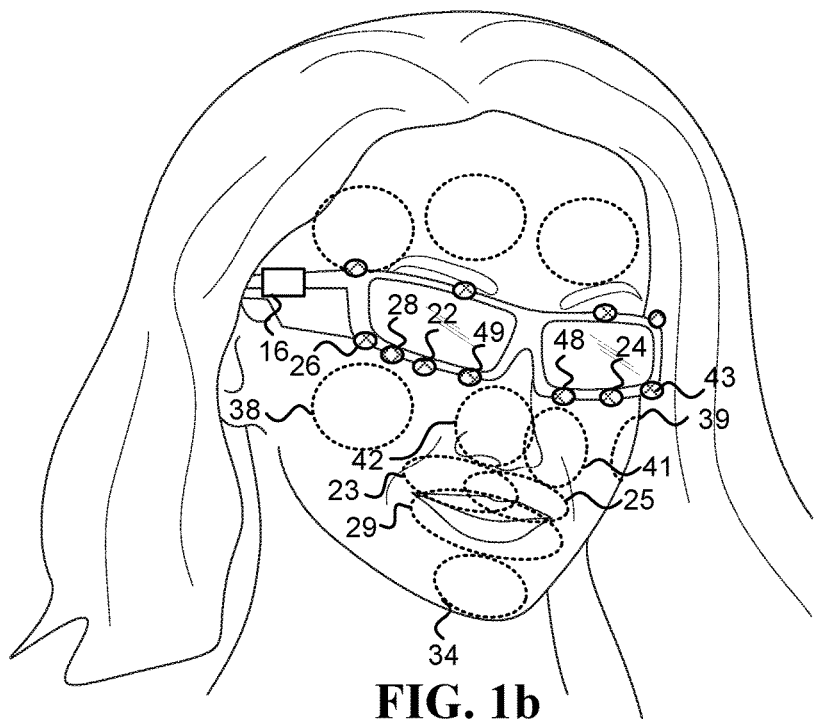

The following figures show various examples of HMSs equipped with head-mounted cameras. FIG. 1a illustrates various inward-facing head-mounted cameras coupled to an eyeglasses frame 15. Cameras 10 and 12 measure regions 11 and 13 on the forehead, respectively. Cameras 18 and 36 measure regions on the periorbital areas 19 and 37, respectively. The HMS further includes an optional computer 16, which may include a processor, memory, a battery and/or a communication module. FIG. 1b illustrates a similar HMS in which inward-facing head-mounted cameras 48 and 49 measure regions 41 and 41, respectively. Cameras 22 and 24 measure regions 23 and 25, respectively. Camera 28 measures region 29. And cameras 26 and 43 measure regions 38 and 39, respectively.

Figure 2:
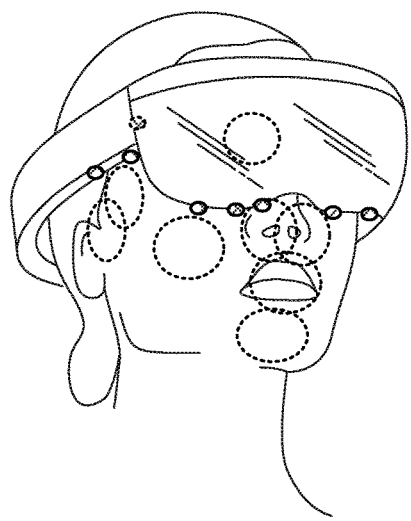
FIG. 2 illustrates inward-facing head-mounted cameras coupled to an augmented reality device.
Figure 3:
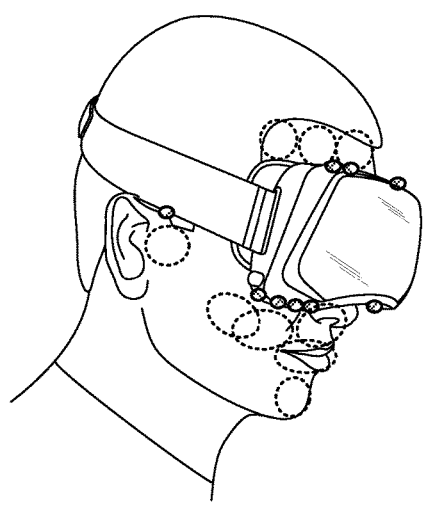
FIG. 3 illustrates head-mounted cameras coupled to a virtual reality device.
Figure 4:
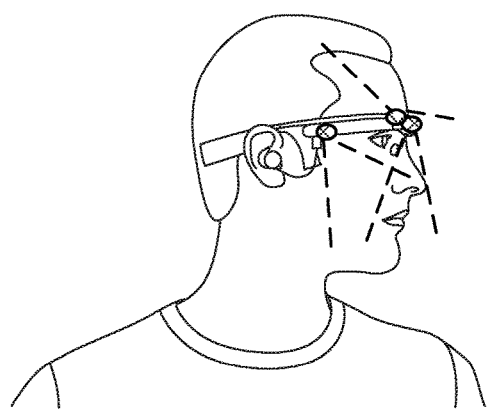
FIG. 4 illustrates a side view of head-mounted cameras coupled to an augmented reality device.
Figure 5:
FIG. 5 illustrates a side view of head-mounted cameras coupled to a sunglasses frame.

FIG. 2 illustrates inward-facing head-mounted cameras coupled to an augmented reality device such as Microsoft HoloLens™. FIG. 3 illustrates head-mounted cameras coupled to a virtual reality device such as Facebook's Oculus Rift™. FIG. 4 is a side view illustration of head-mounted cameras coupled to an augmented reality device such as Google Glass™. FIG. 5 is another side view illustration of head-mounted cameras coupled to a sunglasses frame.

Figures 6, 7:
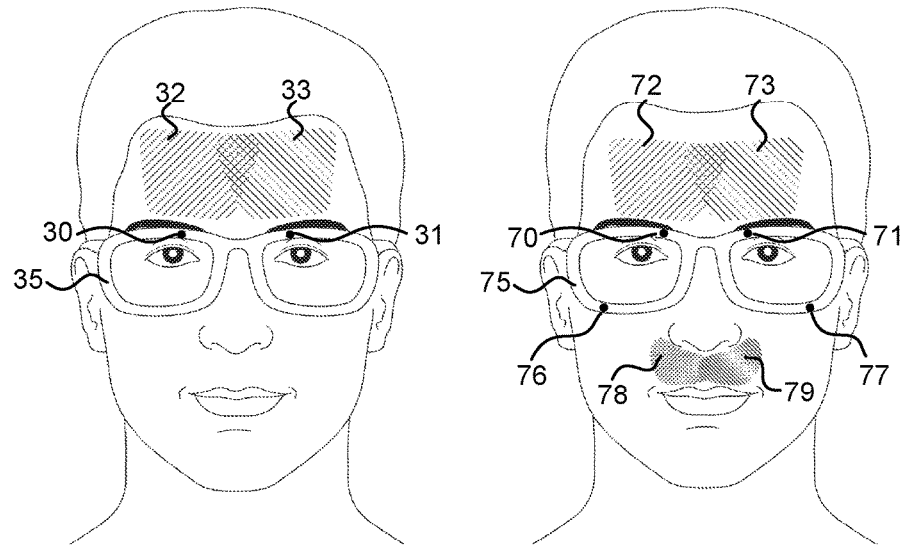
FIG. 6, FIG. 7, FIG. 8 and FIG. 9 illustrate head-mounted systems (HMSs) configured to measure various ROIs relevant to some of the embodiments describes herein.
Figures 8, 9:
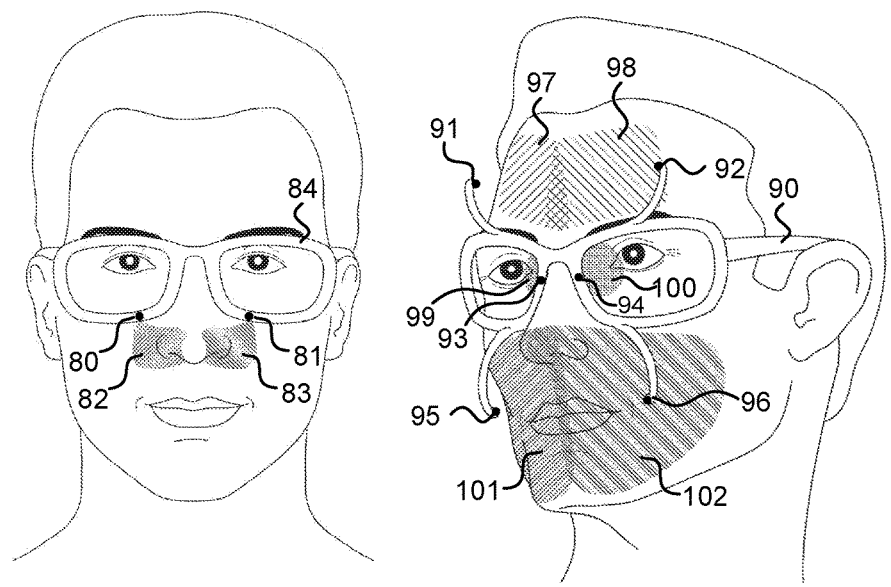

FIG. 6 to FIG. 9 illustrate HMSs configured to measure various ROIs relevant to some of the embodiments describes herein. FIG. 6 illustrates a frame 35 that mounts inward-facing head-mounted cameras 30 and 31 that measure regions 32 and 33 on the forehead, respectively. FIG. 7 illustrates a frame 75 that mounts inward-facing head-mounted cameras 70 and 71 that measure regions 72 and 73 on the forehead, respectively, and inward-facing head-mounted cameras 76 and 77 that measure regions 78 and 79 on the upper lip, respectively. FIG. 8 illustrates a frame 84 that mounts inward-facing head-mounted cameras 80 and 81 that measure regions 82 and 83 on the sides of the nose, respectively. And FIG. 9 illustrates a frame 90 that includes (i) inward-facing head-mounted cameras 91 and 92 that are mounted to protruding arms and measure regions 97 and 98 on the forehead, respectively, and (ii) inward-facing head-mounted cameras 95 and 96, which are also mounted to protruding arms, which measure regions 101 and 102 on the lower part of the face, respectively, and (iii) head-mounted cameras 93 and 94 that measure regions on the periorbital areas 99 and 100, respectively.

Figure 10:
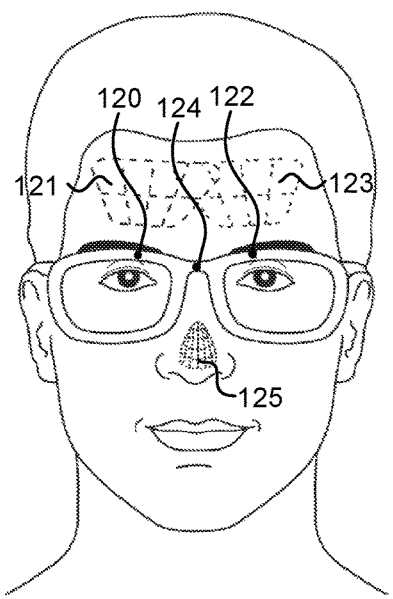
FIG. 10, FIG. 11, FIG. 12 and FIG. 13 illustrate various embodiments of systems that include inward-facing head-mounted cameras having multi-pixel sensors (FPA sensors)
Figure 11:
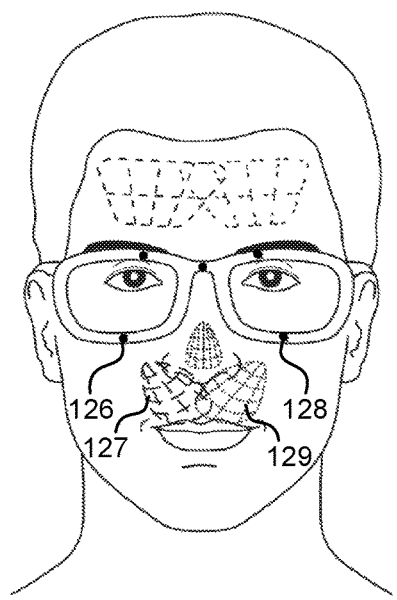
Figure 12:
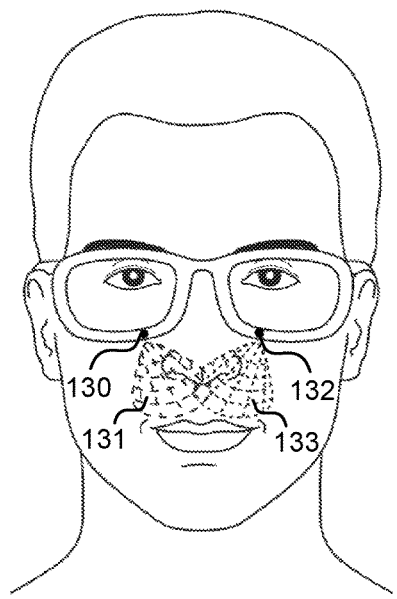
Figure 13:
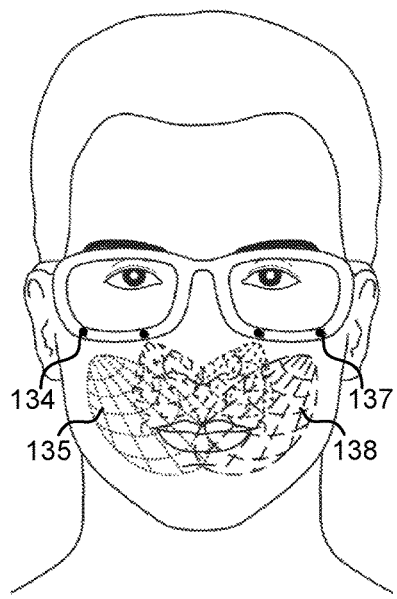

FIG. 10 to FIG. 13 illustrate various inward-facing head-mounted cameras having multi-pixel sensors (FPA sensors), configured to measure various ROIs relevant to some of the embodiments describes herein. FIG. 10 illustrates head-mounted cameras 120 and 122 that measure regions 121 and 123 on the forehead, respectively, and mounts head-mounted camera 124 that measure region 125 on the nose. FIG. 11 illustrates head-mounted cameras 126 and 128 that measure regions 127 and 129 on the upper lip, respectively, in addition to the head-mounted cameras already described in FIG. 10. FIG. 12 illustrates head-mounted cameras 130 and 132 that measure larger regions 131 and 133 on the upper lip and the sides of the nose, respectively. And FIG. 13 illustrates head-mounted cameras 134 and 137 that measure regions 135 and 138 on the right and left cheeks and right and left sides of the mouth, respectively, in addition to the head-mounted cameras already described in FIG. 12.

In some embodiments, the head-mounted cameras may be physically coupled to the frame using a clip-on device configured to be attached/detached from a pair of eyeglasses in order to secure/release the device to/from the eyeglasses, multiple times. The clip-on device holds at least an inward-facing camera, a processor, a battery, and a wireless communication module. Most of the clip-on device may be located in front of the frame (as illustrated in FIG. 14b, FIG. 15b, and FIG. 18), or alternatively, most of the clip-on device may be located behind the frame, as illustrated in FIG. 16b and FIG. 17b.

Figure 14A:
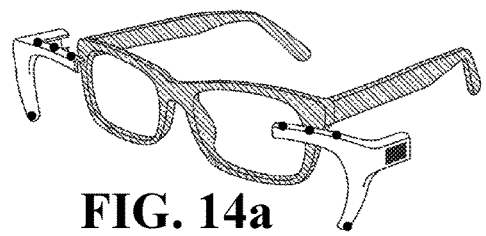
FIG. 14a, FIG. 14b, and FIG. 14c illustrate embodiments of two right and left clip-on devices that are configured to attached/detached from an eyeglasses frame.
Figure 14B:
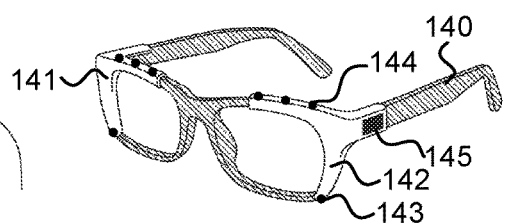
Figure 14C:
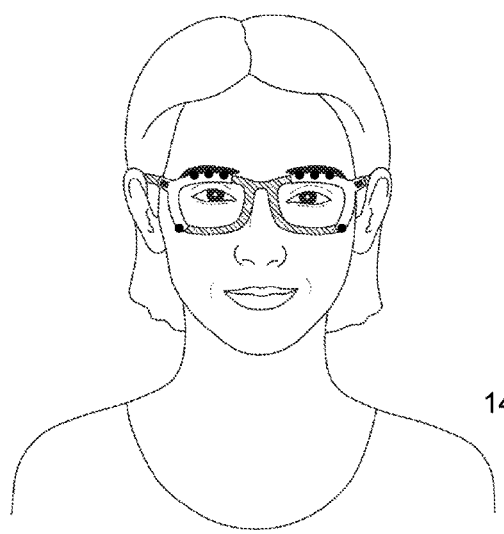

FIG. 14a, FIG. 14b, and FIG. 14c illustrate two right and left clip-on devices 141 and 142, respectively, configured to attached/detached from an eyeglasses frame 140. The clip-on device 142 includes an inward-facing head-mounted camera 143 pointed at a region on the lower part of the face (such as the upper lip, mouth, nose, and/or cheek), an inward-facing head-mounted camera 144 pointed at the forehead, and other electronics 145 (such as a processor, a battery, and/or a wireless communication module). The clip-on devices 141 and 142 may include additional cameras illustrated in the drawings as black circles.

Figure 15A:
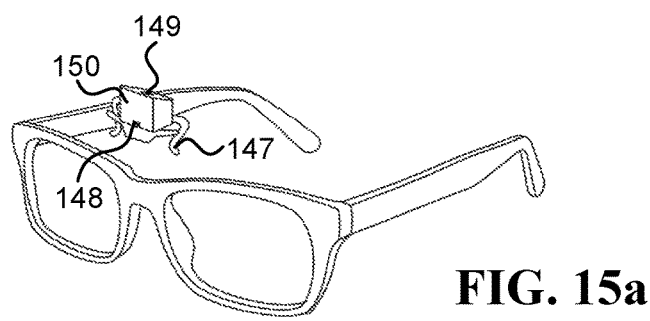
FIG. 15a and FIG. 15b illustrate an embodiment of a clip-on device that includes inward-facing head-mounted cameras pointed at the lower part of the face and the forehead.
Figure 15B:
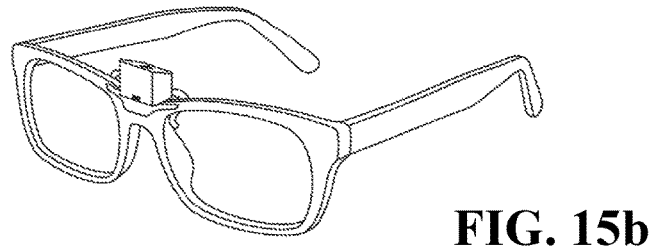

FIG. 15a and FIG. 15b illustrate a clip-on device 147 that includes an inward-facing head-mounted camera 148 pointed at a region on the lower part of the face (such as the nose), and an inward-facing head-mounted camera 149 pointed at the forehead. The other electronics (such as a processor, a battery, and/or a wireless communication module) is located inside the box 150, which also holds the cameras 148 and 149.

Figure 16A:
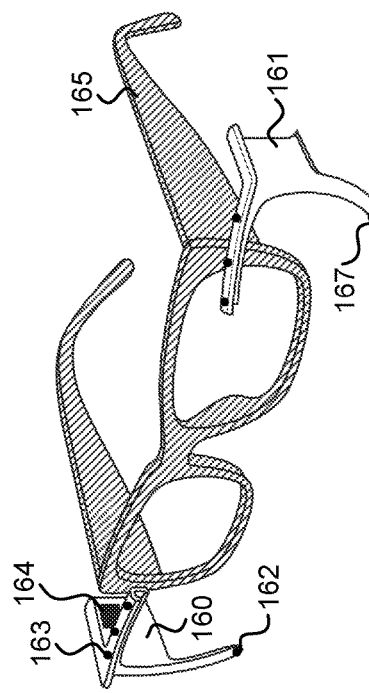
FIG. 16a and FIG. 16b illustrate embodiments of right and left clip-on devices that are configured to be attached behind an eyeglasses frame.
Figure 16B:
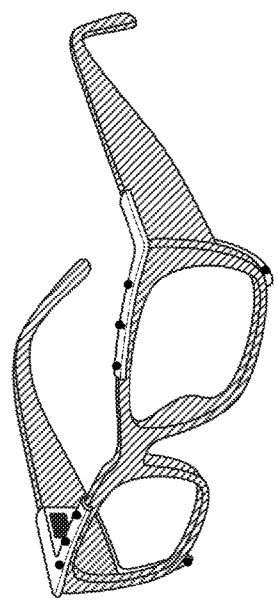

FIG. 16a and FIG. 16b illustrate two right and left clip-on devices 160 and 161, respectively, configured to be attached behind an eyeglasses frame 165. The clip-on device 160 includes an inward-facing head-mounted camera 162 pointed at a region on the lower part of the face (such as the upper lip, mouth, nose, and/or cheek), an inward-facing head-mounted camera 163 pointed at the forehead, and other electronics 164 (such as a processor, a battery, and/or a wireless communication module). The clip-on devices 160 and 161 may include additional cameras illustrated in the drawings as black circles.

Figure 17A:
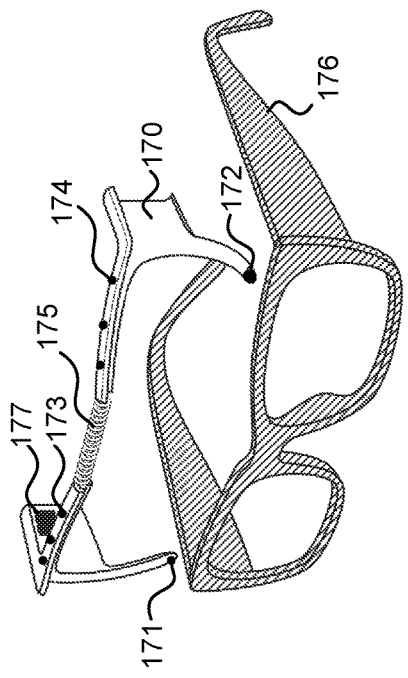
FIG. 17a and FIG. 17b illustrate an embodiment of a single-unit clip-on device that is configured to be attached behind an eyeglasses frame.
Figure 17B:
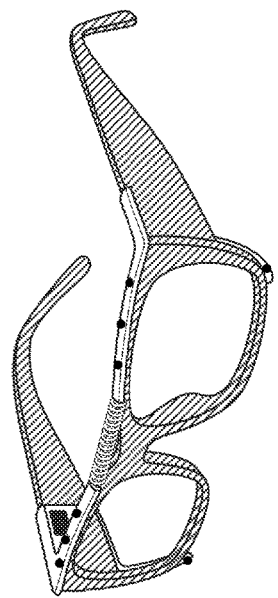
Figure 18:
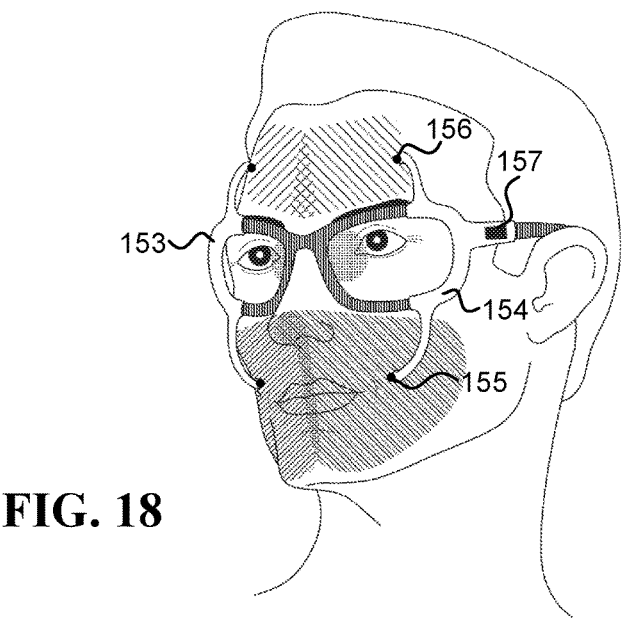
FIG. 18 illustrates embodiments of right and left clip-on devices, which are configured to be attached/detached from an eyeglasses frame, and have protruding arms to hold inward-facing head-mounted cameras.

FIG. 17a and FIG. 17b illustrate a single-unit clip-on device 170, configured to be attached behind an eyeglasses frame 176. The single-unit clip-on device 170 includes inward-facing head-mounted cameras 171 and 172 pointed at regions on the lower part of the face (such as the upper lip, mouth, nose, and/or cheek), inward-facing head-mounted cameras 173 and 174 pointed at the forehead, a spring 175 configured to apply force that holds the clip-on device 170 to the frame 176, and other electronics 177 (such as a processor, a battery, and/or a wireless communication module). The clip-on device 170 may include additional cameras illustrated in the drawings as black circles.

FIG. 18 illustrates two right and left clip-on devices 153 and 154, respectively, configured to attached/detached from an eyeglasses frame, and having protruding arms to hold the inward-facing head-mounted cameras. Head-mounted camera 155 measures a region on the lower part of the face, head-mounted camera 156 measures regions on the forehead, and the left clip-on device 154 further includes other electronics 157 (such as a processor, a battery, and/or a wireless communication module). The clip-on devices 153 and 154 may include additional cameras illustrated in the drawings as black circles.

It is noted that the elliptic and other shapes of the ROIs in some of the drawings are just for illustration purposes, and the actual shapes of the ROIs are usually not as illustrated. It is possible to calculate the accurate shape of an ROI using various methods, such as a computerized simulation using a 3D model of the face and a model of a head-mounted system (HMS) to which a thermal camera is physically coupled, or by placing a LED instead of the sensor (while maintaining the same field of view) and observing the illumination pattern on the face. Furthermore, illustrations and discussions of a camera represent one or more cameras, where each camera may have the same FOV and/or different FOVs. Unless indicated to the contrary, the cameras may include one or more sensing elements (pixels), even when multiple sensing elements do not explicitly appear in the figures; when a camera includes multiple sensing elements then the illustrated ROI usually refers to the total ROI captured by the camera, which is made of multiple regions that are respectively captured by the different sensing elements. The positions of the cameras in the figures are just for illustration, and the cameras may be placed at other positions on the HMS.

Sentences in the form of an "ROI on an area", such as ROI on the forehead or an ROI on the nose, refer to at least a portion of the area. Depending on the context, and especially when using a CAM having just one pixel or a small number of pixels, the ROI may cover another area (in addition to the area). For example, a sentence in the form of "an ROI on the nose" may refer to either: 100% of the ROI is on the nose, or some of the ROI is on the nose and some of the ROI is on the upper lip.

Various embodiments described herein involve detections of physiological responses based on user measurements. Some examples of physiological responses include stress, an allergic reaction, an asthma attack, a stroke, dehydration, intoxication, or a headache (which includes a migraine). Other examples of physiological responses include manifestations of fear, startle, sexual arousal, anxiety, joy, pain or guilt. Still other examples of physiological responses include physiological signals such as a heart rate or a value of a respiratory parameter of the user. Optionally, detecting a physiological response may involve one or more of the following: determining whether the user has/had the physiological response, identifying an imminent attack associated with the physiological response, and/or calculating the extent of the physiological response.

In some embodiments, detection of the physiological response is done by processing thermal measurements that fall within a certain window of time that characterizes the physiological response. For example, depending on the physiological response, the window may be five seconds long, thirty seconds long, two minutes long, five minutes long, fifteen minutes long, or one hour long. Detecting the physiological response may involve analysis of thermal measurements taken during multiple of the above-described windows, such as measurements taken during different days. In some embodiments, a computer may receive a stream of thermal measurements, taken while the user wears an HMS with coupled thermal cameras during the day, and periodically evaluate measurements that fall within a sliding window of a certain size.

In some embodiments, models are generated based on measurements taken over long periods. Sentences of the form of "measurements taken during different days" or "measurements taken over more than a week" are not limited to continuous measurements spanning the different days or over the week, respectively. For example, "measurements taken over more than a week" may be taken by eyeglasses equipped with thermal cameras, which are worn for more than a week, 8 hours a day. In this example, the user is not required to wear the eyeglasses while sleeping in order to take measurements over more than a week. Similarly, sentences of the form of "measurements taken over more than 5 days, at least 2 hours a day" refer to a set comprising at least 10 measurements taken over 5 different days, where at least two measurements are taken each day at times separated by at least two hours.

Utilizing measurements taken of a long period (e.g., measurements taken on "different days") may have an advantage, in some embodiments, of contributing to the generalizability of a trained model. Measurements taken over the long period likely include measurements taken in different environments and/or measurements taken while the measured user was in various physiological and/or mental states (e.g., before/after meals and/or while the measured user was sleepy/energetic/happy/depressed, etc.). Training a model on such data can improve the performance of systems that utilize the model in the diverse settings often encountered in real-world use (as opposed to controlled laboratory-like settings). Additionally, taking the measurements over the long period may have the advantage of enabling collection of a large amount of training data that is required for some machine learning approaches (e.g., "deep learning").

Detecting the physiological response may involve performing various types of calculations by a computer. Optionally, detecting the physiological response may involve performing one or more of the following operations: comparing thermal measurements to a threshold (when the threshold is reached that may be indicative of an occurrence of the physiological response), comparing thermal measurements to a reference time series, and/or by performing calculations that involve a model trained using machine learning methods. Optionally, the thermal measurements upon which the one or more operations are performed are taken during a window of time of a certain length, which may optionally depend on the type of physiological response being detected. In one example, the window may be shorter than one or more of the following durations: five seconds, fifteen seconds, one minute, five minutes, thirty minute, one hour, four hours, one day, or one week. In another example, the window may be longer than one or more of the aforementioned durations. Thus, when measurements are taken over a long period, such as measurements taken over a period of more than a week, detection of the physiological response at a certain time may be done based on a subset of the measurements that falls within a certain window near the certain time; the detection at the certain time does not necessarily involve utilizing all values collected throughout the long period.

In some embodiments, detecting the physiological response of a user may involve utilizing baseline thermal measurement values, most of which were taken when the user was not experiencing the physiological response. Optionally, detecting the physiological response may rely on observing a change to typical temperatures at one or more ROIs (the baseline), where different users might have different typical temperatures at the ROIs (i.e., different baselines). Optionally, detecting the physiological response may rely on observing a change to a baseline level, which is determined based on previous measurements taken during the preceding minutes and/or hours.

In some embodiments, detecting a physiological response involves determining the extent of the physiological response, which may be expressed in various ways that are indicative of the extent of the physiological response, such as: (i) a binary value indicative of whether the user experienced, and/or is experiencing, the physiological response, (ii) a numerical value indicative of the magnitude of the physiological response, (iii) a categorical value indicative of the severity/extent of the physiological response, (iv) an expected change in thermal measurements of an ROI (denoted $TH_{ROI}$ or some variation thereof), and/or (v) rate of change in $TH_{ROI}$. Optionally, when the physiological response corresponds to a physiological signal (e.g., a heart rate, a breathing rate, and an extent of frontal lobe brain activity), the extent of the physiological response may be interpreted as the value of the physiological signal.

One approach for detecting a physiological response, which may be utilized in some embodiments, involves comparing thermal measurements of one or more ROIs to a threshold. In these embodiments, the computer may detect the physiological response by comparing the thermal measurements, and/or values derived therefrom (e.g., a statistic of the measurements and/or a function of the measurements), to the threshold to determine whether it is reached. Optionally, the threshold may include a threshold in the time domain, a threshold in the frequency domain, an upper threshold, and/or a lower threshold. When a threshold involves a certain change to temperature, the certain change may be positive (increase in temperature) or negative (decrease in temperature). Different physiological responses described herein may involve different types of thresholds, which may be an upper threshold (where reaching the threshold means≥the threshold) or a lower threshold (where reaching the threshold means≤the threshold); for example, each physiological response may involve at least a certain degree of heating, or at least a certain degree cooling, at a certain ROI on the face.

Another approach for detecting a physiological response, which may be utilized in some embodiments, may be applicable when the thermal measurements of a user are treated as time series data. For example, the thermal measurements may include data indicative of temperatures at one or more ROIs at different points of time during a certain period. In some embodiments, the computer may compare thermal measurements (represented as a time series) to one or more reference time series that correspond to periods of time in which the physiological response occurred. Additionally or alternatively, the computer may compare the thermal measurements to other reference time series corresponding to times in which the physiological response did not occur. Optionally, if the similarity between the thermal measurements and a reference time series corresponding to a physiological response reaches a threshold, this is indicative of the fact that the thermal measurements correspond to a period of time during which the user had the physiological response. Optionally, if the similarity between the thermal measurements and a reference time series that does not correspond to a physiological response reaches another threshold, this is indicative of the fact that the thermal measurements correspond to a period of time in which the user did not have the physiological response. Time series analysis may involve various forms of processing involving segmenting data, aligning data, clustering, time warping, and various functions for determining similarity between sequences of time series data. Some of the techniques that may be utilized in various embodiments are described in Ding, Hui, et al. "Querying and mining of time series data: experimental comparison of representations and distance measures." Proceedings of the VLDB Endowment 1.2 (2008): 1542-1552, and in Wang, Xiaoyue, et al. "Experimental comparison of representation methods and distance measures for time series data." Data Mining and Knowledge Discovery 26.2 (2013): 275-309.

Herein, "machine learning" methods refers to learning from examples using one or more approaches. Optionally, the approaches may be considered supervised, semi-supervised, and/or unsupervised methods. Examples of machine learning approaches include: decision tree learning, association rule learning, regression models, nearest neighbors classifiers, artificial neural networks, deep learning, inductive logic programming, support vector machines, clustering, Bayesian networks, reinforcement learning, representation learning, similarity and metric learning, sparse dictionary learning, genetic algorithms, rule-based machine learning, and/or learning classifier systems.

Herein, a "machine learning-based model" is a model trained using machine learning methods. For brevity's sake, at times, a "machine learning-based model" may simply be called a "model". Referring to a model as being "machine learning-based" is intended to indicate that the model is trained using machine learning methods (otherwise, "model" may also refer to a model generated by methods other than machine learning).

In some embodiments, which involve utilizing a machine learning-based model, a computer is configured to detect the physiological response by generating feature values based on the thermal measurements (and possibly other values), and/or based on values derived therefrom (e.g., statistics of the measurements). The computer then utilizes the machine learning-based model to calculate, based on the feature values, a value that is indicative of whether, and/or to what extent, the user is experiencing (and/or is about to experience) the physiological response. Optionally, calculating said value is considered "detecting the physiological response". Optionally, the value calculated by the computer is indicative of the probability that the user has/had the physiological response.

Herein, feature values may be considered input to a computer that utilizes a model to perform the calculation of a value, such as the value indicative of the extent of the physiological response mentioned above. It is to be noted that the terms "feature" and "feature value" may be used interchangeably when the context of their use is clear. However, a "feature" typically refers to a certain type of value, and represents a property, while "feature value" is the value of the property with a certain instance (sample). For example, a feature may be temperature at a certain ROI, while the feature value corresponding to that feature may be 36.9° C. in one instance and 37.3° C. in another instance.

In some embodiments, a machine learning-based model used to detect a physiological response is trained based on data that includes samples. Each sample includes feature values and a label. The feature values may include various types of values. At least some of the feature values of a sample are generated based on measurements of a user taken during a certain period of time (e.g., thermal measurements taken during the certain period of time). Optionally, some of the feature values may be based on various other sources of information described herein. The label is indicative of a physiological response of the user corresponding to the certain period of time. Optionally, the label may be indicative of whether the physiological response occurred during the certain period and/or the extent of the physiological response during the certain period. Additionally or alternatively, the label may be indicative of how long the physiological response lasted. Labels of samples may be generated using various approaches, such as self-report by users, annotation by experts that analyze the training data, automatic annotation by a computer that analyzes the training data and/or analyzes additional data related to the training data, and/or utilizing additional sensors that provide data useful for generating the labels. It is to be noted that herein when it is stated that a model is trained based on certain measurements (e.g., "a model trained based on $TH_{ROI}$ taken on different days"), it means that the model was trained on samples comprising feature values generated based on the certain measurements and labels corresponding to the certain measurements. Optionally, a label corresponding to a measurement is indicative of the physiological response at the time the measurement was taken.

Various types of feature values may be generated based on thermal measurements. In one example, some feature values are indicative of temperatures at certain ROIs. In another example, other feature values may represent a temperature change at certain ROIs. The temperature changes may be with respect to a certain time and/or with respect to a different ROI. In order to better detect physiological responses that take some time to manifest, in some embodiments, some feature values may describe temperatures (or temperature changes) at a certain ROI at different points of time. Optionally, these feature values may include various functions and/or statistics of the thermal measurements such as minimum/maximum measurement values and/or average values during certain windows of time.

It is to be noted that when it is stated that feature values are generated based on data comprising multiple sources, it means that for each source, there is at least one feature value that is generated based on that source (and possibly other data). For example, stating that feature values are generated from thermal measurements of first and second ROIs ($TH_{ROI1}$ and $TH_{ROI2}$, respectively) means that the feature values may include a first feature value generated based on $TH_{ROI1}$ and a second feature value generated based on $TH_{ROI2}$. Optionally, a sample is considered generated based on measurements of a user (e.g., measurements comprising $TH_{ROI1}$ and $TH_{ROI2}$) when it includes feature values generated based on the measurements of the user.

In addition to feature values that are generated based on thermal measurements, in some embodiments, at least some feature values utilized by a computer (e.g., to detect a physiological response or train a mode) may be generated based on additional sources of data that may affect temperatures measured at various facial ROIs. Some examples of the additional sources include: (i) measurements of the environment such as temperature, humidity level, noise level, elevation, air quality, a wind speed, precipitation, and infrared radiation; (ii) contextual information such as the time of day (e.g., to account for effects of the circadian rhythm), day of month (e.g., to account for effects of the lunar rhythm), day in the year (e.g., to account for seasonal effects), and/or stage in a menstrual cycle; (iii) information about the user being measured such as sex, age, weight, height, and/or body build. Alternatively or additionally, at least some feature values may be generated based on physiological signals of the user obtained by sensors that are not thermal cameras, such as a visible-light camera, a photoplethysmogram (PPG) sensor, an electrocardiogram (ECG) sensor, an electroencephalography (EEG) sensor, a galvanic skin response (GSR) sensor, or a thermistor.

The machine learning-based model used to detect a physiological response may be trained, in some embodiments, based on data collected in day-to-day, real world scenarios. As such, the data may be collected at different times of the day, while users perform various activities, and in various environmental conditions. Utilizing such diverse training data may enable a trained model to be more resilient to the various effects different conditions can have on the values of thermal measurements, and consequently, be able to achieve better detection of the physiological response in real world day-to-day scenarios.

Since real world day-to-day conditions are not the same all the time, sometimes detection of the physiological response may be hampered by what is referred to herein as "confounding factors". A confounding factor can be a cause of warming and/or cooling of certain regions of the face, which is unrelated to a physiological response being detected, and as such, may reduce the accuracy of the detection of the physiological response. Some examples of confounding factors include: (i) environmental phenomena such as direct sunlight, air conditioning, and/or wind; (ii) things that are on the user's face, which are not typically there and/or do not characterize the faces of most users (e.g., cosmetics, ointments, sweat, hair, facial hair, skin blemishes, acne, inflammation, piercings, body paint, and food leftovers); (iii) physical activity that may affect the user's heart rate, blood circulation, and/or blood distribution (e.g., walking, running, jumping, and/or bending over); (iv) consumption of substances to which the body has a physiological response that may involve changes to temperatures at various facial ROIs, such as various medications, alcohol, caffeine, tobacco, and/or certain types of food; and/or (v) disruptive facial movements (e.g., frowning, talking, eating, drinking, sneezing, and coughing).

Occurrences of confounding factors may not always be easily identified in thermal measurements. Thus, in some embodiments, systems may incorporate measures designed to accommodate for the confounding factors. In some embodiments, these measures may involve generating feature values that are based on additional sensors, other than the thermal cameras. In some embodiments, these measures may involve refraining from detecting the physiological response, which should be interpreted as refraining from providing an indication that the user has the physiological response. For example, if an occurrence of a certain confounding factor is identified, such as strong directional sunlight that heats one side of the face, the system may refrain from detecting that the user had a stroke. In this example, the user may not be alerted even though a temperature difference between symmetric ROIs on both sides of the face reaches a threshold that, under other circumstances, would warrant alerting the user.

Training data used to train a model for detecting a physiological response may include, in some embodiments, a diverse set of samples corresponding to various conditions, some of which involve occurrence of confounding factors (when there is no physiological response and/or when there is a physiological response). Having samples in which a confounding factor occurs (e.g., the user is in direct sunlight or touches the face) can lead to a model that is less susceptible to wrongfully detect the physiological response (which may be considered an occurrence of a false positive) in real world situations.

When a model is trained with training data comprising samples generated from measurements of multiple users, the model may be considered a general model. When a model is trained with training data comprising at least a certain proportion of samples generated from measurements of a certain user, and/or when the samples generated from the measurements of the certain user are associated with at least a certain proportion of weight in the training data, the model may be considered a personalized model for the certain user. Optionally, the personalized model for the certain user provides better results for the certain user, compared to a general model that was not personalized for the certain user. Optionally, personalized model may be trained based on measurements of the certain user, which were taken while the certain user was in different situations; for example, train the model based on measurements taken while the certain user had a headache/epilepsy/stress/anger attack, and while the certain user did not have said attack. Additionally or alternatively, the personalized model may be trained based on measurements of the certain user, which were taken over a duration long enough to span different situations; examples of such long enough durations may include: a week, a month, six months, a year, and three years.

Training a model that is personalized for a certain user may require collecting a sufficient number of training samples that are generated based on measurements of the certain user. Thus, initially detecting the physiological response with the certain user may be done utilizing a general model, which may be replaced by a personalized model for the certain user, as a sufficiently large number of samples are generated based on measurements of the certain user. Another approach involves gradually modifying a general model based on samples of the certain user in order to obtain the personalized model.

After a model is trained, the model may be provided for use by a system that detects the physiological response. Providing the model may involve performing different operations. In one embodiment, providing the model to the system involves forwarding the model to the system via a computer network and/or a shared computer storage medium (e.g., writing the model to a memory that may be accessed by the system that detects the physiological response). In another embodiment, providing the model to the system involves storing the model in a location from which the system can retrieve the model, such as a database and/or cloud-based storage from which the system may retrieve the model. In still another embodiment, providing the model involves notifying the system regarding the existence of the model and/or regarding an update to the model. Optionally, this notification includes information needed in order for the system to obtain the model.

A model for detecting a physiological response may include different types of parameters. Following are some examples of various possibilities for the model and the type of calculations that may be accordingly performed by a computer in order to detect the physiological response: (a) the model comprises parameters of a decision tree. Optionally, the computer simulates a traversal along a path in the decision tree, determining which branches to take based on the feature values. A value indicative of the physiological response may be obtained at the leaf node and/or based on calculations involving values on nodes and/or edges along the path; (b) the model comprises parameters of a regression model (e.g., regression coefficients in a linear regression model or a logistic regression model). Optionally, the computer multiplies the feature values (which may be considered a regressor) with the parameters of the regression model in order to obtain the value indicative of the physiological response; and/or (c) the model comprises parameters of a neural network. For example, the parameters may include values defining at least the following: (i) an interconnection pattern between different layers of neurons, (ii) weights of the interconnections, and (iii) activation functions that convert each neuron's weighted input to its output activation. Optionally, the computer provides the feature values as inputs to the neural network, computes the values of the various activation functions and propagates values between layers, and obtains an output from the network, which is the value indicative of the physiological response.

A user interface (UI) may be utilized, in some embodiments, to notify the user and/or some other entity, such as a caregiver, about the physiological response and/or present an alert responsive to an indication that the extent of the physiological response reaches a threshold. The UI may include a screen to display the notification and/or alert, a speaker to play an audio notification, a tactile UI, and/or a vibrating UI. In some embodiments, "alerting" about a physiological response of a user refers to informing about one or more of the following: the occurrence of a physiological response that the user does not usually have (e.g., a stroke, intoxication, and/or dehydration), an imminent physiological response (e.g., an allergic reaction, an epilepsy attack, and/or a migraine), and an extent of the physiological response reaching a threshold (e.g., stress and/or anger reaching a predetermined level).

Figure 19:
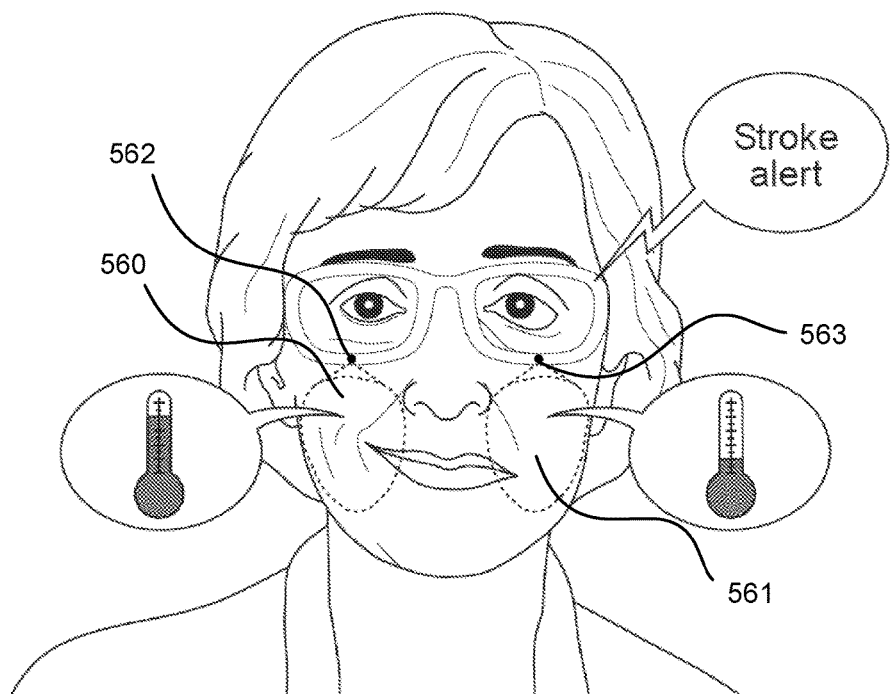
FIG. 19 illustrates a scenario in which an alert regarding a possible stroke is issued.

FIG. 19 illustrates a scenario in which an alert regarding a possible stroke is issued. The figure illustrates a user wearing a frame with at least two CAMs (562 and 563) for measuring ROIs on the right and left cheeks (ROIs 560 and 561, respectively). The measurements indicate that the left side of the face is colder than the right side of the face. Based on these measurements, and possibly additional data, the system detects the stroke and issues an alert. Optionally, the user's facial expression is slightly distorted and asymmetric, and a VCAM provides additional data in the form of images that may help detecting the stroke.

The CAMs can take respiratory-related thermal measurements when their ROIs are on the user's upper lip, the user's mouth, the space where the exhale stream form the user's nose flows, and/or the space where the exhale stream from the user's mouth flows. In some embodiments, one or more of the following respiratory parameters may be calculated based on the respiratory-related thermal measurements taken during a certain period of time:

"Breathing rate" represents the number of breaths per minute the user took during the certain period. The breathing rate may also be formulated as the average time between successive inhales and/or the average between successive exhales.

"Respiration volume" represents the volume of air breathed over a certain duration (usually per minute), the volume of air breathed during a certain breath, tidal volume, and/or the ratio between two or more breaths. For example, the respiration volume may indicate that a first breath was deeper than a second breath, or that breaths during a first minute were shallower than breaths during a second minute.

"Mouth breathing vs nasal breathing" indicates whether during the certain period the user breathed mainly through the mouth (a state characterized as "mouth breathing") or mainly through the nose (a state characterized as "nose breathing" or "nasal breathing"). Optionally, this parameter may represent the ratio between nasal and mouth breathing, such as a proportion of the certain period during which the breathing was more mouth breathing, and/or the relative volume of air exhaled through the nose vs the mouth. In one example, breathing mainly through the mouth refers to inhaling more than 50% of the air through the mouth (and less than 50% of the air through the nose).

"Exhale duration/Inhale duration" represents the exhale (s) duration during the certain period, the inhale(s) duration during the certain period, and/or a ratio of the two aforementioned durations. Optionally, this respiratory parameter may represent one or more of the following: (i) the average duration of the exhales and/or inhales, (ii) a maximum and/or minimum duration of the exhales and/or inhales during the certain period, and (iii) a proportion of times in which the duration of exhaling and/or inhaling reached a certain threshold.

"Post-exhale breathing pause" represents the time that elapses between when the user finishes exhaling and starts inhaling again. "Post-inhale breathing pause" represents the time that elapses between when the user finishes inhaling and when the user starts exhaling after that. The post exhale/inhale breathing pauses may be formulated utilizing various statistics, such as an average post exhale/inhale breathing pause during a certain period, a maximum or minimum duration of post exhale/inhale breathing pause during the certain period, and/or a proportion of times in which the duration of post exhale/inhale breathing pause reached a certain threshold.

"Dominant nostril" is the nostril through which most of the air is exhaled (when exhaling through the nose). Normally the dominant nostril changes during the day, and the exhale is considered balanced when the amount of air exhaled through each nostril is similar. Optionally, the breathing may be considered balanced when the difference between the volumes of air exhaled through the right and left nostrils is below a predetermined threshold, such as 20% or 10%. Additionally or alternatively, the breathing may be considered balanced during a certain duration around the middle of the switching from right to left or left to right nostril dominance. For example, the certain duration of balanced breathing may be about 4 minutes at the middle of the switching between dominant nostrils.

"Temperature of the exhale stream" may be measured based on thermal measurements of the stream that flows from one or both nostrils, and/or the heat pattern generated on the upper lip by the exhale stream from the nose. In one example, it is not necessary to measure the exact temperature of the exhale stream as long as the system is able to differentiate between different temperatures of the exhale stream based on the differences between series of thermal measurements taken at different times. Optionally, the series of thermal measurements that are compared are temperature measurements received from the same pixel(s) of a head-mounted thermal camera.

"Shape of the exhale stream" (also referred to as "SHAPE") represents the three-dimensional (3D) shape of the exhale stream from at least one of the nostrils. The SHAPE changes during the day and may reflect the mental, physiological, and/or energetic state of a user. Usually the temperature of the exhale stream is different from the temperature of the air in the environment; this enables a thermal camera, which captures a portion of the volume through which the exhale stream flows, to take a measurement indicative of the SHAPE, and/or to differentiate between different shapes of the exhale stream (SHAPEs). Additionally, the temperature of the exhale stream is usually different from the temperature of the upper lip, and thus exhale streams having different shapes may generate different thermal patterns on the upper lip. Measuring these different thermal patterns on the upper lip may enable a computer to differentiate between different SHAPEs. In one embodiment, differences between values measured by adjacent thermal pixels of CAM, which measure the exhale stream and/or the upper lip over different time intervals, may correspond to different SHAPEs. In one example, it is not necessary to measure the exact SHAPE as long as it is possible to differentiate between different SHAPEs based on the differences between the values of the adjacent thermal pixels. In another embodiment, differences between average values, measured by the same thermal pixel over different time intervals, may correspond to different SHAPEs. In still another embodiment, the air that is within certain boundaries of a 3D shape that protrudes from the user's nose, which is warmer than the environment air, as measured by CAM, is considered to belong to the exhale stream.

In one embodiment, the SHAPE may be represented by one or more thermal images taken by one or more CAMs. In this embodiment, the shape may correspond to a certain pattern in the one or more images and/or a time series describing a changing pattern in multiple images. In another embodiment, the SHAPE may be represented by at least one of the following parameters: the angle from which the exhale stream blows from a nostril, the width of the exhale stream, the length of the exhale stream, and other parameters that are indicative of the 3D SHAPE. Optionally, the SHAPE may be defined by the shape of a geometric body that confines it, such as a cone or a cylinder, protruding from the user's nose. For example, the SHAPE may be represented by parameters such as the cone's height, the radius of the cone's base, and/or the angle between the cone's altitude axis and the nostril.

"Smoothness of the exhale stream" represents a level of smoothness of the exhale stream from the nose and/or the mouth. In one embodiment, the smoothness of the exhale stream is a value that can be determined based on observing the smoothness of a graph of the respiratory-related thermal measurements. Optionally, it is unnecessary for the system to measure the exact smoothness of the exhale stream as long as it is able to differentiate between smoothness levels of respiratory-related thermal measurements taken at different times. Optionally, the compared thermal measurements taken at different times may be measured by the same pixels and/or by different pixels. As a rule of thumb, the smoother the exhale stream, the lower the stress and the better the physical condition. For example, the exhale stream of a healthy young person is often smoother than the exhale stream of an elderly person, who may even experience short pauses in the act of exhaling.

There are well known mathematical methods to calculate the smoothness of a graph, such as Fourier transform analysis, polynomial fit, differentiability classes, multivariate differentiability classes, parametric continuity, and/or geometric continuity. In one example, the smoothness of $TH_{ROI}$ indicative of the exhale stream is calculated based on a Fourier transform of a series of $TH_{ROI}$. In the case of Fourier transform, the smaller the power of the high-frequencies portion, the smoother the exhale is, and vice versa. Optionally, one or more predetermined thresholds differentiate between the high-frequency and low-frequency portions in the frequency domain. In another example, the smoothness of $TH_{ROI}$ indicative of the exhale stream is calculated using a polynomial fit (with a bounded degree) of a series of $TH_{ROI}$. Optionally, the degree of the polynomial used for the fit is proportional (e.g., linear) to the number of exhales in the time series. In the case of polynomial fit, the smoothness may be a measure of the goodness of fit between the series of $TH_{ROI}$ and the polynomial. For example, the lower the squared error, the smoother the graph is considered. In still another embodiment, the smoothness of $TH_{ROI}$ indicative of the exhale stream may be calculated using a machine learning-based model trained with training data comprising reference time series of $TH_{ROI}$ for which the extent of smoothness is known.

In an alternative embodiment, a microphone is used to measure the exhale sounds. The smoothness of the exhale stream may be a value that is proportional to the smoothness of the audio measurement time series taken by the microphone (e.g., as determined based on the power of the high-frequency portion obtained in a Fourier transform of the time series of the audio).

There are various approaches that may be employed in order to calculate values of one or more of the respiratory parameters mentioned above based on respiratory-related thermal measurements. Optionally, calculating the values of one or more of the respiratory parameters may be based on additional inputs, such as statistics about the user (e.g., age, gender, weight, height, and the like), indications about the user's activity level (e.g., input from a pedometer), and/or physiological signals of the user (e.g., heart rate and respiratory rate). Roughly speaking, some approaches may be considered analytical approaches, while other approaches may involve utilization of a machine learning-based model.

In some embodiments, one or more of the respiratory parameters mentioned above may be calculated based on the respiratory-related thermal measurements by observing differences in thermal measurements. In one embodiment, certain pixels that have alternating temperature changes may be identified as corresponding to exhale streams. In this embodiment, the breathing rate may be a calculated frequency of the alternating temperature changes at the certain pixels. In another embodiment, the relative difference in magnitude of temperature changes at different ROIs, such as the alternating temperature changes that correspond to breathing activity, may be used to characterize different types of breathing. For example, if temperature changes at ROI near the nostrils reach a first threshold, while temperature changes at an ROI related to the mouth do not reach a second threshold, then the breathing may be considered nasal breathing; while if the opposite occurs, the breathing may be considered mouth breathing. In another example, if temperature changes at an ROI near the left nostril and/or on the left side of the upper lip are higher than temperature changes at an ROI near the right nostril and/or on the right side of the upper lip, then the left nostril may be considered the dominant nostril at the time the measurements were taken. In still another example, the value of a respiratory parameter may be calculated as a function of one or more input values from among the respiratory-related thermal measurements.

In other embodiments, one or more of the respiratory parameters may be calculated by generating feature values based on the respiratory-related thermal measurements and utilizing a model to calculate, based on the feature values, the value of a certain respiratory parameter from among the parameters mentioned above. The model for the certain respiratory parameter is trained based on samples. Each sample comprises the feature values based on respiratory-related thermal measurements, taken during a certain period of time, and a label indicative of the value of the certain respiratory parameter during the certain period of time. For example, the feature values generated for a sample may include the values of pixels measured by the one or more cameras, statistics of the values of the pixels, and/or functions of differences of values of pixels at different times. Additionally or alternatively, some of the feature values may include various low-level image analysis features, such as feature derived using Gabor filters, local binary patterns and their derivatives, features derived using algorithms such as SIFT, SURF, and/or ORB, image keypoints, HOG descriptors and features derived using PCA or LDA. The labels of the samples may be obtained through various ways. Some examples of approaches for generating the labels include manual reporting (e.g., a user notes the type of his/her breathing), manual analysis of thermal images (e.g., an expert determines a shape of an exhale stream), and/or utilizing sensors (e.g., a chest strap that measures the breathing rate and volume).

Training the model for the certain respiratory parameter based on the samples may involve utilizing one or more machine learning-based training algorithms, such as a training algorithm for a decision tree, a regression model, or a neural network. Once the model is trained, it may be utilized to calculate the value of the certain respiratory parameter based on feature values generated based on respiratory-related thermal measurements taken during a certain period, for which the label (i.e., the value of the certain respiratory parameter) may not be known.

In one embodiment, a system configured to calculate a respiratory parameter includes an inward-facing head-mounted thermal camera (CAM) and a computer. CAM is worn on a user's head and takes thermal measurements of a region below the nostrils ($TH_{ROI}$), where $TH_{ROI}$ are indicative of the exhale stream. The "region below the nostrils", which is indicative of the exhale stream, refers to one or more regions on the upper lip, the mouth, and/or air volume(s) through which the exhale streams from the nose and/or mouth flow. The flowing of the typically warm air of the exhale stream can change the temperature at the one or more regions, and thus thermal measurements of these one or more regions can provide information about properties of the exhale stream. The computer (i) generates feature values based on $TH_{ROI}$, and (ii) utilizes a model to calculate the respiratory parameter based on the feature values. The respiratory parameter may be indicative of the user's breathing rate, and the model may be trained based on previous $TH_{ROI}$ of the user taken during different days. FIG. 35 illustrates one embodiment of a system for calculating a respiratory parameter. The system includes a computer 445 and CAM that is coupled to the eyeglasses frame worn by the user 420 and provides $TH_{ROI}$ 443.

The computer 445 generates feature values based on $TH_{ROI}$ 443, and possibly other sources of data. Then the computer utilizes a model 442 to calculate, based on the feature values, a value 447 of the respiratory parameter. The value 447 may be indicative of at least one of the following: breathing rate, respiration volume, whether the user is breathing mainly through the mouth or through the nose, exhale (inhale) duration, post-exhale (post-inhale) breathing pause, a dominant nostril, a shape of the exhale stream, smoothness of the exhale stream, and/or temperature of the exhale stream. Optionally, the respiratory parameters calculated by the computer 445 may be indicative of the respiration volume. Optionally, the value 447 is stored (e.g., for life-logging purposes) and/or forwarded to a software agent operating on behalf of the user (e.g., in order for the software agent to make a decision regarding the user).

The feature values generated by the computer 445 may include any of the feature values described in this disclosure that are utilized to detect a physiological response. Optionally, the thermal measurements may undergo various forms of filtering and/or normalization. For example, the feature values generated based on $TH_{ROI}$ may include: time series data comprising values measured by CAM, average values of certain pixels of CAM, and/or values measured at certain times by the certain pixels. Additionally, the feature values may include values generated based on additional measurements of the user taken by one or more additional sensors (e.g., measurements of heart rate, heart rate variability, brainwave activity, galvanic skin response, muscle activity, and/or an extent of movement). Additionally or alternatively, at least some of the feature values may include measurements of the environment in which the user is in, and/or confounding factors that may interfere with the detection.

A user interface (UI) 448 may be utilized to present the value 447 of the respiratory parameter and/or present an alert (e.g., to the user 420 and/or to a caregiver). In one example, UI 448 may be used to alert responsive to an indication that the value 447 reaches a threshold (e.g., when the breathing rate exceeds a certain value and/or after the user 420 spent a certain duration mouth breathing instead of nasal breathing). In another example, UI 448 may be used to alert responsive to detecting that the probability of a respiratory-related attack reaches a threshold.

In one embodiment, the value 447 may be indicative of the smoothness of the exhale stream. Optionally, the value 447 may be presented to the user 420 to increase the user's awareness to the smoothness of his/her exhale stream. Optionally, responsive to detecting that the smoothness is below a predetermined threshold, the computer 445 may issue an alert for the user 420 (e.g., via the UI 448) in order to increase the user's awareness to the user's breathing.

The model 442 is trained on data that includes previous $TH_{ROI}$ of the user 420 and possibly other users. Optionally, the previous measurements were taken on different days and/or over a period longer than a week. Training the model 442 typically involves generating samples based on the previous $TH_{ROI}$ and corresponding labels indicative of values of the respiratory parameter. The labels may come from different sources. In one embodiment, one or more of the labels may be generated using a sensor that is not a thermal camera, which may or may not be physically coupled to a frame worn by the user. The sensor's measurements may be analyzed by a human expert and/or a software program in order to generate the labels. In one example, the sensor is part of a smart shirt and/or chest strap that measures various respiratory (and other) parameters, such as Hexoskin™ smart shirt. In another embodiment, one or more of the labels may come from an external source such as an entity that observes the user, which may be a human observer or a software program. In yet another embodiment, one or more of the labels may be provided by the user, for example by indicating whether he/she is breathing through the mouth or nose and/or which nostril is dominant.

The samples used to train the model 442 usually include samples corresponding to different values of the respiratory parameter. In some embodiments, the samples used to train the model 442 include samples generated based on $TH_{ROI}$ taken at different times of the day, while being at different locations, and/or while conducting different activities. In one example, the samples are generated based on $TH_{ROI}$ taken in the morning and $TH_{ROI}$ taken in the evening. In another example, the samples are generated based on $TH_{ROI}$ of a user taken while being indoors, and $TH_{ROI}$ of the user taken while being outdoors. In yet another example, the samples are generated based on $TH_{ROI}$ taken while a user was sitting down, and $TH_{ROI}$ taken while the user was walking, running, and/or engaging in physical exercise (e.g., dancing, biking, etc.).

Additionally or alternatively, the samples used to train the model 442 may be generated based on $TH_{ROI}$ taken while various environmental conditions persisted. For example, the samples include first and second samples generated based on $TH_{ROI}$ taken while the environment had first and second temperatures, with the first temperature being at least 10° C. warmer than the second temperature. In another example, the samples include samples generated based on measurements taken while there were different extents of direct sunlight and/or different extents of wind blowing.

Various computational approaches may be utilized to train the model 442 based on the samples described above. In one example, training the model 442 may involve selecting a threshold based on the samples. Optionally, if a certain feature value reaches the threshold then a certain respiratory condition is detected (e.g., unsmooth breathing). Optionally, the model 442 includes a value describing the threshold. In another example, a machine learning-based training algorithm may be utilized to train the model 442 based on the samples. Optionally, the model 442 includes parameters of at least one of the following types of models: a regression model, a neural network, a nearest neighbor model, a support vector machine, a support vector machine for regression, a naïve Bayes model, a Bayes network, and a decision tree.

In some embodiments, a deep learning algorithm may be used to train the model 442. In one example, the model 442 may include parameters describing multiple hidden layers of a neural network. In one embodiment, when $TH_{ROI}$ include measurements of multiple pixels, the model 442 may include a convolution neural network (CNN). In one example, the CNN may be utilized to identify certain patterns in the thermal images, such as patterns of temperatures in the region of the exhale stream that may be indicative of a respiratory parameter, which involve aspects such as the location, direction, size, and/or shape of an exhale stream from the nose and/or mouth. In another example, calculating a value of a respiratory parameter, such as the breathing rate, may be done based on multiple, possibly successive, thermal measurements. Optionally, calculating values of the respiratory parameter based on thermal measurements may involve retaining state information that is based on previous measurements. Optionally, the model 442 may include parameters that describe an architecture that supports such a capability. In one example, the model 442 may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using bidirectional recurrent neural network architecture (BRNN).

The computer 445 may detect a respiratory-related attack (such as an asthma attack, an epileptic attack, an anxiety attack, a panic attack, and a tantrum) based on feature values generated based on $TH_{ROI}$ 443. The computer 445 may further receive additional inputs (such as indications of consuming a substance, a situation of the user, and/or thermal measurements of the forehead), and detect the respiratory-related attack based on the additional inputs. For example, the computer 445 may generate one or more of the feature values used to calculate the value 447 based on the additional inputs.

In a first embodiment, the computer 445 utilizes an indication of consumption of a substance to detect a respiratory-related attack. Optionally, the model 442 is trained based on: a first set of $TH_{ROI}$ taken while the user experienced a respiratory-related attack after consuming the substance, and a second set of $TH_{ROI}$ taken while the user did not experience a respiratory-related attack after consuming the substance. The duration to which "after consuming" refers depends on the substance and may last from minutes to hours. Optionally, the consuming of the substance involves consuming a certain drug and/or consuming a certain food item, and the indication is indicative of the time and/or the amount consumed.

In a second embodiment, the computer 445 utilizes an indication of a situation of the user to detect a respiratory-related attack. Optionally, the model 442 is trained based on: a first set of $TH_{ROI}$ taken while the user was in the situation and experienced a respiratory-related attack, and a second set of $TH_{ROI}$ taken while the user was in the situation and did not experience a respiratory-related attack. Optionally, the situation involves (i) interacting with a certain person, (ii) a type of activity the user is conducting, selected from at least two different types of activities associated with different levels of stress, and/or (iii) a type of activity the user is about to conduct (e.g., within thirty minutes), selected from at least two different types of activities associated with different levels of stress.

In a third embodiment, the system includes another CAM that takes thermal measurements of a region on the forehead ($TH_F$) of the user, and the computer 445 detects a respiratory related attack based on $TH_{ROI}$ and $TH_F$. For example, $TH_{ROI}$ and $TH_F$ may be utilized to generate one or more of the feature values used to calculate the value indicative of the probability that the user is experiencing, or is about to experience, the respiratory-related attack. Optionally, the model 442 was trained based on a first set of $TH_{ROI}$ and $TH_F$ taken while the user experienced a respiratory-related attack, and a second set of $TH_{ROI}$ and $TH_F$ taken while the user did not experience a respiratory-related attack.

The system may optionally include a sensor 435 that takes measurements $m_{move}$ 450 that are indicative of movements of the user 420; the system further detects the physiological response based on $m_{move}$ 450. The sensor 435 may include one or more of the following sensors: a gyroscope and/or an accelerometer, an outward-facing visible-light camera (that feeds an image processing algorithm to detect movement from a series of images), a miniature radar (such as low-power radar operating in the range between 30 GHz and 3,000 GHz), a miniature active electro-optics distance measurement device (such as a miniature Lidar), and/or a triangulation wireless device (such as a GPS receiver). Optionally, the sensor 435 is physically coupled to the frame or belongs to a device carried by the user (e.g., a smartphone or a smartwatch).

In a first embodiment, the computer 445 may detect the respiratory-related attack if the value 447 of the respiratory parameter reaches a first threshold, while $m_{move}$ 450 do not reach a second threshold. In one example, reaching the first threshold indicates a high breathing rate, which may be considered too high for the user. Additionally, in this example, reaching the second threshold may mean that the user is conducting arduous physical activity. Thus, if the user is breathing too fast and this is not because of physical activity, then the computer 445 detects this as an occurrence of a respiratory-related attack (e.g., an asthma attack or a panic attack).

In a second embodiment, the computer 445 may generate feature values based on $m_{move}$ 450 in addition to $TH_{ROI}$ 443, and utilize an extended model to calculate, based on these feature values, a value indicative of the probability that the user is experiencing, or is about to experience, the respiratory related attack. In one example, the feature values used along with the extended model (which may be the model 442 or another model) include one or more of the following: (i) values comprised in $TH_{ROI}$ 443, (ii) values of a respiratory parameter of the user 420, which are generated based on $TH_{ROI}$ 443 (iii) values generated based on additional measurements of the user 420 (e.g., measurements of heart rate, heart rate variability, brainwave activity, galvanic skin response, muscle activity, and an extent of movement), (iv) measurements of the environment in which the user 420 was in while $TH_{ROI}$ 443 were taken, (v) indications of various occurrences which may be considered confounding factors (e.g., touching the face, thermal radiation directed at the face, or airflow directed at the face), and/or (vi) values indicative of movements of the user (which are based on $m_{move}$ 450).

The extended model is trained on samples generated from prior $m_{move}$ and $TH_{ROI}$, and corresponding labels indicating times of having the respiratory-related attack. The labels may come from various sources, such as measurements of the user (e.g., to detect respiratory distress), observations by a human and/or software, and/or the indications may be self-reported by the user. The samples used to train the extended model may be generated based on measurements taken over different days, and encompass measurements taken when the user was in different situations.

Usually the exhaled air warms up the skin below the nostrils, and during inhale the skin below the nostrils cools. This enables the system to identify the exhale based on measuring an increase in the temperature of the skin below the nostrils an inhale, and identify the inhale based on measuring a decrease in the temperature of the skin below the nostrils.

Synchronizing a physical effort with the breathing is highly recommended by therapists and sport instructors. For example, some elderly and/or unfit people can find it difficult to stand up and/or make other physical efforts because many of them do not exhale while making the effort, and/or do not synchronize the physical effort with their breathing. These people can benefit from a system that reminds them to exhale while making the effort, and/or helps them synchronize the physical effort with their breathing. As another example, in many kinds of physical activities it is highly recommended to exhale while making a physical effort and/or exhale during certain movements (such as exhale while bending down in Uttanasana).

In one embodiment, the computer 445 determines based on $m_{move}$ 450 and $TH_{ROI}$ 443 whether the user exhaled while making a physical effort above a predetermined threshold. Optionally, the computer receives a first indication that the user is making or is about to make the physical effort, commands a user interface (UI) to suggest the user to exhale while making the physical effort, and commands the UI to play a positive feedback in response to determining that the user managed to exhale while making the physical effort. Additionally, the computer may further command the UI to play an explanation why the user should try next time to exhale while making the physical effort in response to determining that the user did not exhale while making the physical effort.

FIG. 24a to FIG. 25c illustrate how the system described above may help train an elderly user to exhale during effort. In FIG. 24a the system identifies that the user inhaled rather than exhaled while getting up from a sitting position in a chair; the system alerts the user about this finding and suggests that next time the user should exhale while getting up. In FIG. 24b, the system identifies that the user exhaled at the correct time and commends the user on doing so. Examples of physical efforts include standing up, sitting down, manipulating with the hands an item that requires applying a significant force, defecating, dressing, leaning over, and/or lifting an item.

In FIG. 25a the system identifies that the user inhaled rather than exhaled while bending down to the dishwasher, and presents a thumbs-down signal (e.g., on the user's smartphone). In FIG. 25b the system identifies that the user exhaled while bending down to the dishwasher, and presents a thumbs-up signal. In FIG. 25c illustrates a smartphone app for counting the thumbs-up and thumbs-down signals identified during a day. The app may show various statistics, such as thumbs-up/thumbs-down during the past week, from start training with the app, according to locations the user is, while being with certain people, and/or organized according to types of exercises (such as a first counter for yoga, a second counter for housework, and a third counter for breathing during work time).

In one embodiment, the computer 445: (i) receives from a fitness app (also known as a personal trainer app) an indication that the user should exhale while making a movement, (ii) determines, based on $m_{move}$, when the user is making the movement, and (iii) determines, based on $TH_{ROI}$, whether the user exhaled while making the movement. Optionally, the computer commands the UI to (i) play a positive feedback in response to determining that the user managed to exhale while making the physical effort, and/or (ii) play an alert and/or an explanation why the user should try next time to exhale while making the physical effort in response to determining that the user did not exhale while making the physical effort. FIG. 26a illustrates a fitness app running on smartphone 196, which instructs the user to exhale while bending down. CAM coupled to eyeglasses frame 181 measures the user breathing and is utilized by the fitness app that helps the user to exhale correctly. FIG. 26b illustrates instructing the user to inhale while straightening up.

In another embodiment, the computer 445: (i) receives from a fitness app a certain number of breath cycles during which the user should perform a physical exercise, such as keeping a static yoga pose for a certain number of breath cycles, or riding a spin bike at a certain speed for a certain number of breath cycles, (ii) determines, based on $m_{move}$, when the user performs the physical exercise, and (iii) counts, based on $TH_{ROI}$, the number of breath cycles the user had while performing the physical exercise. Optionally, the computer commands the UI to play an instruction switch to another physical exercise responsive to detecting that the user performed the physical exercise for the certain number of breath cycles. Additionally or alternatively, the computer commands the UI to play a feedback that refers to the number of counted breath cycles responsive to detecting that the user performed the physical exercise for a number of breath cycles that is lower than the certain number of breath cycles. FIG. 27 illustrates a fitness app running on smartphone 197, which instructs the user to stay in a triangle pose for 8 breath cycles. CAM coupled to eyeglasses frame 181 measures the breathing and is utilized by the fitness app that calculates the breath cycles and counts the time to stay in the triangle pose according to the measured breath cycles.

The duration of exhaling and inhaling (denoted herein $t_{exhale}$ and $t_{inhale}$, respectively) can have various physiological effects. For example, for some users, breathing with prolonged inhales (relative to the exhales) can increase the possibility of suffering an asthma attack. In particular, keeping the duration of exhaling longer than the duration of inhaling (i.e., $t_{exhale}/t_{inhale} > 1$, and preferably $t_{exhale}/t_{inhale} \geq 2$) may provide many benefits, such as having a calming effect and relieving asthma symptoms. In one embodiment, a computer is further configured to calculate, based on $TH_{ROI}$, the ratio between exhale and inhale durations ($t_{exhale}/t_{inhale}$).

Many people are not aware of their breathing most of the time. These people can benefit from a system that is able to calculate $t_{exhale}/t_{inhale}$ and provide them with feedback when it is beneficial to increase the ratio. In one embodiment, a computer suggests the user, via the UI, to increase $t_{exhale}/t_{inhale}$ when it falls below a threshold. Optionally, the computer updates occasionally the calculation of $t_{exhale}/t_{inhale}$, and suggests to progressively increase $t_{exhale}/t_{inhale}$ at least until reaching a ratio of 1.5. Optionally, the computer stops suggesting to the user to increase $t_{exhale}/t_{inhale}$ responsive to identifying that $t_{exhale}/t_{inhale} \geq 2$. In another embodiment, the computer is configured to: (i) receive a first indication that the user's stress level reaches a first threshold, (ii) identify, based on $TH_{ROI}$, that the ratio between exhaling and inhaling durations ($t_{exhale}/t_{inhale}$) is below a second threshold that is below 1.5, and (iii) command the UI to suggest to the user to prolong the exhale until $t_{exhale}/t_{inhale}$ reaches a third threshold that is at least 1.5.

Figure 22:
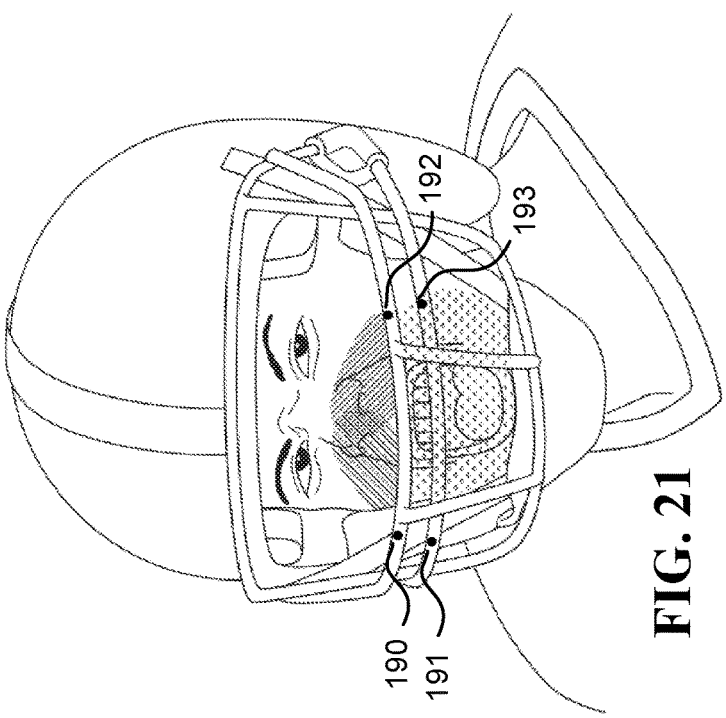
FIG. 22 illustrates a situation in which an alert is issued to a user when it is detected that the ratio the duration of exhaling and inhaling is too low.
Figure 30:
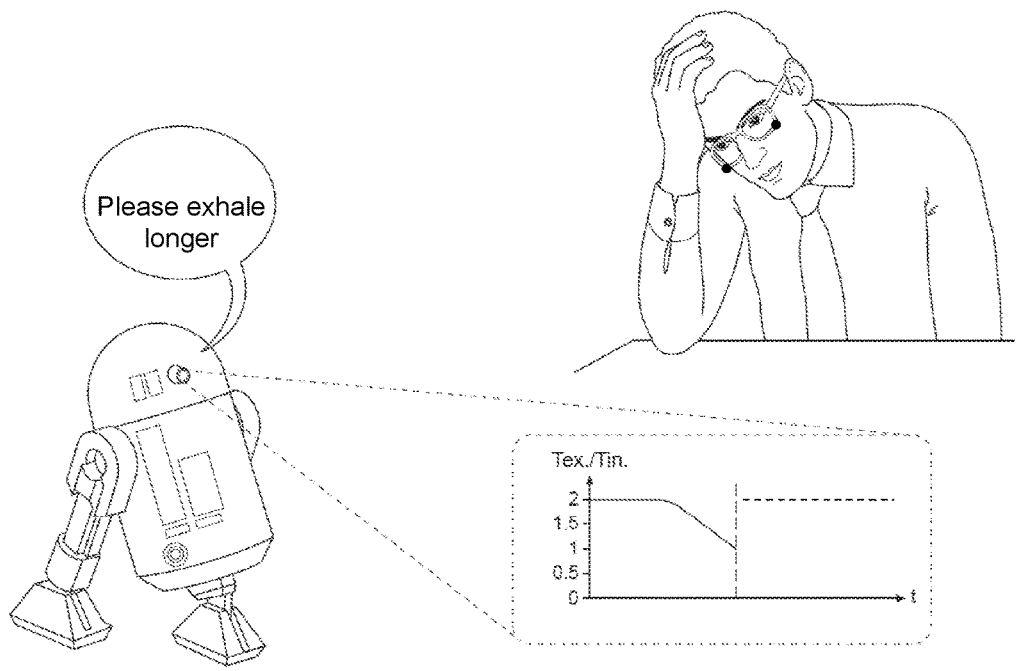
FIG. 30 illustrates a virtual robot that the user sees via augmented reality (AR), which urges the user to increase the ratio between the duration of the user's exhales and inhales.

FIG. 22 illustrates a situation in which an alert is issued to a user when it is detected that the ratio $t_{exhale}/t_{inhale}$ is too low. Another scenario in which such an alert may be issued to a user is illustrated in FIG. 30, which shows a virtual robot that the user sees via augmented reality (AR). The robot urges the user to increase the ratio between the duration of the user's exhales and inhales in order to alleviate the stress that builds up. Monitoring of respiratory parameters, and in particular, the ratio $t_{exhale}/t_{inhale}$ can help a user address a variety of respiratory-related symptoms, as described in the following examples.

Figure 31:
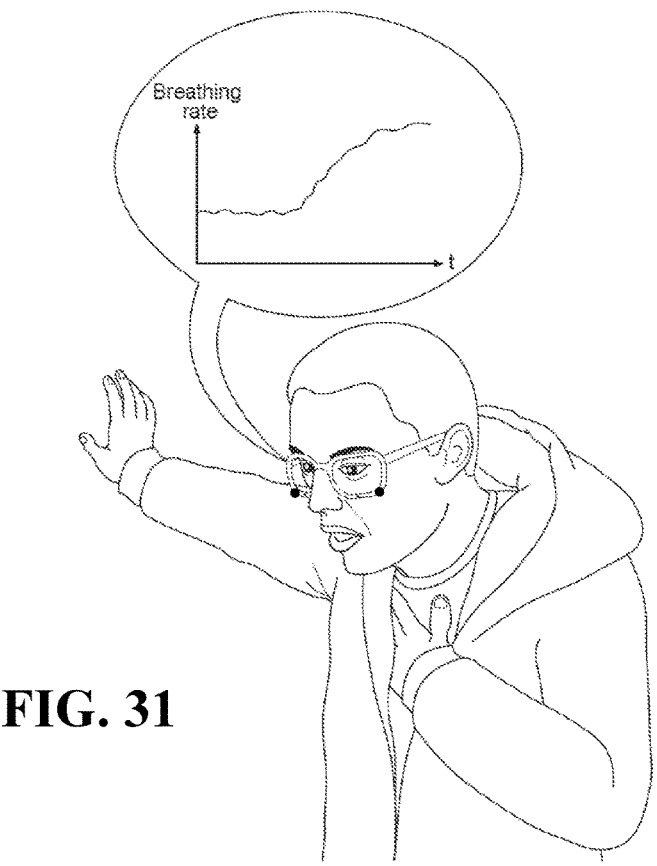
FIG. 31 illustrates an asthmatic patient who receives an alert that his breathing rate increased to an extent that often precedes an asthma attack.

Asthma attacks are related to a person's breathing Identifying certain changes in respiratory parameters, such as breathing rate above a predetermined threshold, can help a computer to detect an asthma attack based on the thermal measurements. Optionally, the computer utilizes a model, which was trained on previous measurements of the user taken while the user had an asthma attack, to detect the asthma attack based on the thermal measurements. FIG. 31 illustrates an asthmatic patient who receives an alert (e.g., via an augmented reality display) that his breathing rate increased to an extent that often precedes an asthma attack. In addition to the breathing rate, the computer may base its determination that an asthma attack is imminent on additional factors, such as sounds and/or movement analysis as described below.

In a first embodiment, the computer may receive recordings of the user obtained with a microphone. Such recordings may include sounds that can indicate that an asthma attack is imminent; these sounds may include: asthmatic breathing sounds, asthma wheezing, and/or coughing. Optionally, the computer analyzes the recordings to identify occurrences of one or more of the above sounds. Optionally, taking into account the recordings of the user can affect how the computer issues alerts regarding an imminent asthma attack. For example, a first alert provided to the user in response to identifying the increase in the user's breathing rate above the predetermined threshold without identifying at least one of the body sounds may be less intense than a second alert provided to the user in response to identifying both the increase in the user's breathing rate above the predetermined threshold and at least one of the body sounds. Optionally, in the example above, the first alert may not be issued to the user at all.

In a second embodiment, the computer may receive measurements obtained from a movement sensor worn by the user and configured to measure user movements. Some movements that may be measured and may be related to an asthma attack include: spasms, shivering, and/or sagittal plane movements indicative of one or more of asthma wheezing, coughing, and/or chest tightness. Optionally, the computer analyzes the measurements of the movement sensor to identify occurrences of one or more of the above movements. Optionally, considering the measured movements can affect how the computer issues alerts regarding an imminent asthma attack. For example, a first alert provided to the user in response to identifying an increase in the user's breathing rate above a predetermined threshold, without measuring a movement related to an asthma attack, is less intense than a second alert provided to the user in response to identifying the increase in the user's breathing rate above the predetermined threshold while measuring a movement related to an asthma attack.

In some embodiments, a first alert may be considered less intense than a second alert if it is less likely to draw the user's attention. For example, the first alert may not involve a sound effect or involve a low-volume effect, while the second alert may involve a sound effect (which may be louder than the first's). In another example, the first alert may involve a weaker visual cue than the second alert (or no visual cue at all). Examples of visual cues include flashing lights on a device or images brought to the foreground on a display. In still another example, the first alert is not provided to the user and therefore does not draw the user's attention (while the second alert is provided to the user).

In one embodiment, responsive to a determination that an asthma attack is imminent, the UI suggests the user to take a precaution, such as increasing $t_{exhale}/t_{inhale}$, preforming various breathing exercises (e.g., exercises that involve holding the breath), and/or taking medication (e.g., medication administered using an inhaler), in order to decrease or prevent the severity of the imminent asthma attack. Optionally, detecting the signs of an imminent asthma attack includes identifying an increase in the breathing rate above a predetermined threshold.

Stress is also related to a person's breathing. In one embodiment, a computer receives a first indication that the user's stress level reaches a threshold and receives a second indication (i) that the ratio between exhaling and inhaling durations is below 1.5 ($t_{exhale}/t_{inhale} < 1.5$), and/or (ii) that the user's breathing rate reached a predetermined threshold. Then the computer may command a UI to suggest the user to increase $t_{exhale}/t_{inhale}$ to at least 1.5. Optionally, the computer receives the first indication from a wearable device, calculates $t_{exhale}/t_{inhale}$ based on $TH_{ROI}$ (which is indicative of the exhale stream), and commands the UI to provide the user with an auditory and/or visual feedback indicative of the change in $t_{exhale}/t_{inhale}$ in response to the suggestion to increase the ratio. Optionally, the computer may command the UI to update the user about changes in the stress level in response to increasing $t_{exhale}/t_{inhale}$, and may provide positive reinforcement to help the user to maintain the required ratio at least until a certain improvement in the stress level is achieved.

Figure 23:
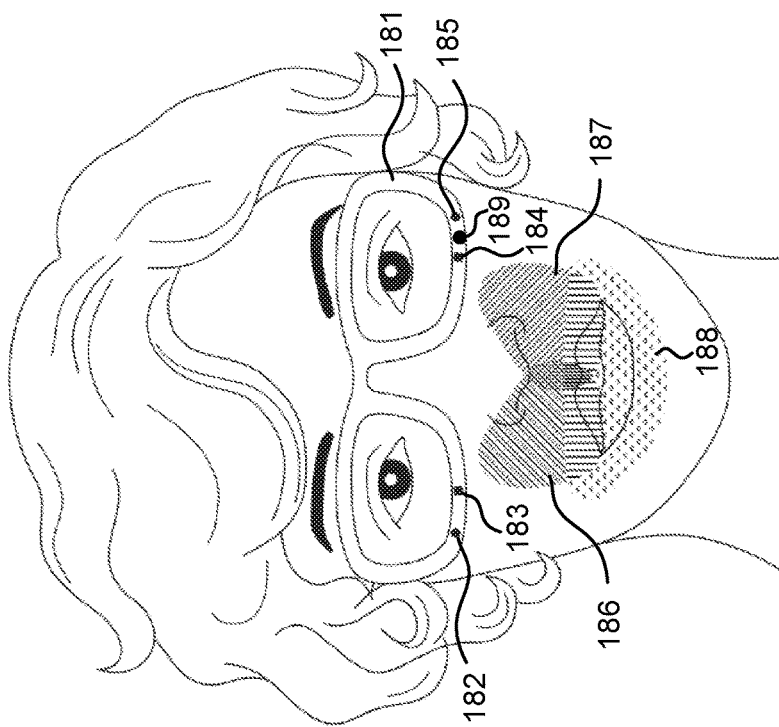
FIG. 23 illustrates an embodiment of a system that collects thermal measurements related to respiration, in which four CAMs are coupled to the bottom of an eyeglasses frame.

FIG. 23 illustrates one embodiment of a system configured to collect thermal measurements related to respiration, in which four inward-facing head-mounted thermal cameras (CAMs) are coupled to the bottom of an eyeglasses frame 181. CAMs 182 and 185 are used to take thermal measurements of regions on the right and left sides of the upper lip (186 and 187, respectively), and CAMs 183 and 184 are used to take thermal measurements of a region on the user's mouth 188 and/or a volume protruding out of the user's mouth. At least some of the ROIs may overlap, which is illustrated as vertical lines in the overlapping areas. Optionally, one or more of the CAMs includes a microbolometer focal-plane array (FPA) sensor or a thermopile FPA sensor.

In one embodiment, a computer detects whether the user is breathing mainly through the mouth or through the nose based on measurements taken by CAMs 182, 183, 184 and 185. Optionally, the system helps the user to prefer breathing through the nose instead of breathing through the mouth by notifying the user when he/she is breathing through the mouth, and/or by notifying the user that the ratio between mouth breathing and nose breathing reaches a predetermined threshold. In one embodiment, the computer detects whether the user is breathing mainly through the right nostril or through the left nostril based on measurements taken by CAMs 182 and 185.

The system may further include an inward-facing head-mounted visible-light camera 189 to take images (IM) of a region on the nose and/or mouth, which are used to calculate a respiratory parameter (e.g., detect whether the user is breathing mainly through the mouth or through the nose, detect the inhale duration, and/or detect the post-inhale pause duration). In one embodiment, one or more feature values may be generated based on IM. The feature values may be generated using various image processing techniques and represent various low-level image properties. Some examples of such features may include features generated using Gabor filters, local binary patterns and their derivatives, features generated using algorithms such as SIFT, SURF, and/or ORB, and features generated using PCA or LDA. The one or more feature values may be utilized in the calculation of the respiratory parameter in addition to feature values generated based on the thermal measurements.

Figure 28:
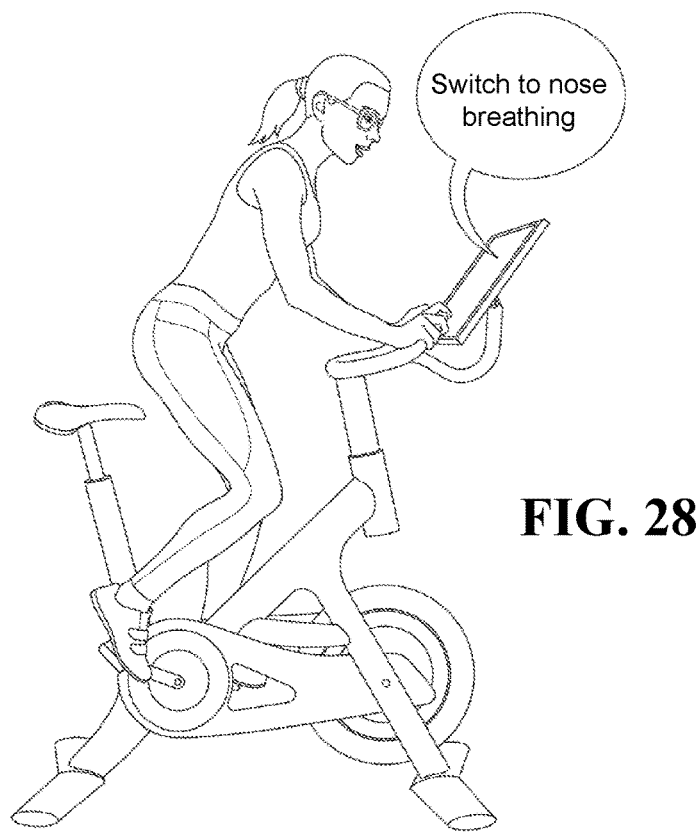
FIG. 28 illustrates notifying a user about mouth breathing and suggesting to breathe through the nose.
Figure 29:
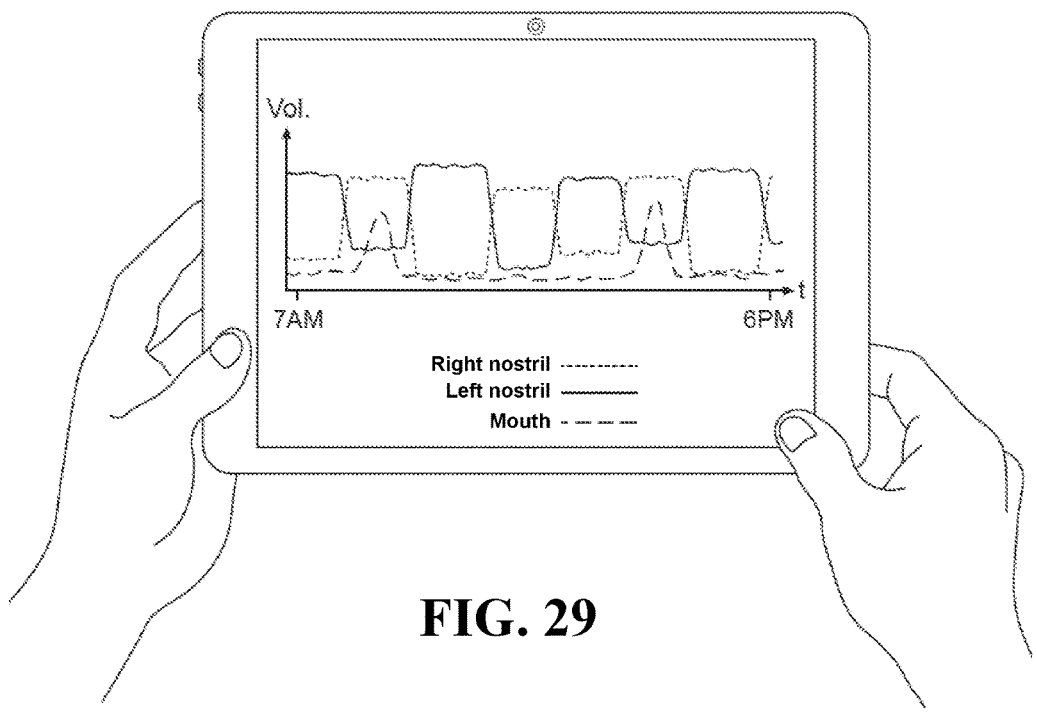
FIG. 29 illustrates an exemplary UI that shows statistics about the dominant nostril and mouth breathing during the day.

In one embodiment, the inward-facing head-mounted visible-light camera 189 takes images of a region on the user's mouth, and IM are indicative of whether the mouth is open or closed. A computer utilizes a model to detect, based on IM and $TH_{ROI}$ (such as the thermal measurements taken by at least one of CAMs 182-185), whether the user is breathing mainly through the mouth or through the nose. Optionally, the model was trained based on: a first set of $TH_{ROI}$ taken while IM was indicative that the mouth is open, and a second set of $TH_{ROI}$ taken while IM was indicative that the mouth is closed. Optionally, the system may help the user to prefer breathing through the nose instead of breathing through the mouth by notifying the user when he/she is breathing through the mouth, and/or by notifying the user that the ratio between mouth breathing and nose breathing reaches a predetermined threshold. FIG. 28 illustrates notifying the user that she breathes mainly through the mouth and should switch to breathing through the nose, while having a physical exercise such as spinning FIG. 29 illustrates an exemplary UI that shows statistics about the dominant nostril and mouth breathing during the day.

In one embodiment, the inward-facing head-mounted visible-light camera 189 takes images of a region on the nose, and the computer identifies an inhale (and/or differentiates between an inhale and a breathing pause that follows the inhale) based on image processing of IM to detect movements of the nose, especially at the edges of the nostrils, which are indicative of inhaling.

Figure 21:
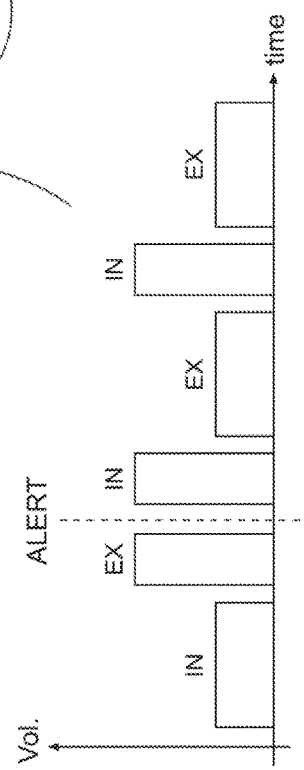
FIG. 21 illustrates an embodiment of a system that collects thermal measurements related to respiration, in which four inward-facing head-mounted thermal cameras (CAMs) are coupled to a football helmet.

FIG. 21 illustrates another embodiment of a system configured to collect thermal measurements related to respiration, in which four CAMs are coupled to a football helmet. CAMs 190 and 191 are used to take thermal measurements of regions on the right and left sides of the upper lip (appear as shaded regions on the users face), and CAMs 192 and 193 are used to take thermal measurements of a region on the user's mouth and/or a volume protruding out of the user's mouth. The illustrated CAMs are located outside of the exhale streams of the mouth and nostrils in order to maintain good measurement accuracy also when using thermal sensors such as thermopiles.

In some embodiments, the system further includes at least one in-the-ear earbud comprising a microphone to measure sounds inside the ear canal. A computer may identify an inhale based on analysis of the recordings from the earbud. Optionally, the inhale sounds measured by the earbud are stronger when the dominant nostril is the nostril closer to the ear in which the earbud is plugged in, compared to the inhale sounds measured by the earbud when the other nostril is the dominant nostril. Optionally, the computer detects whether the user is breathing mainly through the mouth or through the nose based on the thermal measurements and the sounds measured by the earbud. And then the system can help the user to prefer nasal breathing over mouth breathing by alerting the user when he/she breathes mainly through the mouth.

In some embodiments, the dominant nostril at a given time is the nostril through which most of the air is exhaled (with a closed mouth). Optionally, the dominant nostril is the nostril through which at least 70% of the air is exhaled. The different types of nostril dominance are illustrated in FIG. 32a to FIG. 32c. FIG. 32a is a schematic illustration of a left dominant nostril (note the significantly larger exhale stream from the left nostril). FIG. 32b is a schematic illustration of a right dominant nostril. And FIG. 32c is a schematic illustration of a balanced nasal breathing.

FIG. 33 is a schematic illustration of one embodiment of a system configured to identify the dominant nostril. The system includes at least one CAM 750, a computer 752, and an optional UI 754. CAM 750 may be similar to the CAMs in FIG. 23. CAM 750 takes thermal measurements of first and second ROIs below the right and left nostrils ($TH_{ROI1}$ and $TH_{ROI2}$, respectively) of the user. Optionally, each CAM does not occlude any of the user's mouth and nostrils. Optionally, each CAM is located less than 15 cm from the user's face and above the user's upper lip. Optionally, each CAM weighs below 10 g or below 2 g, and utilizes microbolometer or thermopile sensors. Optionally, each CAM includes multiple sensing elements that are configured to take $TH_{ROI1}$ and/or $TH_{ROI2}$. In one example, each CAM includes at least 6 sensing elements, and each of $TH_{ROI1}$ and $TH_{ROI2}$ is based on measurements of at least 3 sensing elements. Optionally, the system includes a frame to which CAM is physically coupled.

In one embodiment, the at least one CAM includes at least first and second thermal cameras (CAM1 and CAM2, respectively) that take $TH_{ROI1}$ and $TH_{ROI2}$, respectively, located less than 15 cm from the user's face. CAM1 is physically coupled to the right half of the frame and captures the exhale stream from the right nostril better than it captures the exhale stream from the left nostril, and CAM2 is physically coupled to the left half of the frame and captures the exhale stream from the left nostril better than it captures the exhale stream from the right nostril.

The at least one CAM may be used to capture thermal measurements of various ROIs. In one embodiment, the first region of interest ($ROI_1$) includes a region on the right side of the user's upper lip, and the second region of interest ($ROI_2$) includes a region on the left side of the user's upper lip. In another embodiment, $ROI_1$ includes a portion of the volume of the air below the right nostril where the exhale stream from the right nostril flows and $ROI_2$ includes a portion of the volume of the air below the left nostril where the exhale stream from the left nostril flows. In yet another embodiment, the at least one CAM may take thermal measurements of a region on the mouth and/or a volume protruding out of the mouth ($TH_{ROI3}$) of the user, which is indicative of the exhale stream from the mouth, and the computer identifies the dominant nostril also based on $TH_{ROI3}$. Optionally, the computer may utilize $TH_{ROI3}$ similarly to how it utilizes $TH_{ROI1}$ and $TH_{ROI2}$ to identify the dominant nostril (e.g., the computer may generate feature values based on $TH_{ROI3}$, as discussed below).

The computer identifies the dominant nostril based on $TH_{ROI1}$ and $TH_{ROI2}$ (and possibly other data such as $TH_{ROI3}$), which were taken during a certain duration. Optionally, the certain duration is longer than at least one of the following durations: a duration of one exhale, a duration of one or more breathing cycles, a half a minute, a minute, and five minutes.

In one embodiment, the computer utilizes a model to identify the dominant nostril. Optionally, the model was trained based on previous $TH_{ROI1}$, $TH_{ROI2}$, and indications indicative of which of the nostrils was dominant while the previous $TH_{ROI1}$ and $TH_{ROI2}$ were taken. In one example, the computer generates feature values based on $TH_{ROI1}$ and $TH_{ROI2}$ (and optionally $TH_{ROI3}$), and utilizes the model to calculate, based on the feature values, a value indicative of which of the nostrils is dominant.

In one embodiment, the computer identifies whether the user's breathing may be considered balanced breathing. Optionally, breathing is considered balanced breathing when the streams through the right and the left nostrils are essentially equal, such as when the extent of air exhaled through the left nostril is 40% to 60% of the total of the air exhaled through the nose. Balanced breathing of a normal healthy human usually lasts 1-4 minutes during the time of switching between the dominant nostrils. Optionally, the computer notifies the user when the user's breathing is balanced. Optionally, the computer suggests to the user, via a UI, to meditate during the balanced breathing The total time the different nostrils remain dominant may be indicative of various medical conditions. In one embodiment, when there is a significant imbalance of the daily total time of left nostril dominance compared to total time of right nostril dominance, and especially if this condition continues for two or more days (and is significantly different from the user's average statistics), it may be an indication of an approaching health problem. For example, when the total time of left nostril dominance is greater than the total time of right nostril dominance, the approaching problem may be more mentally related than physically related; and when the total time of right nostril dominance is greater than the total time of left nostril dominance, the approaching problem may be more physically related than mentally related. In another embodiment, a greater extent of left nostril dominance is related to digestion problems, inner gas, diarrhea, and male impotence; and a greater extent of right nostril dominance may be related to high blood pressure, acid reflux, and ulcers.

In one embodiment, the computer monitors nostril dominance over a certain period, and issues an alert when at least one of the following occurs: (i) a ratio between the total times of the right and left nostril dominance during the certain period reaches a threshold (e.g., the threshold may be below 0.3 or above 0.7) (ii) an average time to switch from right to left nostril dominance reaches a threshold (e.g., a threshold longer than 3 hours), and (iii) an average time to switch from left to right nostril dominance reaches a threshold.

The following are some examples of various applications in which the computer may utilize information about the dominant nostril, which is identified based on $TH_{ROI1}$ and $TH_{ROI2}$, in order to assist the user in various ways.

For some people, a certain dominant nostril may be associated with a higher frequency of having certain health problems, such as an asthma attack or a headache. Making a person aware of which nostril is more associated with the health problem can help the user to alleviate the health problem by switching the dominant nostril. Two examples of ways to switch the dominant nostril include: (i) to plug the current dominant nostril and breathe through the other nostril; and (ii) to lay on the side of the current dominant nostril (i.e., lying on the left side to switch from left to right dominant nostril, and vice versa). In one embodiment, the computer detects that the user is having an asthma attack, notifies the user about the current dominant nostril (which is associated with a higher frequency of asthma attacks), and suggests to switch the dominant nostril (to alleviate the asthma attack). In another embodiment, the computer detects the user has a headache, notifies the user about the current dominant nostril (which is associated with a higher frequency of headaches), and suggests to switch the dominant nostril.

Achieving balanced breathing may be a desired goal at some times. Biofeedback training may help extend the duration and/or increase the frequency at which one has balanced breathing. In one embodiment, the computer provides, via the UI, biofeedback for the user to achieve balanced breathing by playing a feedback. The feedback may be generated according to any suitable known method, such as normally playing the feedback when the breathing becomes more balanced, and stopping, rewinding, and/or dithering the feedback when the breathing becomes less balanced. Examples of feedbacks that may be used include playing a movie, running a video game, and/or playing sounds.

In a similar manner, biofeedback training may help the user to achieve a required breathing pattern, such as making a certain nostril dominant, or learning how to change the nostril from which most of the air is exhaled using thought and optionally without touching the nostrils. In one embodiment, the computer provides, via the UI, biofeedback for the user to achieve the required breathing pattern by playing a feedback. The feedback may be generated according to any suitable known method, such as playing a first sound when the use exhales more air from the right nostril than the left nostril, playing a second sound when the use exhales more air from the left nostril than the right nostril, and playing a third sound when the use exhales essentially the same from the right and left nostrils.

In one embodiment, the length of the exhale stream is considered as the distance from the nose at which the exhale stream can still be detected. For each person, there is a threshold that may change during the day and responsive to different situations. When the length of the exhale stream is below the threshold, it may indicate that the person is calm; and when the length of the exhale stream is longer than the threshold, it may indicate excitement. In general, the shorter the length of the exhale stream the less energy is invested in the breathing process and the less stress the person experiences. An exception may be arduous physical activity (which can increase the length of the exhale stream due to larger volumes of air that are breathed). In one embodiment, $TH_{ROT1}$ and $TH_{ROT2}$ are indicative of the length of the exhale stream, and the computer calculates level of excitement of the user based on the length of the exhale stream. Optionally, the longer the length, the higher the excitement/stress, and vice versa. Additionally, the relationship between the length of the exhale stream and the level of excitement may be a function of parameters such as the time in day, the dominant nostril, the user's mental state, the user's physiological state, the environmental air quality, and/or the temperature of the environment. In one example, the at least one CAM uses multiple sensing elements to take thermal measurements of regions located at different lengths below the nostrils. In this example, the larger the number of the sensing elements that detect the exhale stream, the longer the length of the exhale stream. Optionally, the amplitude of the temperature changes measured by the sensing elements is also used to estimate the length, shape, and/or uniformity of the exhale stream.

Ancient yoga texts teach that learning to extend the duration of the time gaps between inhaling and exhaling, and/or between exhaling and inhaling, increases life span. In one embodiment, the computer assists the user to extend the duration of the time gap between inhaling and exhaling by performing at least one of the following: (i) calculating the average time gap between inhaling and exhaling over a predetermined duration, and providing the calculation to the user via a user interface (UI), (ii) calculating the average time gap between inhaling and exhaling over a first predetermined duration, and reminding the user via the UI to practice extending the duration when the average time gap is shorter than a first predetermined threshold, and (iii) calculating the average time gap between inhaling and exhaling over a second predetermined duration, and encouraging the user via the UI when the average time gap reaches a second predetermined threshold. It is to be noted that to stop breathing after exhaling is considered more beneficial but also more dangerous, therefore the system may enable the user to select different required durations for stopping the breathing after inhaling and for stopping breathing after exhaling.

Typically, the dominant nostril switches sides throughout the day, with the duration between each switch varying, depending on the individual and other factors. Disruption of the typical nasal switching cycle may be indicative of physiological imbalance, emotional imbalance, and/or sickness. For example, slower switching of the dominant nostril may be, in some cases, a precursor of some diseases. In one embodiment, the computer learns the typical sequence of switching between dominant nostrils based on previous measurements of the user taken over more than a week, and issues an alert upon detecting an irregularity in the sequence of changes between the dominant nostrils. In one example, the irregularity involves a switching of the dominant nostril within a period of time that is shorter than a certain period typical for the user, such as shorter than forty minutes. In another example, the irregularity involves a lack of switching of the dominant nostril for a period that is greater than a certain period typical for the user, such as longer than three hours. In yet another example, the cycles of the dominant nostril may be described as a time series (e.g., stating for each minute a value indicative of the dominant nostril). In this example, the computer may have a record of previous time series of the user, acquired when the user was healthy, and the computer may compare the time series to one or more of the previous time series in order to determine whether a sufficiently similar match is found. A lack of such a similar match may be indicative of the irregularity.

The following is a discussion of the role of nostril dominance and other breathing aspects in Asian philosophy. According to Asian philosophy, and specifically the Vedas, all objects are made of the Five Great Elements, also known as the Classical elements, which include earth, water, fire, air, and space. The great elements represent types of energy, but they are related to the physical elements they are called after. During left or right nostril dominance, just one element is typically dominant in the body, and this is reflected in the form of the exhale stream (during balanced breath two elements may share dominance). When dominance in breathing is not forced, each of the five great elements in turn may become dominant and then cedes dominance to the next one. The normal order of dominance according to one text is: air, fire, earth, water, and space. The relative ratios of duration of dominance are: earth—5, water—4, fire—3, air—2, space—1. The dominant element affects breathing in two ways: the length of the exhale and the shape of the exhale stream (SHAPE). The average lengths and shapes of the outbreath are as follows according to one yoga textbook: earth—about 24 cm, straight out of the center of the nostril. Water—about 32 cm length, coming from the bottom of the nostril in a slight downward direction. Fire—8 cm, coming from the top of the nostril with an upward slant. Air—about 16 cm, coming from the external side of the nostril (left for the left nostril and right for the right nostril) with a slant outside. Space—very light and short breath from all parts of the nostril.

In one embodiment, the computer identifies, based on $TH_{ROT1}$ and $TH_{ROT2}$, the dominant element out of the five elements. Optionally, the computer monitors if relative durations and order of elements' dominance is regular, i.e. according to the order and duration ratios specified and optionally with approximate length as prescribed, or there is some irregularity. In one embodiment, irregularity may indicate a potential problem with the associated gland: for earth—ovaries or testes/prostate, water—adrenal, fire—intestines, air—none, space—thyroid and para-thyroid. In another embodiment, irregularity may indicate a potential mental and/or physiological problem(s).

If an element's dominance time (as evident from breathing characteristics) is too long, it may be balanced (reduced) by consuming appropriate food and/or drink. For example, air dominance can be reduced by consuming heavy oily food, fire dominance can be reduced by drinking water or by consuming water-absorbing food like buckwheat, and earth dominance can be reduced by eating light food with a lot of fiber.

If a dominant element is too weak (i.e., judging by breathing characteristics compared to the yardstick for that element, or comparing the SHAPE to a baseline SHAPE), it can be strengthened. For example, air dominance can be strengthened by active physical movement, fire dominance can be strengthened by breath-of-fire (from kundalini yoga), water dominance can be strengthened by drinking, earth can be strengthened by eating proteins and oily food, and space dominance can be strengthened by visualizing a picture that grows and shrinks in size.

As discussed above, the shape of the exhale stream (SHAPE) from the nostrils changes over time. With the at least one CAM it is possible, in some embodiments, to obtain measurements indicative of at least some of the different typical SHAPEs. A non-limiting reason for the system's ability to measure the different SHAPEs is that the exhale stream has a higher temperature than both the typical temperature of the environment and the typical temperature of the upper lip. As a result, the particles of the exhale stream emit at a higher power than both the environment and the upper lip, which enables CAM to measure the SHAPE over time.

As discussed above, different SHAPEs may be characterized by different 3D shape parameters (e.g., the angle from which the exhale stream blows from a nostril, the width of the exhale stream, the length of the exhale stream, and other parameters that are indicative of the 3D SHAPE). Additionally, different SHAPEs may be associated with different states of the user, such as different physiological and/or mental conditions the user may be in. In some embodiments, the computer calculates the SHAPE based on $TH_{ROf1}$ and $TH_{ROf2}$. Optionally, calculating the shape involves calculating values of one or more parameters that characterize the exhale stream's shape (e.g., parameters related to the 3D SHAPE). Optionally, calculating the SHAPE involves generating a reference pattern for the SHAPE. For example, the reference pattern may be a consensus image and/or heat map that is based on $TH_{ROf1}$ and $TH_{ROf2}$ taken over multiple breaths.

In other embodiments, the computer identifies a SHAPE based on $TH_{ROf1}$ and $TH_{ROf2}$. Optionally, the identified SHAPE belongs to a set that includes at least first and second SHAPEs, between which the computer differentiates. Optionally, the first and second SHAPEs are indicative of at least one of the following: two of the five great elements according to the Vedas, two different emotional states of the user, two different moods of the user, two different energetic levels of the user, and a healthy state of the user versus an unhealthy state of the user. In one example, the first SHAPE is indicative of a powerful alert energetic level, while the second SHAPE is indicative of a tired energetic level, and the computer uses this information to improve computerized interactions with the user.

The SHAPE may be related to the dominant nostril at the time. In one embodiment, the first SHAPE occurs more frequently when the right nostril is dominant, and the second SHAPE occurs more frequently when the left nostril is dominant. In another embodiment, both the first and the second SHAPEs occur more frequently when the right nostril is dominant.

In one example, differentiating between the first and second SHAPEs means that there are certain first $TH_{ROf1}$ and $TH_{ROf2}$ that the computer identifies as corresponding to the first SHAPE and not as corresponding to the second SHAPE, and there are certain second $TH_{ROf1}$ and $TH_{ROf2}$ that the computer identifies as corresponding to the second SHAPE and as not corresponding to the first SHAPE. In another example, differentiating between first and second SHAPEs means that there are certain third $TH_{ROf1}$ and $TH_{ROf2}$ that the computer identifies as having a higher affinity to the first SHAPE compared to their affinity to the second SHAPE, and there are certain fourth $TH_{ROf1}$ and $TH_{ROf2}$ that the computer identifies as having a higher affinity to the second SHAPE compared to their affinity to the first SHAPE.

In some embodiments, the SHAPE is identified by the computer based on $TH_{ROf1}$, $TH_{ROf2}$, and optionally other sources of data. Since the SHAPE does not typically change between consecutive breaths, detecting the shape of the exhale may be done based on multiple measurements of multiple exhales. Using such multiple measurements can increase the accuracy of the identification of the shape. In one example, the first and second SHAPEs are identified based on first and second sets of $TH_{ROf1}$ and $TH_{ROf2}$ taken during multiple exhales over first and second non-overlapping respective durations, each longer than a minute.

The computer may utilize different approaches to identify the SHAPE. In one embodiment, the computer may compare $TH_{ROf1}$ and $TH_{ROf2}$ to one or more reference patterns to determine whether $TH_{ROf1}$ and $TH_{ROf2}$ are similar to a reference pattern from among the one or more reference patterns. For example, if the similarity to a reference pattern reaches a threshold, the exhale stream measured with $TH_{ROf1}$ and $TH_{ROf2}$ may be identified as having the shape corresponding to the shape of the reference pattern. Determining whether $TH_{ROf1}$ and $TH_{ROf2}$ are similar to a reference pattern may be done using various image similarity functions, such as determining the distance between each pixel in the reference pattern and its counterpart in $TH_{ROf1}$ and $TH_{ROf2}$. One way this can be done is by converting $TH_{ROf1}$ and $TH_{ROf2}$ into a vector of pixel temperatures, and comparing it to a vector of the reference pattern (using some form of vector similarity metric like a dot product or the L2 norm).

The one or more reference patterns may be generated in different ways. In one embodiment, the one or more reference patterns are generated based on previous $TH_{ROf1}$ and $TH_{ROf2}$ of the user taken on different days. Optionally, the SHAPEs were known while previous $TH_{ROf1}$ and $TH_{ROf2}$ of the user taken. In one example, the SHAPE is associated with a state of the user at the time (e.g., relaxed vs. anxious). In another example, the SHAPE may be determined using an external thermal camera (which is not head-mounted). In yet another example, the SHAPE is determined by manual annotation. In one embodiment, the one or more reference patterns are generated based on previous $TH_{ROf1}$ and $TH_{ROf2}$ of one or more other users.

In some embodiments, the SHAPE may be discovered through clustering. Optionally, the computer may cluster sets of previous $TH_{ROf1}$ and $TH_{ROf2}$ of the user into clusters. Where sets of $TH_{ROf1}$ and $TH_{ROf2}$ in the same cluster are similar to each other and the exhale streams they measured are assumed to have the same shape. Thus, each of the clusters may be associated with a certain SHAPE to which it corresponds. In one example, the clusters include at least first and second clusters that correspond to the aforementioned first and second SHAPEs.

The computer may utilize a machine learning-based model to identify the SHAPE. In one embodiment, the computer generates feature values based on $TH_{ROf1}$ and $TH_{ROf2}$, and utilizes a model to classify $TH_{ROf1}$ and $TH_{ROf2}$ to a class corresponding to the SHAPE. Optionally, the class corresponds to the aforementioned first or second shapes. Optionally, the model is trained based on previous $TH_{ROf1}$ and $TH_{ROf2}$ of the user taken during different days.

In one embodiment, the computer receives an indication of the user's breathing rate, and uses this information along with the SHAPE at that time in order to suggest to the user to perform various activities and/or alert the user. Optionally, the indication of the user's breathing rate is calculated based on $TH_{ROI1}$ and $TH_{ROI2}$. In one example, the SHAPE is correlative with the state of the user, and different states combined with different breathing rates may have different meaning, which cause the computer to suggest different activities. The different activities may vary from different work/learning related activities to different physical activities to different treatments. In one example, the computer suggests to the user, via the UI, to perform a first activity in response to detecting that the breathing rate reached a threshold while identifying the first SHAPE. However, the computer suggest to the user to perform a second activity, which is different from the first activity, in response to detecting that the breathing rate reached the threshold while identifying the second SHAPE. In another example, the computer alerts the user, via the UI, in response to detecting that the breathing rate reached a threshold while identifying the first SHAPE, and the computer does not alert the user in response to detecting that the breathing rate reached the threshold while identifying the second SHAPE. In this example, the SHAPE may be correlated with the state of the user, and different states may be associated with different normal breathing rates. When the difference between the current breathing rate and the normal breathing rate (associated with the current SHAPE) reaches a threshold, the user may be in an abnormal state that warrants an alert.

In another embodiment, the computer configures a software agent that prioritizes activities for the user based on the identified SHAPE, such that a first activity is prioritized over a second activity responsive to identifying the first SHAPE, and the second activity is prioritized over the first activity responsive to identifying the second SHAPE. It is noted that the system may prioritize different activities for different SHAPEs also when the measured breathing rate and respiration volume are the same.

In still another embodiment, the computer learns a flow of typical changes between different SHAPEs based on previous measurements of the user, and issues an alert upon detecting an irregularity related to a flow of changes between the SHAPEs. For example, the irregularity may involve a new SHAPE, more frequent changes between SHAPEs, having certain SHAPEs for more or less time than usual, etc.

In yet another embodiment, the computer receives data about types of foods consumed by the user, stores the data in a memory, and finds correlations between the SHAPEs and the types of foods. These correlations may be used to make suggestions to the user. For example, the computer may suggest the user to eat a first type of food responsive to identifying the first SHAPE, and suggest the user to eat a second type of food responsive to identifying the second SHAPE. According to Ayurveda medicine, it is preferred to eat according to the three doshas and the five great elements. In times when the SHAPE is indicative of the dominant element (out of the five great elements), the computer may guide the user which types of food suit the identified dominant element, and/or may help the user to avoid inappropriate types of foods by identifying the types of food the user eats (and/or is about to eat), and alert the user when the identified food is inappropriate to the current dominant element (that was identified based on the SHAPE).

Data obtained from monitoring the dominant nostril can be utilized to make suggestions of activities for the user. FIG. 34 illustrates one embodiment of a system configured to suggest activities according to the dominant nostril. The system includes a sensor 451 for taking measurements 454 indicative of which of the user's nostrils is dominant at the time the measurements 454 were taken. Optionally, the sensor 451 is one or more thermal cameras, such as the thermal cameras illustrated in FIG. 23, however, as discussed below, other types of sensors may be utilized to take the measurements 454. The system also includes a computer 455 and optionally includes a UI 456.

The computer 455 predicts, based on the measurements 454, which of the user's nostrils will be the dominant nostril at a future time. Optionally, responsive to predicting that the right nostril will be dominant at the future time, the computer 455 suggests having at the future time a first activity, which is more suitable for a right dominant nostril than a second activity. Optionally, responsive to predicting that the left nostril will be dominant at the future time, the computer suggests having at the future time the second activity, which is more suitable for a left dominant nostril than the first activity. Optionally, the computer 455 suggests activities utilizing the UI 456. In one example, the first activity requires more verbal-analytical skills and less spatial skills compared to the second activity. In another example, the first activity requires more logic and/or locomotive skills compared to the second activity, and less empathy and/or imagination. In another example, the second activity requires more creativity and less physical effort compared to the first activity.

The suggestions of activities described above may be based on the premise that the dominant nostril is indicative of which of the user's brain hemispheres is more effective at performing activities that are associated with it. It is typically assumed that the left side of the user's brain is expected to be more effective at performing tasks when the right nostril is dominant (compared to when the left nostril is dominant). Conversely, the right side of the user's brain is expected to be more effective at performing tasks when the left nostril is dominant (compared to when the right nostril is dominant). The right hemisphere is usually believed to be better at expressive and creative tasks. Some of the abilities associated with the right hemisphere include recognizing faces, expressing emotions, music, reading emotions, color, images, intuition, and creativity. The left hemisphere is usually believed to be adept to tasks that involve logic, language, and analytical thinking. The left hemisphere is usually described as being better at language, logic, critical thinking, numbers, and reasoning. Thus, certain activities, which require certain skills that are associated with a certain hemisphere, may be more suitable to perform when one nostril is dominant compared to when the other nostril is dominant.

Additionally or alternatively, the suggestions of activities described above may be based on empirical data of the performances of the user and/or performances of other users. By analyzing the user's performances versus the dominant nostril (and optionally other parameters), and/or using big data analysis of the measured performances of many users versus their dominant nostril (and optionally other parameters), it is possible to identify a first set of activities that are statistically significantly more successfully achieved during right dominant nostril, a second set of activities that are statistically significantly more successfully achieved during left dominant nostril, and a third set of activities that are statistically significantly more successfully achieved during a balanced nasal breathing.

To predict the dominant nostril at the future time, the computer 455 relies on the measurements 454, which were taken prior to a current time, at which the prediction is made.

Optionally, the future time may be at least five minutes after the current time, at least thirty minutes after the current time, at least one hour after the current time, at least three hours after the current time, or at least six hours after the current time.

In one embodiment, the computer 455 utilizes the measurements 454 to determine when the dominant nostril last switched (before the current time), and uses this information to predict when it will switch next (possibly multiple times). Thus, the computer can extrapolate, based on the measurements 454, a timeline until the future time, indicating which nostril is dominant at different times until (and including) the future time. Optionally, information useful for determining the time line (such as the time each nostril remains dominant) may be based on the measurements 454 and/or previous measurements of the user taken with the sensor 451 during different days.

In another embodiment, the computer 455 predicts the dominant nostril at the future by generating feature values and utilizing a machine learning-based model to estimate the dominant nostril at the future time (e.g., left nostril dominance, right nostril dominance, or balanced breathing) Optionally, the feature values comprise one or more feature values describing aspects of the future time such as the time to which it corresponds (e.g., how much time ahead the future time is), the location the user is expected to be at the future time, and/or an activity the user is expected to partake at the future time. Optionally, the feature values may include one or more features values corresponding to a state of the user at an earlier time that precedes the future time, such as the user's dominant nostril (e.g., as determine based on the measurements 454), manipulation of the dominant nostril performed by the user recently, previous measurements of the user taken after the user manipulated the dominant nostril and/or practiced pranayama and/or listened to brainwave entrainment, an activity the user had during the earlier time, and/or values of physiological signals of the user at the earlier time. In one embodiment, the machine learning-based model is trained based on samples that include measurements 454 taken at certain earlier times and their corresponding dominant nostrils following certain durations after the certain earlier times.

When a first activity is suggested for the future time (over the second activity), it typically means that the first activity is to be preferred over the second activity. Optionally, to suggest having the first activity at the future time means that the computer schedules the first activity at the future time and does not schedule the second activity at the future time. Additionally or alternatively, to suggest having the first activity at the future time means that the computer 455 ranks the first activity at the future time higher than it ranks the second activity at the future time. Optionally, when the first activity is ranked higher than the second activity it means that the first activity is given a stronger recommendation than the second activity. For example, a stronger recommendation may involve the first activity being suggested by displaying it first on a list of suggested activities. In another example, a stronger recommendation may involve suggesting the first activity with a larger image, a more prominent visual effect, and/or a more noticeable auditory signal than the one used to suggest the second activity.

The computer 455 may utilize a determination of which nostril is dominant at the current time and/or a prediction of which nostril will be dominant at the future in order to assist the user in performing activities at suitable times. In a first embodiment, the computer 455 assists the user to spend more time eating certain types of food when the right nostril is dominant. Additionally or alternatively, the computer 455 further assists the user to spend less time eating the certain types of food when the left nostril is dominant. In one example, the computer 455 may assist the user by identifying that the user starts looking for food during left nostril dominance, and reminding the user that eating while the left nostril is dominant is probably due to emotional reasons. In another example, the computer 455 may arrange the user's schedule such that at least 60% of the occurrences of lunch and/or dinner are planned to a time when the right nostril is dominant. Optionally, the computer 455 recommends to the user to have the main meal of the day while the right nostril is dominant. In a second embodiment, the computer 455 assists the user to increase the time spent at the toilet defecating while the right nostril is dominant. Optionally, the computer 455 recommends to the user to spend less time at the toilet defecating while the left nostril is dominant. For example, the computer 455 may recommend to go on a bathroom break when the right nostril is dominant. Optionally, the computer 455 may assist the user to decrease defecating during times of left nostril dominance by reminding the user that it is preferred to defecate during right nostril dominance, especially when suffering from constipation. In a third embodiment, the activity involves creativity, such as creating art, and the computer 455 assists the user to spend more time on the creative activity when the left nostril is dominant.

It is recommended to perform some activities when the breathing through the nose is balanced. In one embodiment, the computer 455 identifies, based on the measurements 454, times in which the breathing through the nose is balanced, and suggests a third activity for those times. Optionally, the third activity is more suitable for balanced breathing compared to the first and second activities. Optionally, the third activity requires higher self-awareness compared to the first and second activities. For example, the third activity may include a spiritual practice (such as meditating or praying), while the first and second activities do not include spiritual practices.

Various hardware configurations may be utilized in different embodiments of the system configured to suggest activities according to the dominant nostril, in order to take the measurements 454 of the user.

In a first embodiment, the system includes a CAM that takes thermal measurements of a region below the user's nostrils (e.g., CAM 183 or CAM 184). In this embodiment, identifying the dominant nostril and/or whether the breathing is balanced may be done by the computer 455 based on signal processing of the thermal measurements taken by CAM.

In a second embodiment, the sensor 451 includes one or more implanted sensors located around the area of the nostrils. In this embodiment, identification of the dominant nostril and/or whether the breathing is balanced may be done based on signal processing of the measurements of the implanted sensors.

In a third embodiment, the sensor 451 includes right and left in-the-ear earbuds comprising microphones, configured to measure sounds inside the right and left ear canals; the computer 455 identifies the dominant nostril based on analysis of the recordings from the earbuds. For example, the computer 455 may identify the dominant nostril based on the assumption that the inhale sounds measured by the in-the-ear earbud in the dominant side are stronger than the inhale sounds measured by the in-the-ear earbud in the non-dominant side.

In a fourth embodiment, the system includes a frame configured to be worn on the user's head, and the sensor 451 comprises a visible-light camera; the visible-light camera is physically coupled to the frame, and takes images of a region on the user's nose. For example, the computer 455 may identify the dominant nostril based on analyzing the images of the nose by identifying movements of the nose, especially at the edges of the nostrils.

In a fifth embodiment, the sensor 451 includes thermistors that are in contact with the nostrils and/or the upper lip in order to take the measurements. Optionally, the dominant nostril may be identified based on signal processing of the thermistors' measurements.

In a sixth embodiment, the sensor 451 includes anemometers located inside the breathing streams of the nostrils in order to take the measurements. Optionally, the dominant nostril is identified based on signal processing of the anemometers' measurements.

In a seventh embodiment, the sensor 451 includes a non-wearable IR camera pointed to the area around the nostrils in order to take the measurements. Optionally, the dominant nostril is identified based on image processing of the measurements of the non-wearable IR camera.

The suggestions provided by the computer 455 may be done as part of various programs that may benefit the user. Optionally, the computer 455 provides functionality of at least one of the following programs: a virtual assistant (i.e., a software agent), a calendar management program, a priority management program, a project management program, a "to do" list program, a work schedule program, and a self-learning program.

Some embodiments of the system may involve notification of the user about which of the nostrils is dominant at a given time (e.g., via UI 456). Optionally, the notification involves providing a user with an indication (e.g., via sound and/or an image) when the dominant nostril changes and/or every certain period of time (e.g., every hour). Additionally or alternatively, notifying the user about which of the nostrils is dominant may involve utilizing different themes for UI 456. In one example, a first theme for UI 456 is utilized when the right nostril is the dominant nostril, and a second theme for UI 456 is utilized when the left nostril is the dominant nostril. Optionally, the first theme is more logical than the second theme (e.g., presenting data and/or suggestions involves providing more facts and/or detailed explanations), and the second theme is more emotional than the first theme (e.g., presenting data and/or suggestions includes more emotional phrases, abstract images, social-related data, and/or less factual information).

In one embodiment, the computer 455 is programmed to converse with the user according to at least first and second modes. The first mode is perceived by the user as more logical than the second mode, and the second mode is perceived by the user as more emotional than the first mode. The computer 455 uses, on average, the first mode more frequently than the second mode when the right nostril is the dominant nostril, and uses, on average, the second mode more frequently than the first mode when the left nostril is the dominant nostril. Examples of logical speech include sentences built around numbers and facts, while emotional speech includes sentences built around emotions and intuition.

The following is a description of steps involved in one embodiment of a method for suggesting activities according to the dominant nostril. The steps described below may be used by systems modeled according to FIG. 34, and may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform operations of the method.

In one embodiment, the method for alerting about stress includes at least the following steps: In Step 1, taking, utilizing a sensor, measurements of a user, which are indicative of the user's dominant nostril. In Step 2, predicting, based on the measurements, which of the user's nostrils will be the dominant nostril at a future time (that occurs after the measurements in Step 1 were taken). And In Step 3, responsive to predicting that the right nostril will be dominant at the future time, suggesting having at the future time a first activity, which is more suitable for a right dominant nostril than a second activity. Optionally, responsive to predicting that the left nostril will be dominant at the future time, this step involves suggesting having at the future time the second activity, which is more suitable for a left dominant nostril than the first activity. Optionally, the method further includes assisting the user to decrease eating certain types of food during left nostril dominance, and assisting the user to schedule the main meal of the day during right nostril dominance. Optionally, the method further includes learning the typical sequence of switching between dominant nostrils based on previous measurements of the user taken over more than a week, and alerting upon detecting an irregularity in the sequence of changes between the dominant nostrils.

In some embodiments, a system is configured to detect a physiological response based on respiratory parameters. Optionally, the physiological response is stress. Optionally, the respiratory parameters include the breathing rate and breathing rate variability (which is discussed further below).

The breathing rate variability (BRV) is a value that is indicative of the physiological phenomenon of variations between consecutive breaths, observed during a certain period of time (e.g., a minute). In a similar fashion to heart rate variability (HRV), which is the physiological phenomenon of variations between consecutive heartbeats, the extent of BRV can be indicative of various physiological phenomena, such as stress and/or physiological state.

In one embodiment, stress is detected based on thermal measurements of ROIs indicative of respiration performances, such as the mouth area, the upper lip area, and/or an air volume below the nostrils where the exhale from the nose flows. Optionally, $TH_{ROI}$ may be utilized to calculate various respiratory parameters, which include the breathing rate and/or the BRV.

The duration between successive breaths (such as the time between starting successive exhales) and/or breathing irregularity may be calculated using various methods, such as geometric methods, frequency-domain methods, and/or non-linear methods. The computer may calculate the BRV based on $TH_{ROI}$ taken during different periods of time, such as at least one minute long or at least 5 minutes long.

In one embodiment, the breathing rate variability (BRV) and the breathing rate (BR) are utilized by a computer in order to detect when the user is stressed. Optionally, elevated BRV in addition to elevated BR may serve as an indicator of stress. Optionally, elevated BRV, even when the BR is reduced, may serve as an indicator of stress. For example, the computer may calculate $BR_1$ and $BRV_1$ based on $TH_{ROI}$ taken during a first period, calculate $BR_2$ and $BRV_2$ based on $TH_{ROI}$ taken during a second following period, and determine that the user's stress level is higher at the second period relative to the first period because ($BRV_1 < BRV_2$), even though ($BR_1 > BR_2$).

In one embodiment, the computer calculates the stress level based on comparing BR and BRV to various thresholds that correspond to different stress levels. In one example, having a high BRV may lower the threshold on BR that is required in order to detect stress.

In another embodiment, the computer may utilize a machine learning-based model in order to detect the stress level. Optionally, the computer utilizes $TH_{ROI}$ to generate feature values indicative of the BR and/or the BRV, and the model was trained based on samples that each include feature values based on $TH_{ROI}$ and labels indicative of the user's stress level.

Figure 36:
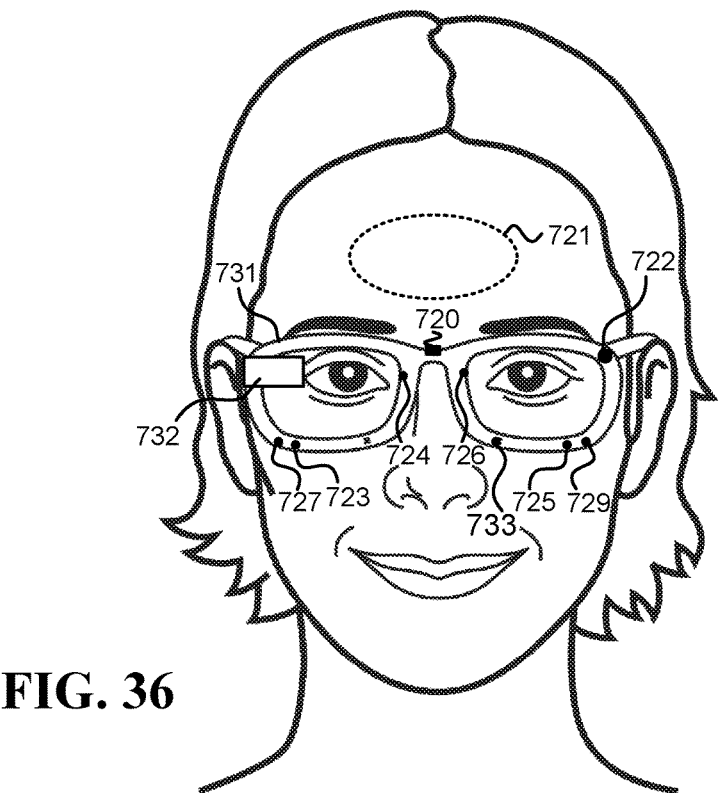
FIG. 36 illustrates an embodiment of a system configured to provide neurofeedback and/or breathing biofeedback.

FIG. 36 illustrates one embodiment of a system configured to provide neurofeedback (based on measurements of thermal camera 720) and/or breathing biofeedback (based on measurements of at least one of thermal cameras 723, 725, 727 and 729). Thermal camera 720 takes thermal measurements of a region on the forehead 721, thermal cameras 723 and 725 take thermal measurements of regions on the right and left sides of the upper lip, respectively, and thermal cameras 727 and 729 take thermal measurements of regions on the user's mouth and/or volumes protruding out of the user's mouth. The thermal cameras are physically coupled to a frame 731 that may be part of an augmented-realty system in which the visual feedback of the breathing biofeedback and/or neurofeedback is presented to the user via UI 732. The system may control the breathing biofeedback and/or neurofeedback session based on measurements taken by additional sensors, such as (i) sensor 722, which may be an outward-facing thermal camera that measures the intensity of infrared radiation directed at the face, and (ii) thermal cameras 724 and 726 that measure regions on the right and left periorbital areas, respectively.

In one embodiment, a system configured to provide a breathing biofeedback session for a user includes at least one inward-facing head-mounted thermal camera (CAM) and a user interface (UI). The at least one CAM takes thermal measurements of a region below the nostrils ($TH_{ROI}$), and $TH_{ROI}$ are indicative of the exhale stream. The UI provides feedback, calculated based on $TH_{ROI}$, as part of a breathing biofeedback session for the user. Optionally, the breathing biofeedback system may include additional elements such as a frame, a computer, additional sensors, and/or thermal cameras as described below.

The at least one CAM may have various configurations. In a first example, each of the at least one CAM is located less than 15 cm from the user's face and above the user's upper lip, and does not occlude any of the user's mouth and nostrils. Optionally, $TH_{ROI}$ include thermal measurements of at least first and second regions below right and left nostrils of the user. Optionally, the at least one CAM consists of a single CAM.

In a second example, the system further includes a frame worn on the user's head. $TH_{ROI}$ include thermal measurements of first and second regions below right and left nostrils ($TH_{ROI1}$ and $TH_{ROI2}$, respectively) of the user. The at least one CAM includes first and second thermal cameras for taking $TH_{ROI1}$ and $TH_{ROI2}$, respectively, which are located less than 15 cm from the user's face and above the nostrils. The first thermal camera is physically coupled to the right half of the frame and captures the exhale stream from the right nostril better than it captures the exhale stream from the left nostril, and the second thermal camera is physically coupled to the left half of the frame and captures the exhale stream from the left nostril better than it captures the exhale stream from the right nostril.

In a third example, $TH_{ROI}$ include thermal measurements of first, second and third regions on the user's face, which are indicative of exhale streams from the right nostril, the left nostril, and the mouth, respectively. The first and second regions are below the right and left nostrils, respectively, and the third region includes the mouth and/or a volume protruding out of the mouth.

The UI provides the feedback for the user during the breathing biofeedback session. The UI may also receive instructions from the user (e.g., verbal commands and/or menu selections) to control the session parameters, such as session duration, goal, and type of game to be played. The UI may include different types of hardware in different embodiments. Optionally, the UI includes a display that presents the user with video and/or 3D images, and/or a speaker that plays audio. Optionally, the UI is part of a device carried by the user. Optionally, the UI is part of a HMS to which the at least one CAM is coupled. Some examples of displays that may be used in some embodiments include a screen of a handheld device (e.g., a screen of a smartphone or a smartwatch), a screen of a head-mounted device (e.g., a screen of an augmented reality system or a virtual reality system), and a retinal display. In one embodiment, the UI may provide tactile feedback to the user (e.g., vibrations).

In some embodiments, at least some of the feedback presented to the user via the UI is intended to indicate to the user whether, and optionally to what extent, the user's breathing (as determined based on $TH_{ROI}$) is progressing towards a target pattern. The feedback may be designed to guide the user to breathe at his/her resonant frequency, which maximize amplitude of respiratory sinus arrhythmia and is in the range of 4.5 to 7.0 breaths/min.

The feedback may indicate the user's progress towards the target in different ways, which may involve visual indications, audio indications, and/or tactile indications. In one embodiment, the user is provided with a visual cue indicating the extent of the user's progress. For example, an object may change states and/or locations based on how close the user is to the target, such as an image of a car that moves forward as the user advances towards the target, and backwards if the user regresses. In one example, the feedback may include an audio-visual video of a fish that swims to the left when the exhale becomes smoother and stops swimming or even swims to the right when the exhale becomes less smooth. In another embodiment, the user is provided with an audio cue indicating the extent of the user's progress. For example, music played to the user may change its volume, tune, tone, and/or tempo based on whether the user is advancing towards the target or regressing from it, and/or different music pieces may be played when the user is at different rates of progression. In still another embodiment, the user is provided with a tactile cue indicating the extent of the user's progress. For example, a device worn and/or carried by the user may vibrate at different frequencies and/or at different strengths based on how far the user is from a goal of the session.

Breathing biofeedback requires closing the feedback loop on a signal that changes fast enough. Smoothness of the exhale stream, the shape, and/or the BRV have components that change at frequency above 2 Hz, which may be fast enough to act as the parameter on which the breathing biofeedback loop is closed. The feedback may be calculated and presented to the user at frequencies higher than 1 Hz, 2

Hz, 5 Hz, 10 Hz, 20 Hz and/or 40 Hz (which are all higher than the user's breathing rate).

The computer calculates, based on $TH_{ROI}$, a characteristic of the user's breathing, and generates the feedback based on the characteristic. Some breathing characteristics may be difficult to control, and often people are not even aware of them. However, breathing biofeedback can help the user achieve awareness and/or gain control over his/her breathing, and as a result improve the user's state.

One characteristic of the breathing, which the computer may take into account when controlling the breathing biofeedback session, is the smoothness of the exhale stream. Optionally, the smoothness of the exhale stream refers to a mathematical property of sets of values that include values of $TH_{ROI}$ taken over a period of time (e.g., values in a window that includes a portion of a breath, or even one or more breaths). The smoothness may be considered a property of graphs of the sets of values, and may represent how much of a variance there is in these values when compared to an average trend line that corresponds to the breathing. As discussed above, the smoothness may be calculated in various ways such as using Fourier transform and/or measuring a fit to a low order polynomial.

In one embodiment, the feedback is indicative of similarity between current smoothness of the exhale stream and target smoothness of the exhale stream. The current smoothness is calculated in real-time based on $TH_{ROI}$, and the target smoothness is calculated based on previous $TH_{ROI}$ of the user taken while the user was in a state considered better than the user's state while starting the breathing biofeedback session. Optionally, the similarity may be formulated as the distance between the current smoothness and the target smoothness.

In one embodiment, the feedback is indicative of at least one of the following: whether the smoothness is above or below a predetermined threshold, and whether the smoothness has increased or decreased since a previous feedback that was indicative of the smoothness. Optionally, the smoothness is calculated at frequency $\geq 4$ Hz, and the delay from detecting a change in the smoothness to updating the feedback provided to the user is $\leq 0.5$ second. As another option, the feedback may be indicative of whether the smoothness is above or below the predetermined threshold, and the user interface may update the feedback provided to the user at a rate $\geq 2$ Hz.

Another characteristic of the breathing, which the computer may take into account when controlling the breathing biofeedback session, is the shape of the exhale stream (SHAPE). Optionally, the SHAPE is described by one or more parameters that represent a 3D shape that bounds the exhale stream that flows from one or both of the nostrils. Optionally, the feedback is indicative of whether the SHAPE matches a predetermined shape, and/or whether the SHAPE has become more similar or less similar to the certain shape since a previous feedback that was indicative of the SHAPE. In one embodiment, the feedback is indicative of similarity between current shape of the exhale stream (SHAPE) and target SHAPE, wherein the current SHAPE is calculated in real-time based on $TH_{ROI}$, and the target SHAPE is calculated based on at least one of the following: (i) previous $TH_{ROI}$ of the user taken while the user was in a state considered better than the user's state while starting the breathing biofeedback session, and (ii) $TH_{ROI}$ of other users taken while the other users were in a state considered better than the user's state while starting the breathing biofeedback session.

Another characteristic of the breathing, which the computer may take into account when controlling the breathing biofeedback session, is the breathing rate variability (BRV), which is indicative of the variations between consecutive breaths. Optionally, the feedback may be indicative of similarity between current breathing rate variability (BRV) and a target BRV, wherein the current BRV is calculated in real-time based on $TH_{ROI}$, and the target BRV is calculated based on previous $TH_{ROI}$ of the user taken while the user was in a state considered better than the user's state while starting the breathing biofeedback session. Additionally or alternatively, the feedback may be indicative of whether the BRV is above or below a predetermined threshold, and/or whether a predetermined component of the BRV has increased or decreased since a previous feedback that was indicative of the BRV.

Similarly to how heart rate variability (HRV) is calculated, there are various computational approaches known in the art that may be used to calculate the BRV based on $TH_{ROI}$. In one embodiment, calculating the BRV involves identifying matching events in consecutive breaths (such as start exhaling, exhale peak, and/or inhale peak), and analyzing the variability between these matching events. In another embodiment, the user's breathing is represented as time series data from which low frequency and high frequency components of the integrated power spectrum within the time series signal are extracted using Fast Fourier Transform (FFT). A ratio of the low and high frequency of the integrated power spectrum within these components is computed and analysis of the dynamics of this ratio over time is used to estimate the BRV. In still another embodiment, the BRV may be determined using a machine learning-based model. The model may be trained on samples, each including feature values generated based on $TH_{ROI}$ taken during a certain period and a label indicative of the BRV during the certain period.

In some embodiments, the computer calculates a value indicative of similarity between a current $TH_{ROI}$ pattern and a previous $TH_{ROI}$ pattern of the user taken while the user was in a target state, and generates the feedback based on the similarity. Examples of $TH_{ROI}$ patterns include at least one of: a spatial pattern (e.g., a pattern in a thermal image received from a FPA sensor), a pattern in the time domain (e.g., a pattern detected in a time series of the thermal measurements), and a pattern in the frequency domain (e.g., a pattern detected in a Fourier transform of the thermal measurements).

Biofeedback sessions may have different target states in different embodiments. Generally, the purpose of a session is to bring the user's state during the biofeedback session (the "present state") to become more similar to a target state. In one embodiment, while the user was in the target state, one or more of the following were true: the user was healthier compared to the present state, the user was more relaxed compared to the present state, a stress level of the user was below a threshold, and the user was more concentrated compared to the present state. Additionally, the computer may receive an indication of a period during which the user was in the target state based on a report made by the user (the previous $TH_{ROI}$ pattern comprises $TH_{ROI}$ taken during the period), measurements of the user with a sensor other than CAM, semantic analysis of text written by the user, and/or analysis of the user's speech.

In another embodiment, the computer calculates a value indicative of similarity between current $TH_{ROI}$ and previous $TH_{ROI}$ of the user taken while the user was in a target state, and generates the feedback based on the similarity. The similarity may be calculated by comparing (i) a current value of a characteristic of the user's breathing, calculated based on $TH_{ROI}$, to (ii) a target value of the characteristic of the user's breathing, calculated based on the previous $TH_{ROI}$. Here, the feedback may be indicative of whether the current value of the characteristic of the user's breathing has become more similar or less similar to the target value of the characteristic of the user's breathing since a previous (related) feedback.

In still another embodiment, the computer compares a current set comprising feature values generated based on $TH_{ROI}$ to a target set comprising feature values generated based on previous $TH_{ROI}$ of the user, where the feature values are indicative of values of respiratory parameter(s).

In some embodiments, the system configured to provide a breathing biofeedback session receives indications of when the user is in the target state. Given such indications, the system may collect $TH_{ROI}$ taken during these times and utilize them in biofeedback sessions to steer the user towards the desired target (these collected $TH_{ROI}$ may be considered as the previous $TH_{ROI}$ mentioned above). There are various sources for the indications of when the user is in the certain target state. In one example, the user may report when he/she is in such a state (e.g., through an "app" or a comment made to a software agent). In another example, measurements of the user with one or more sensors other than CAM may provide indications that the user is in a certain physiological and/or emotional state that corresponds to the certain target state. In still another example, an indication of a period of time in which the user was in a certain target state may be derived from analysis of communications of the user, such as using semantic analysis of text written by the user, and/or analysis of the user's speech.

In some embodiments, the computer may utilize a machine learning-based model to determine whether the session is successful (or is expected to be) and/or to determine the user's progress in the breathing biofeedback session at a given time (e.g., the rate of improvement the user is displaying at that time and/or how close the user is to the session's target). Optionally, the computer generates feature values based on $TH_{ROI}$ (e.g., values of $TH_{ROI}$ and/or statistics of $TH_{ROI}$ taken over different periods during the session), and utilizes the model to calculate a value indicative of the progress and/or session success. Optionally, the model is trained on samples comprising feature values based on previously taken $TH_{ROI}$ and labels indicative of the success of the session and/or progress at the time those $TH_{ROI}$ were taken. Optionally, the samples may be generated based on previously taken $TH_{ROI}$ of the user. Additionally or alternatively, the samples may be generated based on previously taken $TH_{ROI}$ of other users. Optionally, the samples include samples generated based on $TH_{ROI}$ taken on different days, and/or while the measured user was in different situations.

The following method for providing a breathing biofeedback session may be used, in some embodiments, by systems modeled according to FIG. 36. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps: In Step 1, taking thermal measurements of a region below the nostrils ($TH_{ROI}$) of a user using at least one CAM worn on the user's head; $TH_{ROI}$ are indicative of the exhale stream. In Step 2, taking target $TH_{ROI}$ (TARGET) when the user is in a desired state, such as relaxed, healthy, happy, energized, and/or in a state of elevated concentration. In Step 3, taking current $TH_{ROI}$ (CURRENT) of the user. And in Step 4, providing the user with real-time feedback indicative of similarity between TARGET and CURRENT.

Generating the feedback may involve various calculations in different embodiments. For example, the method may include one or more of the following steps: (i) calculating target smoothness of the exhale stream based on TARGET and calculating current smoothness of the exhale stream based on CURRENT. Optionally, the feedback is indicative of similarity between the target smoothness and the current smoothness, (ii) calculating target shape of the exhale stream (SHAPE) based on TARGET and calculating current SHAPE based on CURRENT. Optionally, the feedback is indicative of similarity between the current SHAPE and the target SHAPE, and/or (iii) calculating target breathing rate variability (BRV) based on TARGET and calculating current BRV based on CURRENT. Optionally, BRV is indicative of variations between consecutive breaths, and the feedback is indicative of similarity between the current BRV and the target BRV.

In one embodiment, a system configured to select a state of a user includes at least one CAM and a computer. Each of the at least one CAM is worn on the user's head and takes thermal measurements of at least three regions below the nostrils ($TH_S$) of the user; wherein $TH_S$ are indicative of shape of the exhale stream (SHAPE). The computer (i) generates feature values based on $TH_S$, where the feature values are indicative of the SHAPE, and (ii) utilize a model to select the state of the user, from among potential states of the user, based on the feature values. Optionally, the model is utilized to calculate a value based on the feature values. In one example, the calculated value is indicative of which state the user is in, and the computer may calculate probabilities that the user is in each of the potential states, and select the state for which the probability is highest. In another example, the calculated value is an output of a classifier (e.g., a neural network-based classifier), which is indicative of the state the user is in.

In order for $TH_S$ to be indicative of the SHAPE, the at least one CAM needs to capture at least three regions from which the shape can be inferred. In a first example, the sensing elements of the at least one CAM include: (i) at least three vertical sensing elements pointed at different vertical positions below the nostrils where the exhale stream is expected to flow, and/or (ii) at least three horizontal sensing elements pointed at different horizontal positions below the nostrils where the exhale stream is expected to flow. Optionally, the larger the number of the vertical sensing elements that detect the exhale stream, the longer the length of the exhale stream, and the larger the number of the horizontal sensing elements that detect the exhale stream, the wider the exhale stream. Additionally, the amplitude of the temperature changes measured by the sensing elements may also be used to estimate the shape and/or uniformity of the exhale stream. It is noted that when a CAM, from among the at least one CAM, is located above the upper lip and pointed downwards, the vertical sensing elements (from the second example above) also provide data about the width of the exhale stream, and the horizontal sensing elements also provide data about the length of the exhale stream.

In a second example, the at least three regions from which the shape can be inferred are located on (i) at least two vertical positions below the nostrils having a distance above 5 mm between their centers, and (ii) at least two horizontal positions below the nostrils having a distance above 5 mm between their centers. Optionally, the at least three regions represent: (i) parameters of a 3D shape that confines the exhale stream, and $TH_S$ are the parameters' values, (ii) locations indicative of different lengths of the exhale stream (such as 8 cm, 16 cm, 24 cm, and 32 cm), and/or (iii) locations indicative of different angles characteristic of directions of some of the different SHAPES of the exhale stream (such as locations indicative of a difference of as at least 5°, 10°, or 25° between the directions of the different SHAPEs).

The potential states corresponding to the different SHAPEs may include various physiological and/or emotional states, and usually have to be learned and classified for each user because they depend on the user's physiological and emotional composition. Additionally, the potential states may include general states corresponding to either being healthy or being unhealthy. In some embodiments, at least some of the potential states may correspond to being in a state in which a certain physiological response is likely to occur in the near future (e.g., within the next thirty minutes). Thus, identifying that the user is in such a state can be used to alert regarding the certain physiological response which the user is expected to have in order for the user and/or some other party to take action to address it.

The feature values generated by the computer in order to calculate the SHAPE may include some of the various feature values described in this disclosure that are used to detect a physiological response. In particular, one or more of the feature values are generated based on $TH_S$, and may include raw and/or processed values collected by one or more sensing elements of the at least one CAM. Additionally or alternatively, these feature values may include feature values derived from analysis of $TH_S$ in order to determine various characteristics of the user's breathing. The feature values include at least one feature value indicative of the SHAPE. For example, the at least one feature value may describe properties of the thermal patterns of $TH_S$. Optionally, the feature values include additional feature values indicative of the breathing rate, breathing rate variability, and/or smoothness of the exhale stream.

The model used to select the user's state based on $TH_S$ (and optionally other sources of data) may be, in some embodiments, a machine learning-based model. Optionally, the model is trained based on samples comprising feature values generated based on previous on $TH_S$ taken when the user being measured was in a known state. Optionally, the previous $TH_S$ include thermal measurements of one or more other users (who are not the user whose state is selected based on $TH_S$); in this case, the model may be considered a general model. Optionally, the previous $TH_S$ include thermal measurements of the user whose state is selected based on $TH_S$; in this case, the model may be considered personalized for this user. Optionally, the previous $TH_S$ include thermal measurements taken during different days. Optionally, for each state from among the potential states, the samples include one or more samples that are generated based on $TH_S$ taken while the user being measured was in the state. Optionally, the model was trained based on: previous $TH_S$ taken while the user was in a first potential state from among the potential states, and other previous $TH_S$ taken while the user was in a second potential state from among the potential states. Optionally, the model was trained based on: previous $TH_S$ taken from users while the users were in a first potential state from among the potential states, and other previous $TH_S$ taken while the users were in a second potential state from among the potential states. Optionally, for the same breathing rate, respiration volume, and dominant nostril, the computer is configured to select different states when $TH_S$ are indicative of different SHAPEs that correspond to different potential states.

For each state from among the potential states, the samples include one or more samples that have a label corresponding to the state. The labels for the samples may be generated based on indications that may come from various sources. In one embodiment, a user whose $TH_S$ are used to generate a sample may provide indications about his/her state, such as by entering values via an app when having a headache or an anger attack. Additionally or alternatively, an observer of that user, which may be another person or a software agent, may provide indications about the user's state. For example, a parent may determine that certain behavior patterns of a child correspond to displaying symptomatic behavior of a certain state. In another embodiment, indications of the state of a user whose $TH_S$ are used to generate a sample may be determined based on measurements of physiological signals of the user, such as measurements of the heart rate, heart rate variability, galvanic skin response, and/or brain activity (e.g., using EEG).

In some embodiments, characteristics of the user's breathing may be indicative of a future state of the user (e.g., a state to which the user may be transitioning). Thus, certain changes in the characteristics of the user's breathing can be used to predict the future state. In these cases, some samples that include feature values generated based on $TH_S$ taken during a certain period may be assigned a label based on an indication corresponding to a future time (e.g., a label corresponding to the state of the user 15 or 30 minutes after the certain period). A model trained on such data may be used to predict the user's state at the future time and/or calculate a value indicative of the probability that the user will be in a certain state a certain amount of time into the future.

Given a set of samples that includes feature values generated based on $TH_S$ (and optionally the other sources of data) and labels indicative of the state, the model can be trained using various machine learning-based training algorithms. Optionally, the model may include various types of parameters, depending on the type of training algorithm utilized to generate the model. For example, the model may include parameters of one or more of the following: a regression model, a support vector machine, a neural network, a graphical model, a decision tree, a random forest, and other models of other types of machine learning classification and/or prediction approaches.

In some embodiments, a deep learning algorithm may be used to train the model. In one example, the model may include parameters describing multiple hidden layers of a neural network. In one embodiment, when $TH_S$ include measurements of multiple pixels, such as when the at least one CAM includes a FPA, the model may include a convolution neural network (CNN). In one example, a CNN may be utilized to identify certain patterns in the thermal images, such as patterns of temperatures in the region of the exhale stream that may be indicative a respiratory parameter, which involve aspects such as the location, direction, size, and/or shape of an exhale stream from the nose and/or mouth. In another example, determining a state of the user based on one characteristics of the user's breathing (e.g., various respiratory parameters), may be done based on multiple, possibly successive, thermal measurements. Optionally, estimating the state of the user may involve retaining state information about the one or more characteristics that is based on previous measurements. Optionally, the model may include parameters that describe an architecture that supports such a capability. In one example, the model may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

In order to generate a model suitable for identifying the state of the user in real-world day-to-day situations, in some embodiments, the samples used to train the model are based on thermal measurements (and optionally the other sources of data) taken while the user was in different situations, locations, and/or conducting different activities. For example, the model may be trained based on some sample based on previous thermal measurements taken while the user was indoors and other samples based on other previous thermal measurements taken while the user was outdoors. In another example, the model may be trained based on some sample based on some previous thermal measurements taken while the user was sitting and other samples based on other previous thermal measurements taken while the user was walking.

In one embodiment, the computer detects the SHAPE based on $TH_S$. Optionally, the detected SHAPE corresponds to a certain state of the user, and the computer bases the selection of the state on the detected SHAPE. Optionally, the computer generates one or more of the feature values used to select the state based on the detected SHAPE. For example, the one or more feature values may be indicative of various parameters of the SHAPE (e.g., parameters of a 3D geometrical body to which the SHAPE corresponds).

To detect the SHAPE the computer may utilize a model that was trained based on previous $TH_S$ of the user. Optionally, the previous $TH_S$ of the user were taken during different days. In one embodiment, the model includes one or more reference patterns generated based on the previous $TH_S$. Optionally, each reference pattern corresponds to a certain SHAPE, and is based on a subset of the previous $TH_S$ for which the certain SHAPE was identified. For example, identifying the certain SHAPE may be done using analysis of thermal images of the exhale stream obtained using an external thermal camera that is not head-mounted and/or by a human expert. In this embodiment, detecting the SHAPE may be done by comparing $TH_S$ to the one or more reference thermal patterns and determining whether there is a sufficiently high similarity between the thermal pattern of $TH_S$ and at least one of the one or more reference thermal patterns.

In another embodiment, the model may be a machine learning-based model that was trained on samples, with each sample comprising feature values generated based on a subset of the previous $TH_S$ (e.g., the subset includes previous $TH_S$ taken during a certain period), and a label representing the SHAPE corresponding to the subset of the previous $TH_S$. In one example, the feature values include values of temperatures of various sensing elements of the at least one CAM. In another example, the feature values may include low-level image properties obtained by applying various image processing techniques to the subset of the previous $TH_S$. In this embodiment, detecting the SHAPE may be done by generating feature values based on $TH_S$ and utilizing the model to calculate, based on the feature values, a value indicative of the SHAPE corresponding $TH_S$.

The SHAPE is a property that may be independent, at least to a certain extent, of other respiratory parameters. Thus, $TH_S$ taken at different times may have different SHAPEs detected, even if some other aspects of the breathing at those times are the same (as determined based on values of certain respiratory parameters). In one example, for the same breathing rate of the user, the computer detects a first SHAPE based on a first $TH_S$, and detects a second SHAPE based on a second $TH_S$. In this example, the first and second $TH_S$ have different thermal patterns, e.g., as determined using a similarity function between vector representations of the first and second $TH_S$ (which gives a similarity below a threshold). In another example, for the same breathing rate, respiration volume and dominant nostril, the computer detects a first SHAPE based on a first $TH_S$, and detects a second SHAPE based on a second $TH_S$ (where the first and second $TH_S$ have different thermal patterns).

In one embodiment, the system includes a frame worn on the user's head. Each of the at least one CAM is located less than 15 cm from the user's face and does not occlude any of the user's mouth and nostrils. The at least one CAM includes at least first and second inward-facing head-mounted thermal cameras (CAM1 and CAM2, respectively) that take $TH_{ROn}$ and $TH_{ROn2}$, respectively. CAM1 is physically coupled to the right half of the frame and captures the exhale stream from the right nostril better than it captures the exhale stream from the left nostril, and CAM2 is physically coupled to the left half of the frame and captures the exhale stream from the left nostril better than it captures the exhale stream from the right nostril. In another embodiment, the at least three regions below the nostrils include a first region on the right side of the user's upper lip, a second region on the left side of the user's upper lip, and a third region on the mouth of the user, where thermal measurements of the third region are indicative of the exhale stream from the user's mouth. In still another embodiment, the at least three regions below the nostrils include a first region comprising a portion of the volume of the air below the right nostril where the exhale stream from the right nostril flows, a second region comprising a portion of the volume of the air below the left nostril where the exhale stream from the left nostril flows, and a third region comprising a portion of a volume protruding out of the mouth where the exhale stream from the user's mouth flows.

In one embodiment, a system configured to present a user's state based on SHAPE, includes a CAM and a UI. The at least one CAM takes thermal measurements of at least three regions below the nostrils ($TH_S$) of the user, where $TH_S$ are indicative of SHAPE. The UI present the user's state based on $TH_S$. Optionally, for the same breathing rate, the UI presents different states for the user when $TH_S$ are indicative of different SHAPEs that correspond to different potential states. Optionally, each of the at least one CAM does not occlude any of the user's mouth and nostrils. Optionally, the system further includes a computer that generates feature values based on $TH_S$, and utilizes a model to select the state, from among potential states, based on the feature values.

The following method for selecting a state of a user may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps: In Step 1, taking thermal measurements of at least three regions below the nostrils ($TH_S$) of the user utilizing an inward-facing head-mounted thermal camera (CAM); wherein $TH_S$ are indicative of SHAPE. In Step 2, generating feature values based on $TH_S$, where the feature values are indicative of the SHAPE. And in Step 3, utilizing a model for selecting the state of the user, from among potential states of the user, based on the feature values.

Optionally, the method further includes selecting different states, for the same breathing rate, when $TH_S$ are indicative of different SHAPEs that correspond to different potential states. Optionally, the method further includes training the model based on: previous $TH_S$ taken while the user was in a first potential state from among the potential states, and other previous $TH_S$ taken while the user was in a second potential state from among the potential states.

Figure 37:
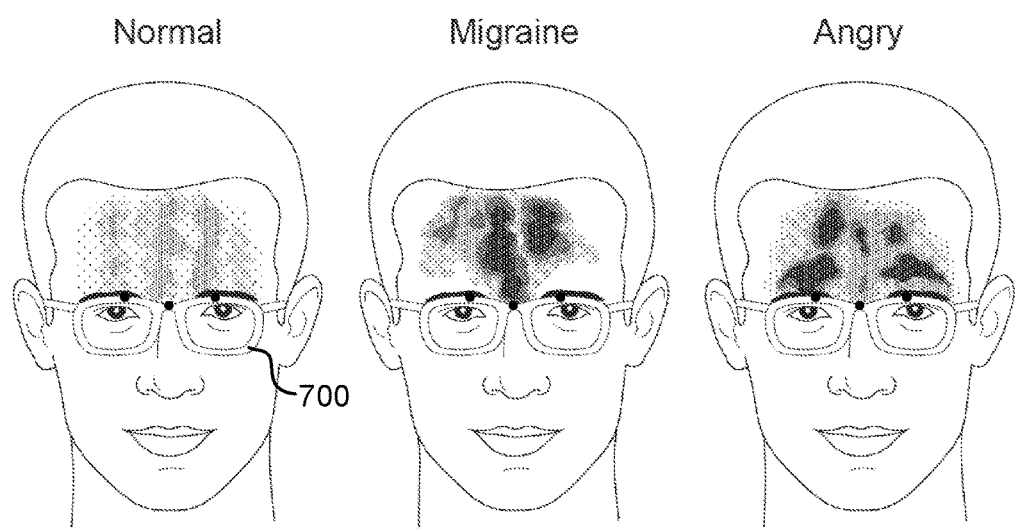
FIG. 37, FIG. 38 and FIG. 39 illustrate an embodiment of eyeglasses with head-mounted thermal cameras, which are able to differentiate between different states of the user based on thermal patterns of the forehead.
Figure 38:
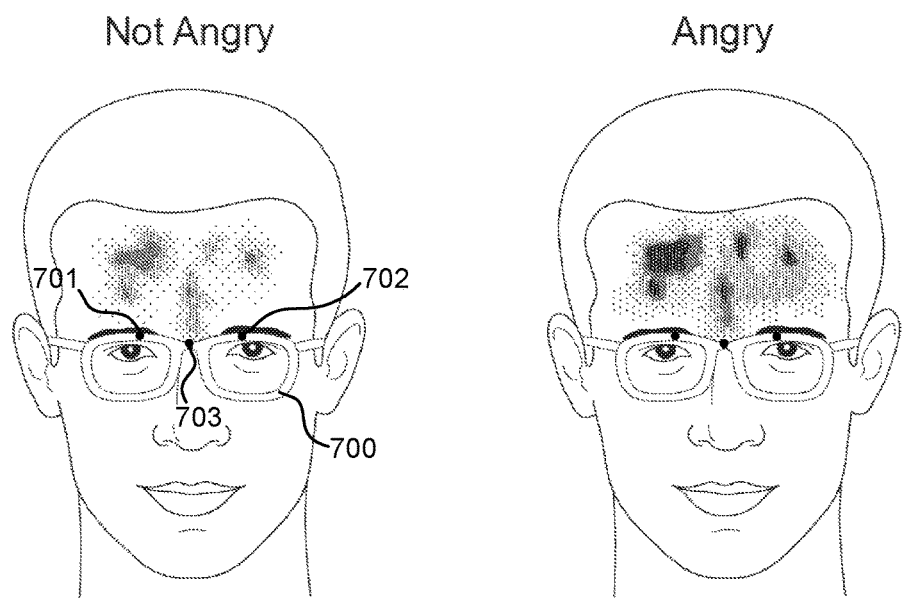
Figure 39:
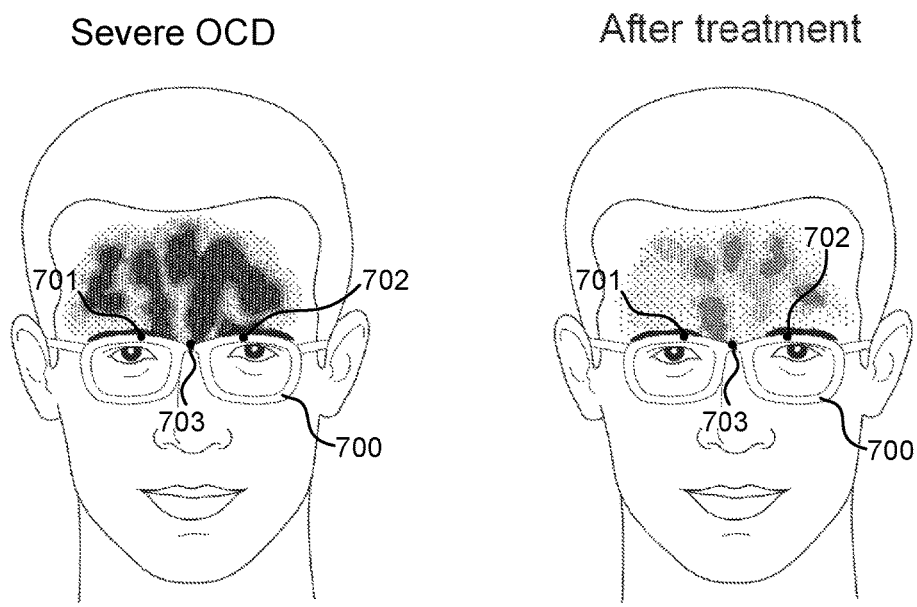

FIG. 37, FIG. 38, and FIG. 39 illustrate one embodiment of eyeglasses 700 with head-mounted thermal cameras, which are able to differentiate between different states of the user based on thermal patterns of the forehead. The illustrated system includes first and second CAMs (701, 702) mounted to the upper right and left portions of the eyeglasses frame, respectively, to take thermal measurements of the forehead. The system further include a sensor 703 mounted to the bridge, which may be utilized to take measurements ($m_{conf}$) indicative of an occurrence of one or more of the various confounding factors described herein. The CAMs forward the thermal measurements to a computer that may differentiate, based on the thermal measurements of the forehead, between normal and abnormal states of a user (which are illustrated as normal vs migraine vs angry in FIG. 37, and not angry vs angry in FIG. 38). The computer may further differentiate between extents of a condition, which is illustrated as severe OCD vs less severe OCD after a treatment in FIG. 39.

In one embodiment, a system configured to differentiate between normal and abnormal states, includes at least one CAM and a computer. The at least one CAM is worn on a user's head and takes thermal measurements of at least first and second regions on the right side of the forehead ($TH_{R1}$ and $TH_{R2}$, respectively) of the user. The at least one CAM further takes thermal measurements of at least third and fourth regions on the left side of the forehead ($TH_{L1}$ and $TH_{L2}$, respectively). The middles of the first and third regions are at least 1 cm above the middles of the second and fourth regions, respectively. Each of the least one CAM is located below the first and third regions, and does not occlude any portion of the first and third regions. Optionally, CAM also does not occlude the second and fourth regions. The computer determines, based on $TH_{R1}$, $TH_{R2}$, $TH_{L1}$, and $TH_{L2}$, whether the user is in a normal state or an abnormal state. Preferably, this embodiment assumes that the user's hair does not occlude the first, second, third and fourth regions on the forehead. Optionally, the at least one CAM includes a CAM that includes a sensor and a lens, and the sensor plane is tilted by more than 2° relative to the lens plane according to the Scheimpflug principle in order to capture sharper images by the CAM, when at least one CAM is worn by the user. Here, the lens plane refers to a plane that is perpendicular to the optical axis of the lens, which may include one or more lenses.

In one embodiment, the at least one CAM includes at least first and second inward-facing head-mounted thermal cameras (CAM1 and CAM2, respectively) located to the right and to the left of the vertical symmetry axis that divides the user's face, respectively (i.e., the axis the goes down the center of the user's forehead and nose). CAM1 is configured to take $TH_{R1}$ and $TH_{R2}$, and CAM2 is configured to take $TH_{L1}$ and $TH_{L2}$. Optionally, CAM1 and CAM2 are located at least 1 cm from each other. In one example, CAM1 and CAM2 are 701 and 702 that are illustrated in FIG. 38. Being able to detect a pattern on the forehead may involve utilization of multiple sensing elements (pixels) by each of CAM1 and CAM2. Optionally, each of CAM1 and CAM2 weighs below 10 g, is located less than 10 cm from the user's face, and includes microbolometer or thermopile sensor with at least 6 sensing elements. Optionally, CAM1 includes at least two multi-pixel thermal cameras, one for taking measurements of the first region, and another one for taking measurements of the second region; CAM2 also includes at least two multi-pixel thermal cameras, one for taking measurements of the third region, and another one for taking measurements of the fourth region.

The computer determines, based on $TH_{R1}$, $TH_{R2}$, $TH_{L1}$, and $TH_{L2}$, whether the user is in a normal state or an abnormal state. In one embodiment, the state of the user is determined by comparing $TH_{R1}$, $TH_{R2}$, $TH_{L1}$, and $TH_{L2}$ to reference thermal patterns of the forehead that include at least one reference thermal pattern that corresponds to the normal state and at least one reference thermal pattern that corresponds to the abnormal state. Optionally, a reference thermal pattern is determined from previous $TH_{R1}$, $TH_{R2}$, $TH_{L1}$, and $TH_{L2}$ of the user, taken while the user was in a certain state corresponding to the reference thermal pattern (e.g., normal or abnormal states). Determining whether $TH_{R1}$, $TH_{R2}$, $TH_{L1}$, and $TH_{L2}$, are similar to a reference thermal pattern may be done using various image similarity functions, such as determining the distance between each pixel in the reference thermal pattern and its counterpart in $TH_{R1}$, $TH_{R2}$, $TH_{L1}$, or $TH_{L2}$. One way this can be done is by converting $TH_{R1}$, $TH_{R2}$, $TH_{L1}$, or $TH_{L2}$ into a vector of pixel temperatures, and comparing it to a vector of the reference thermal pattern (using some form of vector similarity metric like a dot product or the L2 norm). Optionally, if the similarity reaches a threshold, the user is considered to be in the state to which the reference thermal pattern corresponds.

In another embodiment, the computer determines that the user is in a certain state (e.g., normal or abnormal) by utilizing a model to calculate, based on feature values generated from $TH_{R1}$, $TH_{R2}$, $TH_{L1}$, and $TH_{L2}$, a value indicative of the extent to which the user is in the certain state. Optionally, the model is trained based on samples, each comprising feature values generated based on previous $TH_{R1}$, $TH_{R2}$, $TH_{L1}$, and $TH_{L2}$ of the user, taken while the user was in the certain state. In some embodiments, determining whether the user is in a certain state involves determining that $TH_{R1}$, $TH_{R2}$, $TH_{L1}$, and $TH_{L2}$ taken during at least a certain period of time (e.g., at least ten seconds, at least one minute, or at least ten minutes) are similar to a reference thermal pattern that corresponds to the certain state.

Being in a normal/abnormal state may correspond to different behavioral and/or physiological responses. In one embodiment, the abnormal state involves the user displaying symptoms of one or more of the following: an anger attack, Attention Deficit Disorder (ADD), and Attention Deficit Hyperactivity Disorder (ADHD). In this embodiment, being in the normal state refers to usual behavior of the user that does not involve displaying said symptoms. In another embodiment, when the user is in the abnormal state, the user will display within a predetermined duration (e.g., shorter than an hour), with a probability above a predetermined threshold, symptoms of one or more of the following: anger, ADD, and ADHD. In this embodiment, when the user is in the normal state, the user will display the symptoms within the predetermined duration with a probability below the predetermined threshold. In yet another embodiment, when the user is in the abnormal state the user suffers from a headache, and when the user is in the normal state, the user does not suffer from a headache. In still another embodiment, the abnormal state refers to times in which the user has a higher level of concentration compared to the normal state that refers to time in which the user has a usual level of concentration. Although the thermal patterns of the forehead are usually specific to the user, they are usually repetitive, and thus the system may able to learn some thermal patterns of the user that correspond to various states.

Touching the forehead can change the forehead's thermal pattern, even though the user's state did not actually change. Optionally, the system further includes a sensor configured to provide an indication indicative of whether the user touches the forehead. Although the touch is expected to influence thermal readings from the touched area, the computer may continue to operate, for a predetermined duration, according to a state identified shortly (e.g., 1-20 sec) before receiving the indication, even if it identifies a different state shortly (e.g., less than 10, 20, 30, or 60 sec) after receiving the indication. In one example, the sensor is a visible-light camera, and the computer uses image processing to determine whether the user touched the forehead and/or for how long.

The computer may alert the user responsive to identifying an irregularity in $TH_{R1}$, $TH_{R2}$, $TH_{L1}$, and $TH_{L2}$, which does not result from interference, such as touching the forehead. For example, the irregularity may involve a previously unobserved thermal pattern of the forehead. Optionally, the user may be questioned in order to determine if there is a medical reason for the irregularity, such as a stroke or dehydration, in which case medical assistance may be offered, e.g., by summoning medical personnel to the user's location. Optionally, the computer alerts the user when identifying that the user is in an abnormal state associated with antisocial behavior (e.g., an anger attack).

Additional thermal cameras may be utilized to take thermal measurements that may be used to detect the user's state. For example, the system may include at least one additional CAM for taking thermal measurements of regions on the nose and below the nostrils ($TH_{ROI3}$ and $TH_{ROI4}$, respectively) of the user. Optionally, the additional CAM weighs below 10 g, is physically coupled to a frame worn on the user's head, and is located less than 15 cm from the face. Optionally, the computer determines the user's state also based on $TH_{ROI3}$ and $TH_{ROI4}$. Optionally, the computer (i) generates feature values based on $TH_{R1}$, $TH_{R2}$, $TH_{L1}$, $TH_{L2}$, $TH_{ROI3}$, and $TH_{ROI4}$, and (ii) utilizes a model to determine the user's state based on the feature values. Optionally, the model was trained based on a first set of previous $TH_{R1}$, $TH_{R2}$, $TH_{L1}$, $TH_{L2}$, $TH_{ROI3}$, and $TH_{ROI4}$ taken while the user was in the normal state and a second set of previous $TH_{R1}$, $TH_{R2}$, $TH_{L1}$, $TH_{L2}$, $TH_{ROI3}$, and $TH_{ROI4}$ taken while the user was in the abnormal state.

In another example, the system may include another CAM for taking thermal measurements of a region on the periorbital area ($TH_{ROI3}$) of the user. Optionally, the computer determines the state of the user also based on $TH_{ROI3}$. Optionally, the computer is further configured to: (i) generate feature values based on $TH_{R1}$, $TH_{R2}$, $TH_{L1}$, $TH_{L2}$, and $TH_{ROI3}$, and (ii) utilize a model to determine the user's state based on the feature values. Optionally, the model was trained based on a first set of previous $TH_{R1}$, $TH_{R2}$, $TH_{L1}$, $TH_{L2}$, and $TH_{ROI3}$ taken while the user was in the normal state and a second set of previous $TH_{R1}$, $TH_{R2}$, $TH_{L1}$, $TH_{L2}$, and $TH_{ROI3}$ taken while the user was in the abnormal state.

Determining the user's state based on $TH_{R1}$, $TH_{R2}$, $TH_{L1}$, and $TH_{L2}$ (and optionally other sources of data) may be done using a machine learning-based model. Optionally, the model is trained based on samples comprising feature values generated based on previous $TH_{R1}$, $TH_{R2}$, $TH_{L1}$, and $TH_{L2}$ taken when the user was in a known state (e.g., for different times it was known whether the user was in the normal or abnormal state). Optionally, the user may provide indications about his/her state, such as by entering values via an app when having a headache or an anger attack. Additionally or alternatively, an observer of the user, which may be another person or a software agent, may provide the indications about the user's state. For example, a parent may determine that certain behavior patterns of a child correspond to displaying symptomatic behavior of ADHD. In another example, indications of the state of the user may be determined based on measurements of physiological signals of the user, such as measurements of the heart rate, heart rate variability, breathing rate, galvanic skin response, and/or brain activity (e.g., using EEG).

In some embodiments, one or more of the feature values in the samples may be based on other sources of data (different from $TH_{R1}$, $TH_{R2}$, $TH_{L1}$, and $TH_{L2}$). These may include additional thermal cameras, additional physiological measurements of the user, and/or measurements of the environment in which the user was while the measurements were taken. In one example, at least some of the feature values used in samples include additional physiological measurements indicative of one or more of the following signals of the user: heart rate, heart rate variability, brainwave activity, galvanic skin response, muscle activity, and extent of movement. In another example, at least some of the feature values used in samples include measurements of the environment that are indicative of one or more of the following values of the environment in which the user was in: temperature, humidity level, noise level, air quality, wind speed, and infrared radiation level.

Given a set of samples comprising feature values generated based on $TH_{R1}$, $TH_{R2}$, $TH_{L1}$, and $TH_{L2}$ (and optionally the other sources of data) and labels generated based on the indications, the model can be trained using various machine learning-based training algorithms. Optionally, the model is utilized by a classifier that classifies the user's state (e.g., normal/abnormal) based on feature values generated based on $TH_{R1}$, $TH_{R2}$, $TH_{L1}$, and $TH_{L2}$ (and optionally the other sources). Optionally, the model may include various types of parameters, depending on the type of training algorithm utilized to generate the model. For example, the model may include parameters of one or more of the following: a regression model, a support vector machine, a neural network, a graphical model, a decision tree, a random forest, and other models of other types of machine learning classification and/or prediction approaches.

In some embodiments, the model is trained utilizing deep learning algorithms. Optionally, the model includes parameters describing multiple hidden layers of a neural network. Optionally, the model includes a convolution neural network (CNN), which is useful for identifying certain patterns in the thermal images, such as patterns of temperatures on the forehead. Optionally, the model may be utilized to identify a progression of a state of the user (e.g., a gradual forming of a certain thermal pattern on the forehead). In such cases, the model may include parameters that describe an architecture that supports a capability of retaining state information. In one example, the model may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

In order to generate a model suitable for identifying the state of the user in real-world day-to-day situations, in some embodiments, the samples used to train the model are based on thermal measurements (and optionally the other sources of data) taken while the user was in different situations, locations, and/or conducting different activities. In a first example, the model may be trained based on a first set of previous thermal measurements taken while the user was indoors and in the normal state, a second set of previous thermal measurements taken while the user was indoors and in the abnormal state, a third set of previous thermal measurements taken while the user was outdoors and in the normal state, and a fourth set of previous thermal measurements taken while the user was outdoors and in the abnormal state. In a second example, the model may be trained based on a first set of previous thermal measurements taken while the user was sitting and in the normal state, a second set of previous thermal measurements taken while the user was sitting and in the abnormal state, a third set of previous thermal measurements taken while the user was standing and/or moving around and in the normal state, and a fourth set of previous thermal measurements taken while the user was standing and/or moving around and in the abnormal state. Usually the movements while standing and/or moving around, and especially when walking or running, are greater compared to the movement while sitting; therefore, a model trained on samples taken during both sitting and standing and/or moving around is expected to perform better compared to a model trained on samples taken only while sitting.

Having the ability to determine the state of the user can be advantageous when it comes to scheduling tasks for the user and/or making recommendations for the user, which suits the user's state. In one embodiment, responsive to determining that the user is in the normal state, the computer prioritizes a first activity over a second activity, and responsive to determining that the user is in the abnormal state, the computer prioritizes the second activity over the first activity. Optionally, accomplishing each of the first and second activities requires at least a minute of the user's attention, and the second activity is more suitable for the abnormal state than the first activity. Optionally, and the first activity is more suitable for the normal state than the second activity. Optionally, prioritizing the first and second activities is performed by a calendar management program, a project management program, and/or a "to do" list program. Optionally, prioritizing a certain activity over another means one or more of the following: suggesting the certain activity before suggesting the other activity, suggesting the certain activity more frequently than the other activity (in the context of the specific state), allotting more time for the certain activity than for the other activity, and giving a more prominent reminder for the certain activity than for the other activity (e.g., an auditory indication vs. a mention in a calendar program that is visible only if the calendar program is opened).

Such state-dependent prioritization may be implemented in various scenarios. In one example, the normal state refers to a normal concentration level, the abnormal state refers to a lower than normal concentration level, and the first activity requires a high attention level from the user compared to the second activity. For instance, the first and second activities may relate to different topics of a self-learning program for school; when identifying that the user is in the normal concentration state, a math class is prioritized higher than a sports lesson; and when identifying that the user is in the lower concentration state, the math class is prioritized lower than the sports lesson. In another example, the normal state refers to a normal anger level, the abnormal state refers to a higher than normal anger level, and the first activity involves more interactions of the user with other humans compared to the second activity. In still another example, the normal state refers to a normal fear level, the abnormal state refers to a panic attack, and the second activity is expected to have a more relaxing effect on the user compared to the first activity.

In one embodiment, a system configured to alert about an abnormal state includes at least one CAM and a user interface (UI). The at least one CAM takes thermal measurements of at least first and second regions on the right side of the forehead ($TH_{R1}$ and $TH_{R2}$, respectively) of the user, and takes thermal measurements of at least third and fourth regions on the left side of the forehead ($TH_{L1}$ and $TH_{L2}$, respectively). The middles of the first and third regions are at least 1 cm above the middles of the second and fourth regions, respectively. Each of the at least one CAM is located below the first and third regions, and does not occlude any portion of the first and third regions. The UI provides an alert about an abnormal state of the user, where the abnormal state is determined based on $TH_{R1}$, $TH_{R2}$, $TH_{L1}$, and $TH_{L2}$. Optionally, the system includes a transmitter that may be used to transmit $TH_{R1}$, $TH_{R2}$, $TH_{L1}$, and $TH_{L2}$ to a computer that determines, based on $TH_{R1}$, $TH_{R2}$, $TH_{L1}$, and $TH_{L2}$, whether the user is in the normal state or the abnormal state. The computer may include a wearable computer, a computer belonging to a smartphone or a smartwatch carried by the user, and/or cloud-based server. Optionally, responsive to determining that the user is in an abnormal state, the computer commands the UI to provide the alert. For example, the computer may send a signal to a smartphone app, and/or to a software agent that has control of the UI, to provide the alert. In another example, the computer may send an instruction to the UI to provide the alert. Optionally, the alert is provided as text, image, sound, and/or haptic feedback.

The following method for alerting about an abnormal state may be used, in some embodiments, by the system configured to alert about the abnormal state (described above). The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, taking thermal measurements of at least first and second regions on the right side of the forehead ($TH_{R1}$, $TH_{R2}$) of a user, and thermal measurements of at least third and fourth regions on the left side of the forehead ($TH_{L1}$, $TH_{L2}$) of the user. The middles of the first and third regions are at least 1 cm above the middles of the second and fourth regions, respectively.

In Step 2, generating feature values based on $TH_{R1}$, $TH_{R2}$, $TH_{L1}$, and $TH_{L2}$.

In Step 3, utilizing a model for detecting a state of the user based on the feature values. The model was trained based on (i) previous feature values taken while the user was in a normal state, and (ii) other previous feature values taken while the user was in the abnormal state.

And in Step 4, responsive to detecting the abnormal state in Step 3, alerting about the abnormal state. In one example, the alerting may involve providing text, image, sound, and/or haptic feedback via the user interface.

Neurofeedback sessions can assist in treating various brain function-related conditions and/or disorders. In order to maximize their effectives, it may be advantageous to have neurofeedback treatments while a person suffers and/or exhibits the symptoms of a brain function-related condition and/or disorder. The following are descriptions of embodiments of a wearable system that may be utilized for this purpose. Some embodiments of a neurofeedback system described below involve a wearable, lightweight device that is aesthetically acceptable, and may be utilized as needed in day-to-day situations.

Some examples of disorders that may be treated with some embodiments of the neurofeedback system described herein include disorders related to (i) frontal lobe dysfunction, such as ADHD, headaches, anger, anxiety, and depression, (ii) paroxysmal disorders, such as headaches, seizures, rage reactions, and panic attacks, (iii) chronic pain, and (iv) stress. It is noted that the term "neurofeedback" also covers biofeedback and other similar feedback-based treatments.

FIG. 36 (already discussed above) illustrates one embodiment of a system configured to provide neurofeedback (based on measurements of CAM 720) and/or breathing biofeedback (based on measurements of at least some of thermal cameras 723, 725, 727 and 729). The system illustrated in FIG. 39, which uses two inward-facing head-mounted thermal cameras (701 and 702) to measure the forehead, may be used for neurofeedback together with a UI (not illustrated). Other embodiments of neurofeedback HMSs may involve more than two inward-facing head-mounted thermal cameras to measure the forehead. Some embodiments of neurofeedback HMSs may include one or more sensors such as the sensor 722, which are used to take $m_{conf}$ as discussed below.

Figure 41:
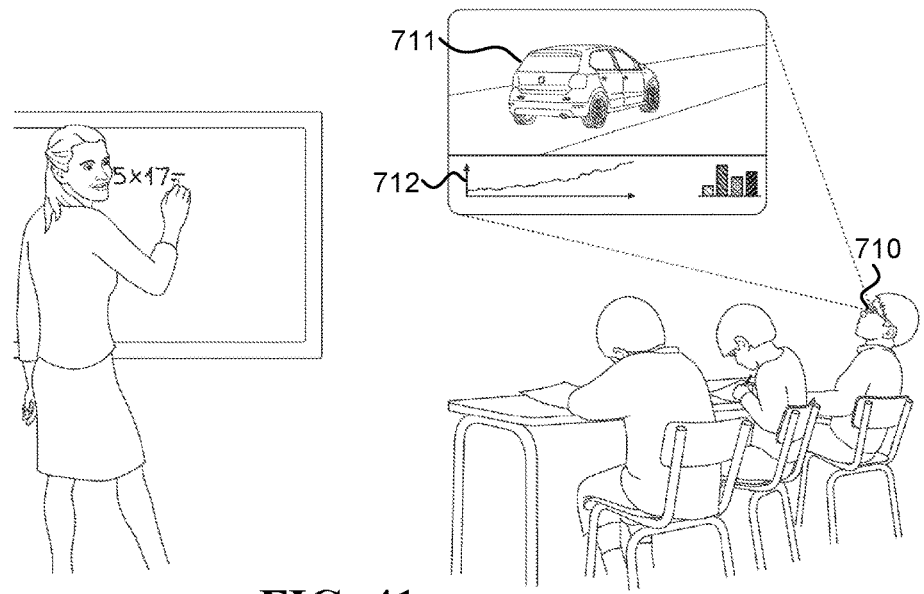
FIG. 41 illustrates a scenario in which a user has neurofeedback session during a day-to-day activity.

FIG. 41 illustrates a scenario in which a user has neurofeedback session during a day-to-day activity, such as during school time. For example, the session may be initiated because the user felt that he was losing concentration and/or the system might have determined that the user was exhibiting symptoms of ADHD and/or was in an undesirable state. The user wears an Augmented Reality device (AR), which includes user interface 710 that includes a display to present the augmented images. The AR includes one or more inward-facing head-mounted thermal cameras, which may be similar to the system illustrated in FIG. 36. The neurofeedback session involves attempting to control brain activity by causing the augmented reality video of the car 711 to drive forwards. For example, the car 711 drives forwards when the temperature at certain regions of the forehead 712 increases, and drives backwards when the temperature at the certain regions of the forehead 712 decreases.

In one embodiment, a neurofeedback system includes at least an inward-facing head-mounted thermal camera (CAM) and a user interface (UI). Optionally, the neurofeedback system may include additional elements such as a frame, a computer, and/or additional sensors and/or thermal cameras, as described below.

CAM is worn on a user's head and takes thermal measurements of a region on the forehead ($TH_F$) of the user. CAM is positioned such that when the user is upright, CAM is located below the middle of the region on the user's forehead. Optionally, CAM does not occlude the center of the forehead, and as such, may be more aesthetically pleasing than systems that have elements that occlude the center of the forehead. Optionally, CAM is located close to the forehead, at a distance below 15 cm, 10 cm, or 5 cm from the user's face. Optionally, CAM may use a single pixel sensor (e.g., discrete thermophile sensor) or a multiple pixel sensor (e.g., microbolometer FPA).

In one embodiment, $TH_F$ measured by CAM includes the area known in the field of electroencephalography as the "Fpz point", which is typically located at a point that is between 5% and 15% the distance from the nasion to the Inion (e.g., approximately at around 10% the distance). Optionally, in this embodiment, $TH_F$ may be indicative of temperature changes at the Fpz point. Additionally or alternatively, the region on the forehead measured by CAM may include the center of the forehead, and $TH_F$ may optionally be indicative of temperature changes at the center of the forehead.

In another embodiment, CAM may measure at least four areas on the user's forehead covering regions on the upper right side of the forehead, lower right side of the forehead, upper left side of the forehead, and lower left side of the forehead, respectively. Optionally, in this embodiment, $TH_F$ may be indicative of a thermal pattern of the user's forehead. Optionally, in this embodiment, "CAM" refers to multiple inward-facing thermal cameras, which include at least first and second inward-facing head-mounted thermal cameras (CAM1 and CAM2, respectively). CAM1 takes the measurements of the upper right side of the forehead and the lower right side of the forehead, and CAM2 takes the measurements of the upper left side of the forehead and the lower left side of the forehead. Optionally, $TH_F$ may include measurements of at least six areas on the user's forehead. Optionally, the at least four areas and the at least six areas each include at least one area that covers the Fpz point.

Due to the proximity of CAM to the face, in some embodiments, there may be an acute angle between the optical axis of CAM and the forehead. In order to improve the sharpness of thermal images of the forehead, in some embodiments, CAM may include a sensor and a lens, which are configured such that the sensor plane is tilted by more than 2° relative to the lens plane according to the Scheimpflug principle, which may enable the capture of sharper images of the forehead when CAM is close to the face.

The UI provides a feedback to the user during the neurofeedback session, which is determined based on $TH_F$ and optionally $m_{conf}$ (that is indicative of confounding factors). Optionally, providing the session for the user involves receiving instructions from the user (e.g., verbal commands and/or menu selections), which may affect the type of feedback the user receives (e.g., what type of session or "game" will be played in the session, how long the session should last, etc.).

In some embodiments, at least some of the feedback presented to the user via the UI is intended to indicate to the user whether, and optionally to what extent, the user's brain activity (as determined based on $TH_F$) is progressing towards a target. Optionally, the target may correspond to a state of brain activity that causes $TH_F$ to have a certain value. Optionally, the target may correspond to a typical $TH_F$ pattern of the user. Optionally, typical $TH_F$ pattern of the user is a pattern of temperatures on different points on the forehead, which determined based on previous $TH_F$ that are measured when the user was in a typical, normal state, and not exhibiting symptoms of anger, ADHD, a headache, etc. In one example, the user may be considered to make progress in the neurofeedback session if the temperature of the forehead (or a certain region on the forehead) becomes closer to a target temperature. In another example, the user may be considered to make progress in the neurofeedback session if the variability of temperatures across certain regions of the forehead reduces. In yet another example, the user may be considered to make progress in the neurofeedback session if asymmetry of temperatures of the forehead reduces. And in still another example, the user may be considered to make progress in the neurofeedback session if $TH_F$ pattern measured during the session becomes more similar to a certain target thermal pattern. Optionally, the user may receive feedback indicative of decreasing positive progress (or negative progress) when the $TH_F$ pattern measured during the session becomes less similar to the typical $TH_F$ pattern.

In one embodiment, video played as part of the feedback is played according to a protocol suitable for a passive infrared hemoencephalography (pIR HEG) session, which is a form of biofeedback for the brain that measures and displays information on the thermal output of the frontal lobe. In one configuration, pIR HEG involves increasing the forehead temperature by watching a movie that provides the feedback. The movie plays when the measured forehead temperature rises and stops when the temperature drops. The system may increase the threshold as the user learns how to raise the forehead temperature, and the user is instructed to calmly concentrate on making the movie continue to play.

The computer controls the neurofeedback session based on $TH_F$ and optionally $m_{conf}$. In one embodiment, the computer compares $TH_F$ to a target temperature. Optionally, different pixels of CAM may be compared to different target temperatures, or the target temperature may refer to an average temperature of the forehead. In another embodiment, the computer may calculate changes to temperature of the forehead ($\Delta T_F$) based on $TH_F$, and utilizes $\Delta T_F$ to control the neurofeedback session. In yet another embodiment, the computer may compare $TH_F$ to a target thermal pattern of the forehead, and the progress of the user in the neurofeedback session is evaluated based on a similarity between $TH_F$ and the target thermal pattern, and/or a change in extent of similarity between $TH_F$ and the target thermal pattern.

In one embodiment, $TH_F$ includes measurements of at least four non-collinear regions on the forehead (e.g., all the four regions do not lie on the same straight line), and the computer controls the neurofeedback session by providing the user a feedback via the user interface. The computer calculates a value indicative of similarity between a current $TH_F$ pattern and a previous $TH_F$ pattern of the user taken while the user was in a target state, and generates, based on the similarity, the feedback provided to the user as part of the neurofeedback session. The $TH_F$ pattern may refer to a spatial pattern of the at least four non-collinear regions on the forehead (e.g., a pattern in a thermal image received from a FPA sensor), and/or to a pattern in the time domain of the at least four non-collinear regions on the forehead (e.g., a pattern detected in a time series of the thermal measurements).

Neurofeedback sessions may have different target states in different embodiments. Generally, the purpose of a session is to bring the user's state during the neurofeedback session (the "present state") to become more similar to a target state. In one embodiment, while the user was in the target state, one or more of the following were true: the user was healthier compared to the present state, the user was more relaxed compared to the present state, a stress level of the user was below a threshold, the user's pain level was below a threshold, the user had no headache, the user did not suffer from depression, and the user was more concentrated compared to the present state. Additionally, the computer may receive an indication of a period during which the user was in the target state based on a report made by the user (the previous $TH_F$ pattern comprises $TH_F$ taken during the period), measurements of the user with a sensor other than CAM, semantic analysis of text written by the user, and/or analysis of the user's speech.

In some embodiments, the computer may utilize a machine learning-based model to determine whether the session is successful (or is expected to be) and/or to determine the user's progress in the neurofeedback session at a given time. Optionally, the computer generates feature values based on $TH_F$, and utilizes the model to calculate a value indicative of the progress and/or session success. Optionally, the model is trained on samples comprising feature values based on previously taken $TH_F$ and labels indicative of the success of the session and/or progress at the time those $TH_F$ were taken. Optionally, the samples may be generated based on previously taken $TH_F$ of the user and/or of other users. Optionally, the samples include samples generated based on $TH_F$ of the user taken on different days, and/or while the user was in different situations.

At a given time, temperatures measured at different areas of the forehead may be different. A value, which is a function of the temperatures at the different areas and is indicative of their variability, may be referred to herein as the "temperature variability" of the measurements. In one example, the function of the temperatures is the statistical variance of the temperatures. Having high temperature variability can be a sign that the user is suffering from various conditions, such as anger, a headache, depression, and/or anxiety. Optionally, a target of the neurofeedback session may be to lower the temperature variability of $TH_F$. Optionally, progress of the neurofeedback session may be evaluated based on a value of the temperature variability of $TH_F$, an extent that the temperature variability of $TH_F$ has decreased, and/or a rate at which the temperature variability of $TH_F$ has decreased.

Various brain function-related conditions may be manifested via asymmetrical thermal patterns on the forehead. Optionally, a target of a neurofeedback session in such cases may be to decrease the asymmetry of the thermal patterns. In one embodiment, CAM is located to the right of the vertical symmetry axis that divides the user's face (e.g. 701), and the region is on the right side of the forehead. The neurofeedback system may include a second inward-facing head-mounted thermal camera (e.g. 702), located to the left of the vertical symmetry axis, which takes thermal measurements of a second region on the left side of the forehead ($TH_{F2}$). Optionally, the computer provides to the user a feedback that becomes more positive as the temperature asymmetry between $TH_F$ and $TH_{F2}$ decreases.

Different regions on the forehead may be associated with different importance, with respect to various physiological responses and/or conditions that may be treated with neurofeedback sessions. In one embodiment, regions that are more important are associated with higher weights compared to weights associated with regions that are less important. Optionally, these weights may be utilized by the computer to calculate various values such as an average temperature of the forehead, which with the weights may be considered a "weighted average temperature". Similarly, a temperature variability of $TH_F$ that is calculated while taking into account the weights associated with the various areas may be a "weighted temperature variability", and temperature asymmetry between $TH_F$ and $TH_{F2}$, which is calculated while taking into account the weights associated with the various areas may be a "weighted temperature asymmetry". In some embodiments, providing feedback to the user based on one or more of the above "weighted" values may increase the efficacy of the neurofeedback session.

The temperature variability may be an indicator for the success or failure of the neurofeedback session. A session that causes a decreasing of the temperature variability below a certain first threshold may be considered a successful session that can be terminated, while a session that causes an increase of the temperature variability above a certain second threshold may be considered a failed session that should be terminated in order to prevent worsening the symptoms. In one embodiment, the computer terminates the neurofeedback session when $TH_F$ are indicative of the temperature variability decreasing below the certain first threshold. Additionally or alternatively, the computer may terminate the neurofeedback session when $TH_F$ are indicative of the temperature variability increasing above the certain second threshold.

In a similar fashion, the temperature asymmetry may be an indicator for the success or failure of the neurofeedback session for certain disorders. In one embodiment, the computer terminates the neurofeedback session when $TH_F$ are indicative of the temperature asymmetry decreasing below a certain first threshold. Additionally or alternatively, the computer may terminate the neurofeedback session when $TH_F$ are indicative of the temperature asymmetry increasing above a certain second threshold.

Having neurofeedback sessions, in a real world, day-to-day situations can involve conditions that are less sterile and not as controlled as the conditions that typically encountered when conducting such sessions at a clinic or a laboratory. In particular, thermal measurements of the forehead may be affected by various factors that are unrelated to the type of brain activity the user is conducting, as part of the session; these factors may often be absent and/or less extreme in controlled settings and/or may be noticed and accounted for by a practitioner (who for example, may tell the user not to touch the forehead). Such factors may be referred to herein as confounding factors. Some examples of confounding factors include touching the forehead (e.g., with one's fingers), thermal radiation directed at the forehead (e.g., direct sunlight), and direct airflow on the forehead (e.g., from an air conditioner). Each of these factors can cause changes in $TH_F$ that are not due to brain activity. In order to account for one or more of these confounding factors, in some embodiments, the neurofeedback includes a wearable sensor that takes measurements (denoted $m_{conf}$) indicative of at least one of the following confounding factors: touching the forehead, thermal radiation directed at the forehead, and direct airflow on the forehead. Optionally, the wearable sensor is coupled to a frame worn on the user's head. The following are some examples of types of sensors that the wearable sensor may involve in some embodiments of the neurofeedback system.

In one embodiment, the wearable sensor is an outward-facing head-mounted thermal camera ($CAM_{out}$) that takes thermal measurements of the environment ($TH_{ENV}$). Optionally, the angle between the optical axes of CAM and $CAM_{out}$ is at least one or more of the following angles: 45°, 90°, 130°, 170°, and 180°. In another embodiment, the wearable sensor provides measurements indicative of times at which the user touches the forehead. Optionally, the wearable sensor includes a visible-light camera, a miniature radar (such as low-power radar operating in the range between 30 GHz and 3,000 GHz), an active electro-optics distance measurement device (such as a miniature Lidar), and/or an ultrasound sensor. In yet another embodiment, the sensor may be an anemometer that is physically coupled to a frame worn on the user's head, is located less than 15 cm from the face, and provides a value indicative of a speed of air directed at the face.

There are various way in which the computer may utilize $m_{conf}$ to account for occurrences of a confounding factor during the neurofeedback session. In one embodiment, an occurrence of the confounding factor may prompt the computer to alert the user about the occurrence. In one example, the computer may identify, based on $m_{conf}$, that the extent of a confounding factor reached a threshold, and command the user interface to alert the user that the neurofeedback session is less accurate due to the confounding factor. In another example, upon identifying that the extent of a confounding factor reached the threshold, the computer may refrain from updating the feedback provided to the user as part of the neurofeedback session for at least a certain duration. The certain duration may be a fixed period (e.g., 0.2 seconds from reaching the threshold), and/or may last until $m_{conf}$ indicate that the extent of the confounding factor is below the threshold.

In one embodiment, the computer may adjust the values of $TH_F$ based on the values of $m_{conf}$ according to a certain function and/or transformation. For example, $TH_F$ may be normalized with respect to the intensity of thermal radiation directed at the face and/or the speed of wind directed at the face. In another embodiment, in which the computer utilizes the machine learning-based model to calculate a value indicative of the progress and/or success of the session, the computer may utilize $m_{conf}$ to generate at least some of the feature values that are utilized to calculate the value indicative of the progress and/or success. Optionally, the model is trained based on samples that include at least some samples that are based on $TH_F$ and $m_{conf}$ that were taken while a confounding factor affected $TH_F$.

Another approach that may be utilized by the computer, in some embodiments, is to learn to differentiate between changes to $TH_F$ due to brain activity and changes to $TH_F$ due to various confounding factors (which may have different characteristics). In one embodiment, the computer may generate feature values based on sets of $TH_F$ and $m_{conf}$, and utilize a second machine learning-based model to detect, based on the feature values, whether a change in $TH_F$ occurred responsive to brain activity or a confounding factor. Optionally, the second model may be trained on samples generated based on measurements taken at times that a confounding factor affected $TH_F$ and on other samples based on measurements taken at times that the confounding factor did not affect $TH_F$.

It is to be noted that since in real-world scenarios confounding factors can affect $TH_F$, utilizing one or more of the various measures described above may assist the computer to provide better neurofeedback sessions. Thus, in some embodiments, on average, neurofeedback sessions based on $TH_F$ and $m_{conf}$ provide better results than neurofeedback sessions based on $TH_F$ without $m_{conf}$.

In addition to confounding factors of which $m_{conf}$ may be indicative, in some embodiments, the computer may take into account in a similar way, other cofounding factors. In one embodiment, the neurofeedback system may include an additional wearable and/or head-mounted sensor used to detect a movement of the frame relative to the head while the frame is still worn, a change in the user's position, and/or a change in the user's body temperature. In another embodiment, the neurofeedback system may include a humidity sensor and/or an environmental temperature sensor, which may be coupled to the user.

Consumption of various substances may also be considered confounding factors. In one embodiment, the computer may receive an indication of whether the user took medication before the neurofeedback session (e.g., the type of medication and dosage), whether the user smoked, consumed alcohol, etc. Each of these factors may affect $TH_F$ in certain ways that may not necessarily be because of the user's brain activity. In a similar way to how the computer handles confounding factors in the description above, the computer may warn about the session being ineffective (e.g., after consuming alcohol or drugs) and/or perform various normalizations and/or computations to address these confounding factors (e.g., by generating feature values indicating the consumption of the substances).

Figure 40:
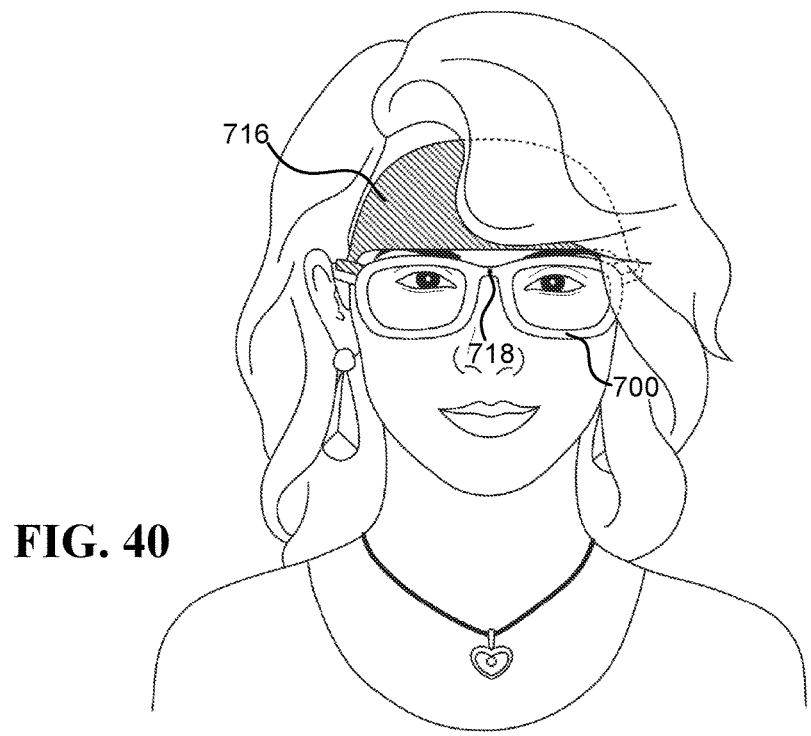
FIG. 40 illustrates an embodiment of a clip-on device configured to be attached and detached from a frame of eyeglasses multiple times.

Another way in which some confounding factors may be addressed, involves providing better insolation for the forehead region from the environment while the neurofeedback session is being conducted. To this end, one embodiment involves utilization of a clip-on structure designed to be attached and detached from the frame multiple times (e.g., it may be attached before a neurofeedback session starts and detached after the session terminates). Optionally, the clip-on includes a cover that occludes (when attached to the frame) the forehead region measured by CAM, which drives the neurofeedback. The clip-on may protect the region against environmental radiation, wind, and touching the region. FIG. 40 illustrates a clip-on 716 configured to be attached and detached from the frame 700 multiple times. The clip-on 716 includes a cover configured to occlude the region on the user's forehead (when the clip-on is attached to the frame) and a mechanism that holds the clip-on to the frame.

This selective use of the clip-on 716 can enable CAM 718 to provide different types of measurements. For example, $TH_F$ taken while the clip-on is attached may be less noisy then measurements taken when the clip-on is not attached. In some embodiments, measurements obtained without the clip-on may be too noisy for an effective neurofeedback session due to environmental confounding factors. Thus, in one embodiment, CAM may be used to detect that the user needs a neurofeedback session while the clip-on does not cover the region on the forehead (e.g., based on a thermal pattern of the forehead that indicates that the user is in an abnormal state). Optionally, the user is prompted to attach the clip-on and commence with the neurofeedback session. After the clip-on is attached, CAM takes $TH_F$ that are used effectively for the neurofeedback session (and may be of better quality than $TH_F$ taken when the clip-on is not attached).

The neurofeedback system may include, in some embodiments, one or more additional CAMs to measure physiological signals indicative of respiration, stress, and other relevant parameters. Optionally, a target of the neurofeedback session may include bringing these physiological signals to a certain value in addition to a target that is related to $TH_F$.

In one example, the neurofeedback system may include a second inward-facing head-mounted thermal camera (CAM2) that takes thermal measurements of a region below the nostrils ($TH_N$), which is indicative of the user's breathing Optionally, the computer may control the neurofeedback session also based on $TH_N$. Optionally, $TH_N$ is utilized to calculate values of one or more respiratory parameters, such as breathing rate, exhale duration, and/or smoothness of the exhale stream. Optionally, a target state for the neurofeedback session involves having certain values of the one or more respiratory parameters fall in certain ranges. In one example, CAM2 may be the thermal camera 727 or the thermal camera 729, which are illustrated in FIG. 36. Optionally, the computer calculates the user's breathing rate based on $TH_N$, and guides the user to breathe at his/her resonant frequency, which maximizes the amplitude of respiratory sinus arrhythmia and is in the range of 4.5 to 7.0 breaths/min.

In another example, the neurofeedback system may include second and third inward-facing head-mounted thermal cameras (CAM2 and CAM3, respectively), which take thermal measurements of regions on the periorbital area and the nose ($TH_{ROI2}$ and $TH_{ROI3}$, respectively). Optionally, the computer may control the neurofeedback session also based on $TH_{ROI2}$ and $TH_{ROI3}$. For example, the computer may calculate a stress level of the user based on $TH_{ROI2}$ and/or $TH_{ROI3}$, and a target state of the neurofeedback session may correspond to a certain stress level the user is supposed to have. Optionally, $TH_{ROI2}$ and $TH_{ROI3}$ may be utilized to calculate a stress level of the user. For example, CAM2 may be the thermal camera 724 or 726, and CAM3 may be the thermal camera 733, which are illustrated in FIG. 36.

The following method for conducting a neurofeedback session may be used, in some embodiments, by systems modeled according to FIG. 36. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, taking thermal measurements of a region on a forehead ($TH_F$) of the user, from a location below the middle of the region on the user's forehead and less than 10 cm from the user's forehead.

In Step 2, taking measurements ($m_{conf}$) indicative of at least one of the following confounding factors: touching the forehead, thermal radiation directed at the forehead, and direct airflow on the forehead.

And in Step 3, conducting a neurofeedback session for the user based on $TH_F$ and $m_{conf}$. Optionally, the neurofeedback session is controlled by a computer, as described above. Optionally, the method further includes generating feature values based on $TH_F$ and $m_{conf}$, and utilizing a model to control the neurofeedback session based on the feature values. Optionally, the model was trained on samples generated based on (i) previous $TH_F$ and $m_{conf}$ of the user, and/or (ii) previous $TH_F$ and $m_{conf}$ of other users.

Normally, the lens plane and the sensor plane of a camera are parallel, and the plane of focus (PoF) is parallel to the lens and sensor planes. If a planar object is also parallel to the sensor plane, it can coincide with the PoF, and the entire object can be captured sharply. If the lens plane is tilted (not parallel) relative to the sensor plane, it will be in focus along a line where it intersects the PoF. The Scheimpflug principle is a known geometric rule that describes the orientation of the plane of focus of a camera when the lens plane is tilted relative to the sensor plane.

Figure 20A:
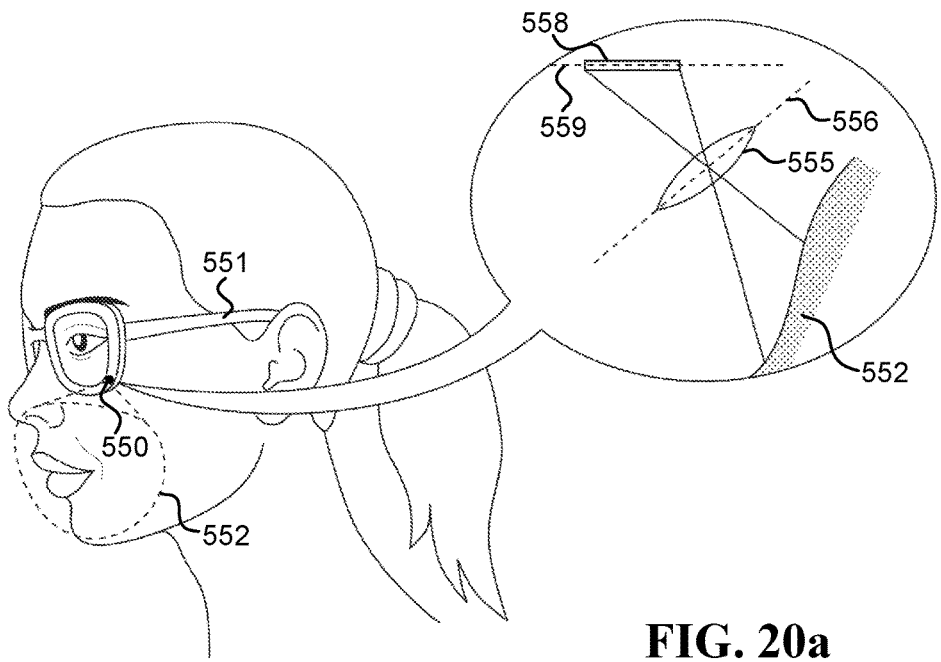
FIG. 20a is a schematic illustration of an inward-facing head-mounted camera embedded in an eyeglasses frame, which utilizes the Scheimpflug principle.

FIG. 20a is a schematic illustration of an inward-facing head-mounted camera 550 embedded in an eyeglasses frame 551, which utilizes the Scheimpflug principle to improve the sharpness of the image taken by the camera 550. The camera 550 includes a sensor 558 and a lens 555. The tilt of the lens 555 relative to sensor 558, which may also be considered as the angle between the lens plane 555 and the sensor plane 559, is determined according to the expected position of the camera 550 relative to the ROI 552 when the user wears the eyeglasses. For a refractive optical lens, the "lens plane" 556 refers to a plane that is perpendicular to the optical axis of the lens 555. Herein, the singular also includes the plural, and the term "lens" refers to one or more lenses. When "lens" refers to multiple lenses (which is usually the case in most modern cameras having a lens module with multiple lenses), then the "lens plane" refers to a plane that is perpendicular to the optical axis of the lens module.

Figure 20B:
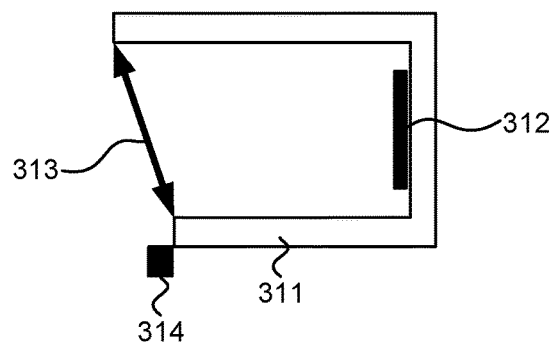
FIG. 20b is a schematic illustration of a camera that is able to change the relative tilt between its lens and sensor planes according to the Scheimpflug principle.

The Scheimpflug principle may be used for both thermal cameras (based on lenses and sensors for wavelengths longer than 2500 nm) and visible-light and/or near-IR cameras (based on lenses and sensors for wavelengths between 400-900 nm). FIG. 20b is a schematic illustration of a camera that is able to change the relative tilt between its lens and sensor planes according to the Scheimpflug principle. Housing 311 mounts a sensor 312 and lens 313. The lens 313 is tilted relative to the sensor 312. The tilt may be fixed according to the expected position of the camera relative to the ROI when the user wears the HMS, or may be adjusted using motor 314. The motor 314 may move the lens 313 and/or the sensor 312.

In one embodiment, an HMS device includes a frame configured to be worn on a user's head, and an inward-facing camera physically coupled to the frame. The inward-facing camera may assume one of two configurations: (i) the inward-facing camera is oriented such that the optical axis of the camera is above the Frankfort horizontal plane and pointed upward to capture an image of a region of interest (ROI) above the user's eyes, or (ii) the inward-facing camera is oriented such that the optical axis is below the Frankfort horizontal plane and pointed downward to capture an image of an ROI below the user's eyes. The inward-facing camera includes a sensor and a lens. The sensor plane is tilted by more than 2° relative to the lens plane according to the Scheimpflug principle in order to capture a sharper image.

In another embodiment, an HMS includes an inward-facing head-mounted camera that captures an image of an ROI on a user's face, when worn on the user's head. The ROI is on the user's forehead, nose, upper lip, cheek, and/or lips. The camera includes a sensor and a lens. And the sensor plane is tilted by more than 2° relative to the lens plane according to the Scheimpflug principle in order to capture a sharper image.

Because the face is not planar and the inward-facing head-mounted camera is located close to the face, an image captured by a camera having a wide field of view (FOV) and a low f-number may not be perfectly sharp, even after applying the Scheimpflug principle. Therefore, in some embodiments, the tilt between the lens plane and the sensor plane is selected such as to adjust the sharpness of the various areas covered in the ROI according to their importance for detecting the user's physiological response (which may be the user's emotional response in some cases). In one embodiment, the ROI covers first and second areas, where the first area includes finer details and/or is more important for detecting the physiological response than the second area. Therefore, the tilt between the lens and sensor planes is adjusted such that the image of the first area is shaper than the image of the second area.

In another embodiment, the ROI covers both a first area on the upper lip and a second area on a cheek, and the tilt is adjusted such that the image of the first area is shaper than the image of the second area, possibly because the upper lip usually provides more information and has more details relative to the cheek.

In still another embodiment, the ROI covers both a first area on the upper lip and a second area on the nose, and the tilt is adjusted such that the image of the first area is shaper than the image of the second area, possibly because the upper lip usually provides more information relative to the nose.

In still another embodiment, the ROI covers a first area on the cheek straight above the upper lip, a second area on the cheek from the edge of the upper lip towards the ear, and a third area on the nose. And the tilt between the lens plane and the sensor plane is adjusted such that the image of the first area is shaper than both the images of the second and third areas.

In still another embodiment, the ROI covers both a first area on the lips and a second area on the chin, and the tilt is adjusted such that the image of the first area is shaper than the image of the second area, possibly because the lips usually provides more information than the chin.

In still another embodiment, the camera is a visible-light camera, and the ROI covers both a first area on the lower forehead (including an eyebrow) and a second area on the upper forehead, and the tilt is adjusted such that the image of the first area is shaper than the image of the second area, possibly because the eyebrow provides more information about the user's emotional response than the upper forehead.

In still another embodiment, the camera is a thermal camera, and the ROI covers an area on the forehead, and the tilt is adjusted such that the image of a portion of the middle and upper part of the forehead (below the hair line) is shaper than the image of a portion of the lower part of the forehead, possibly because the middle and upper parts of the forehead are more indicative of prefrontal cortex activity than the lower part of the forehead, and movements of the eyebrows disturb the thermal measurements of the lower part of the forehead.

In one embodiment, the tilt between the lens plane and sensor plane is fixed. The fixed tilt is selected according to an expected orientation between the camera and the ROI when a user wears the frame. Having a fixed tilt between the lens and sensor planes may eliminate the need for an adjustable electromechanical tilting mechanism. As a result, a fixed tilt may reduce the weight and cost of the camera, while still providing a sharper image than an image that would be obtained from a similar camera in which the lens and sensor planes are parallel. The magnitude of the fixed tilt may be selected according to facial dimensions of an average user expected to wear the system, or according to a model of the specific user expected to wear the system in order to obtain the sharpest image.

In another embodiment, the system includes an adjustable electromechanical tilting mechanism configured to change the tilt between the lens and sensor planes according to the Scheimpflug principle based on the orientation between the camera and the ROI when the frame is worn by the user. The tilt may be achieved using at least one motor, such as a brushless DC motor, a stepper motor (without a feedback sensor), a brushed DC electric motor, a piezoelectric motor, and/or a micro-motion motor.

The adjustable electromechanical tilting mechanism configured to change the tilt between the lens and sensor planes may include one or more of the following mechanisms: (i) a mirror that changes its angle; (ii) a device that changes the angle of the lens relative to the sensor; and/or (iii) a device that changes the angle of the sensor relative to the lens. In one embodiment, the camera, including the adjustable electromechanical tilting mechanism, weighs less than 10 g, and the adjustable electromechanical tilting mechanism is able to change the tilt in a limited range below 30° between the two utmost orientations between the lens and sensor planes. Optionally, the adjustable electromechanical tilting mechanism is able to change the tilt in a limited range below 20° between the two utmost orientations between the lens and sensor planes. In another embodiment, the adjustable electromechanical tilting mechanism is able to change the tilt in a limited range below 10°. In some embodiments, being able to change the tilt in a limited range reduces at least one of the weight, cost, and size of the camera, which is advantageous for a wearable device. In one example, the camera is manufactured with a fixed predetermined tilt between the lens and sensor planes, which is in addition to the tilt provided by the adjustable electromechanical tilting mechanism. The fixed predetermined orientation may be determined according to the expected orientation between the camera and the ROI for an average user, such that the adjustable electromechanical tilting mechanism is used to fine-tune the tilt between the lens and sensor planes for the specific user who wears the frame and has facial dimensions that are different from the average user.

Various types of cameras may be utilized in different embodiments described herein. In one embodiment, the camera is a thermal camera that takes thermal measurements of the ROI with a focal plane array thermal sensor having an angle above 2° between the lens and sensor planes. Optionally, the thermal camera weighs below 10 g, is located less than 10 cm from the user's face, and the tilt of the lens plane relative to the sensor plane is fixed. The fixed tilt is selected according to an expected orientation between the camera and the ROI when the user wears the frame. Optionally, the system includes a computer to detect a physiological response based on the thermal measurements. Optionally, the computer processes time series measurements of each sensing element individually to detect the physiological response.

In another embodiment, the camera is a visible-light camera that takes visible-light images of the ROI, and a computer generates an avatar for the user based on the visible-light images. Some of the various approaches that may be utilized to generate the avatar based on the visible-light images are described in co-pending US patent publication 2016/0360970. Additionally or alternatively, the computer may detect an emotional response of the user based on (i) facial expressions in the visible-light images utilizing image processing, and/or (ii) facial skin color changes (FSCC), which result from concentration changes of hemoglobin and/or oxygenation.

It is to be noted that there are various approaches known in the art for identifying facial expressions from images. While many of these approaches were originally designed for full-face frontal images, those skilled in the art will recognize that algorithms designed for full-face frontal images may be easily adapted to be used with images obtained using the inward-facing head-mounted visible-light cameras disclosed herein. For example, the various machine learning techniques described in prior art references may be applied to feature values extracted from images that include portions of the face from orientations that are not directly in front of the user. Furthermore, due to the closeness of the visible-light cameras to the face, facial features are typically larger in images obtained by the systems described herein. Moreover, challenges such as image registration and face tracking are vastly simplified and possibly non-existent when using inward-facing head-mounted cameras. The reference Zeng, Zhihong, et al. "A survey of affect recognition methods: Audio, visual, and spontaneous expressions." IEEE transactions on pattern analysis and machine intelligence 31.1 (2009): 39-58, describes some of the algorithmic approaches that may be used for this task. The following references discuss detection of emotional responses based on FSCC: (i) Ramirez, Geovany A., et al. "Color analysis of facial skin: Detection of emotional state" in Proceedings of the IEEE Conference on Computer Vision and Pattern Recognition Workshops, 2014; and (ii) Wang, Su-Jing, et al. "Micro-expression recognition using color spaces", in IEEE Transactions on Image Processing 24.12 (2015): 6034-6047.

In still another embodiment, the camera is a light field camera that implements a predetermined blurring at a certain Scheimpflug angle, and decodes the predetermined blurring as function of the certain Scheimpflug angle. The light field camera may include an autofocusing of the image obtained using the tilting mechanism based on the principle that scene points that are not in focus are blurred while scene points in focus are sharp. The autofocusing may study a small region around a given pixel; the region is expected to get sharper as the Scheimpflug adjustment gets better, and vice versa. Additionally or alternatively, the autofocusing may use the variance of the neighborhood around each pixel as a measure of sharpness, where a proper Scheimpflug adjustment should increase the variance.

Thermal and/or FSCC patterns corresponding to physiological responses may show high variability between different users due to variability of the their brains, blood vessel locations, skin properties, hair, physical conditions, and face shapes and sizes. Thus, patterns and/or various extractable features from one user's thermal and/or FSCC data may not be easily transferable to another user, or even to the same user under different physiological and/or mental conditions. Therefore, some of the embodiments described herein involve training personalized models involving thermal and/or FSCC patterns that are predictive of various user-defined categories of experiencing and/or perceiving certain events. Personalized models can overcome some of the possible disadvantages of using normed physiological statistics, which paves the way for personalized training, detection, and therapies, which are able to account for arbitrary user-defined physiological and/or mental states corresponding to a wide variety of individual needs. Leveraging machine learning algorithms can enable assignment of arbitrary user-defined physiological and/or mental states to recorded thermal and/or FSCC data during day-to-day activities, which are later used as basis for automatic detection and/or therapies for the user, optionally without involving a clinician.

The personalized model does not need to correspond to a standard universally applicable pattern, and thus the user may be free to define his/her arbitrary user-defined physiological and/or mental states. In other words, in addition to (or instead of) detecting a state that corresponds to some arbitrary population average, the personalized model allows a personalized detection of a user-defined state.

One embodiment in which a personalized model is utilized involves a training phase and an operation phase. In the training phase, the system identifies desired and/or undesired physiological and/or mental states of the user using active methods (e.g., the user presses a button) and/or passive methods (e.g., applying semantic analysis to the user's speech and typing). The system may also continue to update the personalized model to accommodate for changes over time, to supports increased efficacy, and to identify new personalized states beyond those represented by population average. Instead of relying on a model trained based on data obtained from a wide population, the personalized model may decouple commonly coupled ROIs and/or putative physiological responses from the applications, allowing the user to train the system to detect arbitrary personalized thermal and/or FSCC patterns that may not suite the wide population. Training the personalized model may be based on known machine learning methods such as neural networks, supervised machine learning, pattern recognition, pattern matching, etc. The system may detect, predict, and train for the arbitrary user-defined physiological and/or mental states, identified by personalized thermal and/or FSCC patterns, not limited to averages obtained from a wide population.

In the operation phase, the system alerts, predicts, and/or treats the user based on the personalized model. The system may alert when the user is in the desired/undesired state, predict when the user is going to be in that state, and treat the user to get into a desired state or avoid an undesired state by providing a feedback. The operation phase may include known biofeedback/neurofeedback interactive sessions tuned to guide the user towards the user-defined personalized physiological and/or mental states. For example, the personalized model may be trained to guide the user towards flow, creativity, curiosity, compassion, and/or happiness states, as defined and experienced by the user, and to alert against anger, aggression, boredom, and/or sadness, also as defined and experienced by the user, without these necessarily being suitable for the wide population.

One embodiment of a method for personalized thermal and/or FSCC detection includes a timestamping step, a machine learning step, a refinement step, an optional detection step, and an optional biofeedback step (where biofeedback refers also to neurofeedback).

In the timestamping step, an HMS records arbitrary user-defined physiological and/or mental states for personal use. The user may provide, via a user interface, timestamped markers on the recorded data used as labels by machine learning approaches for detecting target user-defined physiological and/or mental states (which may be desired or undesired states). When the user engages in a certain task, and as the user enters a target state, the user may (via a user interface) manual provide a timestamp to mark the time of entering into the target state, and/or the computer may set an automated timestamp based on inferring the entering into the target state from the user's performance and/or activities (for example, using predetermined limits of performance that once reached automatically trigger timestamping the recorded data as entering into the target state). Upon leaving the target state, the user may provide a timestamp to mark the leaving of the target state, and/or the computer may set an automated timestamp based on inferring the leaving of the target state from the user's performance and/or activities. Several iterations involving time stamping of entering and leaving the target state may complete the time stamping step.

In the machine learning step, the computer extracts and selects features from the thermal and/or FSCC measurements, labels the extracted and selected features according to the timestamps, and tries one or more machine learning algorithms to train a classifier, while treating the measurements as the training and testing sets. Optionally, for unique personalized states, the machine learning algorithm may be optimized for cross-validation by splitting the training set into a first part used for training and a second part used for testing. In addition, testing sets comprising data of other users may be used to measure the classifier's generality. The following examples illustrate various ways to label the HMS measurements based on the timestamps.

In a first example, the computer may (i) label as "not desired" $TH_{ROI}$ taken before receiving from the user a first timestamp marking the entering into a desired state, (ii) label as "desired" $TH_{ROI}$ taken after receiving the first timestamp and before receiving a second timestamp marking the leaving of the desired state, and (iii) label as "not desired" $TH_{ROI}$ taken after receiving the second timestamp. Optionally, the computer may label as "unknown" $TH_{ROI}$ taken sufficiently before receiving the first timestamp and $TH_{ROI}$ taken sufficiently after receiving the second timestamp.

In a second example, the computer may (i) label as "leading to headache" $TH_{ROI}$ taken during a first window of time before receiving from the user a first timestamp marking occurrence of a headache, (ii) label as "headache" $TH_{ROI}$ taken after receiving the first timestamp and until a second window before receiving from the user a second timestamp marking "no headache", (iii) label as "headache leaving" $TH_{ROI}$ taken during the second window, and (iv) label as "no headache" $TH_{ROI}$ taken after receiving the second timestamp.

In a third example, the computer may (i) label as "leading to asthma attack" $TH_{breath}$ indicative of the user's breathing pattern (such as thermal measurements of a region on the upper lip) taken during a first window before identifying that the user uses a first inhaler, (ii) label as "first inhaler immediate effect" $TH_{breath}$ taken during a second window after using the first inhaler, (iii) label as "first inhaler long effect" $TH_{breath}$ taken during a third window following the second window, and (iv) label as "second inhaler immediate effect" $TH_{breath}$ taken during a fourth window after identifying that the user uses a second inhaler. Optionally, the computer may use the automated labeling for assessing the user's reaction to using the first inhaler vs using the second inhaler.

In a fourth example, the computer may (i) label as "building concentration" $TH_{breath}$ indicative of the user's breathing pattern and $TH_{forehead}$ indicative of a thermal pattern on the user's forehead taken while the user's software agent indicates that the user does not check distracting websites (such as social networks, news and email) but the user's gaze is not essentially continuously focused on the screen, (ii) label as "concentrated" $TH_{breath}$ and $TH_{forehead}$ taken while the software agent indicates that the user's gaze is continuously focused on the screen and until a certain duration before the user lost concentration, and In a fifth example, the computer may (i) label as "possibly happy" $TH_{ROI}$ and FSCC taken during a first window before a speech analysis module provides a timestamp that the user is happy, (ii) label as "happy" $TH_{ROI}$ and FSCC taken during a second window after receiving the timestamp, and (iii) label as "angry" $TH_{ROI}$ and FSCC taken during a third window after the speech analysis module provides a timestamp that the user is angry.

In the refinement step, the computer starts guessing the physiological and/or mental states, and asks the user to confirm correct, incorrect, or inapplicable status of the guesses. The refinement step increases fidelity the more it is performed.

In the optional detection step, the computer analyzes in real time feature values generated based on the thermal and/or FSCC measurements in order to alert the user about entering and/or leaving a target state. For example, the computer permits administration of pain medication to the user after the classifier determines that the user experiences pain above a threshold previously determined by the user during the timestamping step. This may reduce addiction by reducing unnecessary administrations of higher dose pain medication. Additionally, the user may be trained to control his/her pain perception during the biofeedback step, which may be more effective after a personalized model has been applied.

In the optional biofeedback step, the computer generates a feedback for the user based on the personalized target state. The biofeedback step may use a standard biofeedback protocol, but instead of training the user towards achieving externally derived thermal and/or FSCC target patterns that suit the wide population, the user is trained to achieve personalized thermal and/or FSCC target patterns that most closely resemble the thermal and/or FSCC patterns found to be predictive during the timestamping and refinement steps.

In one embodiment, the user labels during the timestamping step pairs of undesired and desired states (such as pain vs no pain, migraine vs no migraine, angry vs calmed, stressed vs calmed, concentrated vs not concentrated, sad vs happy, self-focused vs compassionate). Then the biofeedback step trains the user to move out of the undesired state by (i) encouraging changes that bring the current measured thermal and/or FSCC pattern closer to the desired personalized thermal and/or FSCC pattern found to be predictive during the timestamping and refinement steps, and (ii) discouraging changes that bring the current measured thermal and/or FSCC pattern closer to the undesired personalized thermal and/or FSCC pattern found to be predictive during the timestamping and refinement steps.

The following is one example of the information flow in an HMS that includes a head-mounted thermal camera and a computer. In the timestamping step, the head-mounted thermal camera takes thermal measurements, and the user (or computer) adds manual (or automated) timestamps for entering and/or leaving a target state. The timestamping step feeds the machine learning step, in which a machine learning-based training algorithm is used to train a personalized model that is evaluated against user measurements in known states. The machine learning step feeds the refinement step with processed data and questions, and in the refinement step the user answers whether the machine learning algorithm has correctly detected the user's state. Both the machine learning step and the refinement step may provide data to the optional detection and biofeedback steps (which may communicate with each other).

Big data analysis may be performed to identify trends and detect new correlations over users and populations, together with other sources of information, such as other wearable devices (e.g., smart watches, smart shirts, EEG headsets, smart earphones), mobile devices (e.g., smartphone, laptop), and other sources of information (e.g., social networks, search engines, bots, software agents, medical records, IoT devices).

Various embodiments described herein involve an HMS that may be connected, using wires and/or wirelessly, with a device carried by the user and/or a non-wearable device. The HMS may include a battery, a computer, sensors, and a transceiver.

Figure 42A:
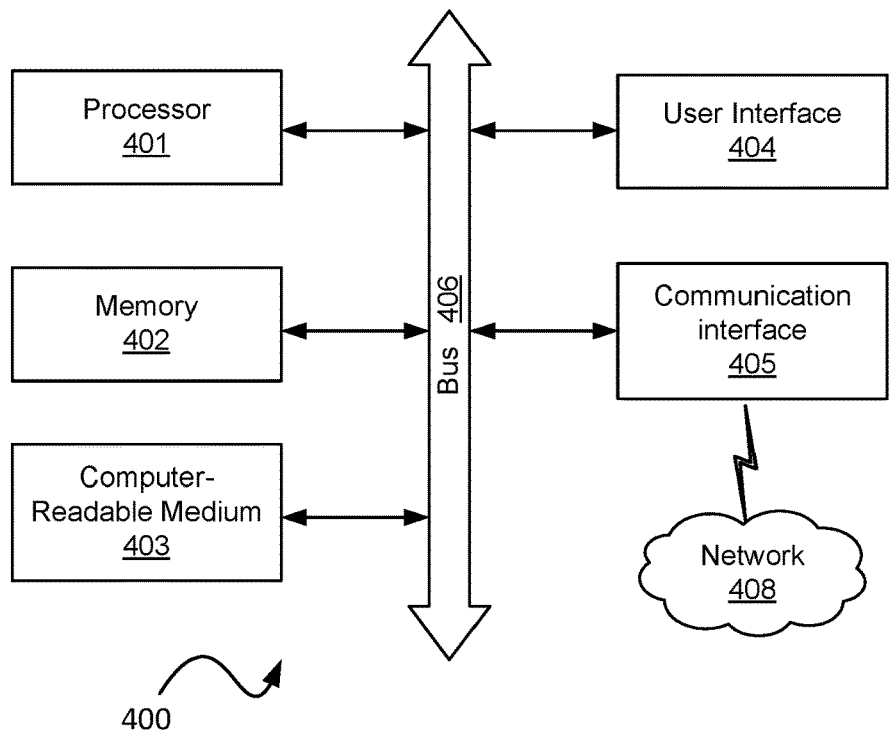
FIG. 42a and FIG. 42b are schematic illustrations of possible embodiments for computers.
Figure 42B:
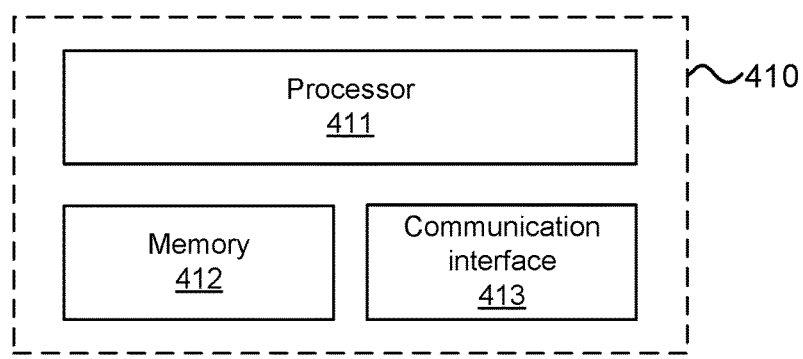

FIG. 42a and FIG. 42b are schematic illustrations of possible embodiments for computers (400, 410) that are able to realize one or more of the embodiments discussed herein that include a "computer". The computer (400, 410) may be implemented in various ways, such as, but not limited to, a server, a client, a personal computer, a network device, a handheld device (e.g., a smartphone), an HMS (such as smart glasses, an augmented reality system, and/or a virtual reality system), a computing device embedded in a wearable device (e.g., a smartwatch or a computer embedded in clothing), a computing device implanted in the human body, and/or any other computer form capable of executing a set of computer instructions. Herein, an augmented reality system refers also to a mixed reality system. Further, references to a computer or processor include any collection of one or more computers and/or processors (which may be at different locations) that individually or jointly execute one or more sets of computer instructions. For example, a first computer may be embedded in the HMS that communicates with a second computer embedded in the user's smartphone that communicates over the Internet with a cloud computer.

The computer 400 includes one or more of the following components: processor 401, memory 402, computer readable medium 403, user interface 404, communication interface 405, and bus 406. The computer 410 includes one or more of the following components: processor 411, memory 412, and communication interface 413.

Thermal measurements that are forwarded to a processor/computer may include "raw" values that are essentially the same as the values measured by thermal cameras, and/or processed values that are the result of applying some form of preprocessing and/or analysis to the raw values. Examples of methods that may be used to process the raw values include analog signal processing, digital signal processing, and various forms of normalization, noise cancellation, and/or feature extraction.

Functionality of various embodiments may be implemented in hardware, software, firmware, or any combination thereof. If implemented at least in part in software, implementing the functionality may involve a computer program that includes one or more instructions or code stored or transmitted on a computer-readable medium and executed by one or more processors. Computer-readable media may include computer-readable storage media, which corresponds to a tangible medium such as data storage media, or communication media including any medium that facilitates transfer of a computer program from one place to another. Computer-readable medium may be any media that can be accessed by one or more computers to retrieve instructions, code, data, and/or data structures for implementation of the described embodiments. A computer program product may include a computer-readable medium. In one example, the computer-readable medium 403 may include one or more of the following: RAM, ROM, EEPROM, optical storage, magnetic storage, biologic storage, flash memory, or any other medium that can store computer readable data.

A computer program (also known as a program, software, software application, script, program code, or code) can be written in any form of programming language, including compiled or interpreted languages, declarative or procedural languages. The program can be deployed in any form, including as a standalone program or as a module, component, subroutine, object, or another unit suitable for use in a computing environment. A computer program may correspond to a file in a file system, may be stored in a portion of a file that holds other programs or data, and/or may be stored in one or more files that may be dedicated to the program. A computer program may be deployed to be executed on one or more computers that are located at one or more sites that may be interconnected by a communication network.

Computer-readable medium may include a single medium and/or multiple media (e.g., a centralized or distributed database, and/or associated caches and servers) that store one or more sets of instructions. In various embodiments, a computer program, and/or portions of a computer program, may be stored on a non-transitory computer-readable medium, and may be updated and/or downloaded via a communication network, such as the Internet. Optionally, the computer program may be downloaded from a central repository, such as Apple App Store and/or Google Play. Optionally, the computer program may be downloaded from a repository, such as an open source and/or community run repository (e.g., GitHub).

At least some of the methods described herein are "computer-implemented methods" that are implemented on a computer, such as the computer (400, 410), by executing instructions on the processor (401, 411). Additionally, at least some of these instructions may be stored on a non-transitory computer-readable medium.

Herein, a direction of the optical axis of a VCAM or a CAM that has focusing optics is determined by the focusing optics, while the direction of the optical axis of a CAM without focusing optics (such as a single pixel thermopile) is determined by the angle of maximum responsivity of its sensor. When optics are utilized to take measurements with a CAM, then the term CAM includes the optics (e.g., one or more lenses). In some embodiments, the optics of a CAM may include one or more lenses made of a material suitable for the required wavelength, such as one or more of the following materials: Calcium Fluoride, Gallium Arsenide, Germanium, Potassium Bromide, Sapphire, Silicon, Sodium Chloride, and Zinc Sulfide. In other embodiments, the CAM optics may include one or more diffractive optical elements, and/or or a combination of one or more diffractive optical elements and one or more refractive optical elements.

When CAM includes an optical limiter/field limiter/FOV limiter (such as a thermopile sensor inside a standard TO-39 package with a window, or a thermopile sensor with a polished metal field limiter), then the term CAM may also refer to the optical limiter. Depending on the context, the term CAM may also refer to a readout circuit adjacent to CAM, and/or to the housing that holds CAM.

Herein, references to thermal measurements in the context of calculating values based on thermal measurements, generating feature values based on thermal measurements, or comparison of thermal measurements, relate to the values of the thermal measurements (which are values of temperature or values of temperature changes). Thus, a sentence in the form of "calculating based on $TH_{ROI}$" may be interpreted as "calculating based on the values of $TH_{ROI}$", and a sentence in the form of "comparing $TH_{ROI1}$ and $TH_{ROI2}$" may be interpreted as "comparing values of $TH_{ROI1}$ and values of $TH_{ROI2}$".

Depending on the embodiment, thermal measurements of an ROI (usually denoted $TH_{ROI}$ or using a similar notation) may have various forms, such as time series, measurements taken according to a varying sampling frequency, and/or measurements taken at irregular intervals. In some embodiments, thermal measurements may include various statistics of the temperature measurements (T) and/or the changes to temperature measurements ($\Delta T$), such as minimum, maximum, and/or average values. Thermal measurements may be raw and/or processed values. When a thermal camera has multiple sensing elements (pixels), the thermal measurements may include values corresponding to each of the pixels, and/or include values representing processing of the values of the pixels. The thermal measurements may be normalized, such as normalized with respect to a baseline (which is based on earlier thermal measurements), time of day, day in the month, type of activity being conducted by the user, and/or various environmental parameters (e.g., the environment's temperature, humidity, radiation level, etc.).

As used herein, references to "one embodiment" (and its variations) mean that the feature being referred to may be included in at least one embodiment of the invention. Moreover, separate references to "one embodiment", "some embodiments", "another embodiment", "still another embodiment", etc., may refer to the same embodiment, may illustrate different aspects of an embodiment, and/or may refer to different embodiments.

Some embodiments may be described using the verb "indicating", the adjective "indicative", and/or using variations thereof. Herein, sentences in the form of "X is indicative of Y" mean that X includes information correlated with Y, up to the case where X equals Y. For example, sentences in the form of "thermal measurements indicative of a physiological response" mean that the thermal measurements include information from which it is possible to infer the physiological response. Stating that "X indicates Y" or "X indicating Y" may be interpreted as "X being indicative of Y". Additionally, sentences in the form of "provide/receive an indication indicating whether X happened" may refer herein to any indication method, including but not limited to: sending/receiving a signal when X happened and not sending/receiving a signal when X did not happen, not sending/receiving a signal when X happened and sending/receiving a signal when X did not happen, and/or sending/receiving a first signal when X happened and sending/receiving a second signal X did not happen.

Herein, "most" of something is defined as above 51% of the something (including 100% of the something). Both a "portion" of something and a "region" of something refer herein to a value between a fraction of the something and 100% of the something. For example, sentences in the form of a "portion of an area" may cover between 0.1% and 100% of the area. As another example, sentences in the form of a "region on the user's forehead" may cover between the smallest area captured by a single pixel (such as 0.1% or 5% of the forehead) and 100% of the forehead. The word "region" refers to an open-ended claim language, and a camera said to capture a specific region on the face may capture just a small part of the specific region, the entire specific region, and/or a portion of the specific region together with additional region(s).

Sentences in the form of "angle greater than 20°" refer to absolute values (which may be +20° or −20° in this example), unless specifically indicated, such as in a phrase having the form of "the optical axis of CAM is 20° above/below the Frankfort horizontal plane" where it is clearly indicated that the CAM is pointed upwards/downwards. The Frankfort horizontal plane is created by two lines from the superior aspects of the right/left external auditory canal to the most inferior point of the right/left orbital rims.

The terms "comprises," "comprising," "includes," "including," "has," "having", or any other variation thereof, indicate an open-ended claim language that does not exclude additional limitations. The "a" or "an" is employed to describe one or more, and the singular also includes the plural unless it is obvious that it is meant otherwise; for example, sentences in the form of "a CAM configured to take thermal measurements of a region ($TH_{ROI}$)" refers to one or more CAMs that take thermal measurements of one or more regions, including one CAM that takes thermal measurements of multiple regions; as another example, "a computer" refers to one or more computers, such as a combination of a wearable computer that operates together with a cloud computer.

The phrase "based on" is intended to mean "based, at least in part, on". Additionally, stating that a value is calculated "based on X" and following that, in a certain embodiment, that the value is calculated "also based on Y", means that in the certain embodiment, the value is calculated based on X and Y.

The terms "first", "second" and so forth are to be interpreted merely as ordinal designations, and shall not be limited in themselves. A predetermined value is a fixed value and/or a value determined any time before performing a calculation that compares a certain value with the predetermined value. A value is also considered to be a predetermined value when the logic, used to determine whether a threshold that utilizes the value is reached, is known before start performing computations to determine whether the threshold is reached.

The embodiments of the invention may include any variety of combinations and/or integrations of the features of the embodiments described herein. Although some embodiments may depict serial operations, the embodiments may perform certain operations in parallel and/or in different orders from those depicted. Moreover, the use of repeated reference numerals and/or letters in the text and/or drawings is for the purpose of simplicity and clarity and does not in itself dictate a relationship between the various embodiments and/or configurations discussed. The embodiments are not limited in their applications to the order of steps of the methods, or to details of implementation of the devices, set in the description, drawings, or examples. Moreover, individual blocks illustrated in the figures may be functional in nature and therefore may not necessarily correspond to discrete hardware elements.

Certain features of the embodiments, which may have been, for clarity, described in the context of separate embodiments, may also be provided in various combinations in a single embodiment. Conversely, various features of the embodiments, which may have been, for brevity, described in the context of a single embodiment, may also be provided separately or in any suitable sub-combination. Embodiments described in conjunction with specific examples are presented by way of example, and not limitation. Moreover, it is evident that many alternatives, modifications, and variations will be apparent to those skilled in the art. It is to be understood that other embodiments may be utilized and structural changes may be made without departing from the scope of the embodiments. Accordingly, this disclosure is intended to embrace all such alternatives, modifications, and variations that fall within the spirit and scope of the appended claims and their equivalents.

We claim:

1. A system configured to identify the dominant nostril, comprising:
at least one inward-facing head-mounted thermal camera (CAM) configured to take thermal measurements of first and second regions below the right and left nostrils ($TH_{ROf1}$ and $TH_{ROf2}$, respectively); wherein the at least one CAM does not occlude any of the user's mouth and nostrils; and
a computer configured to identify the dominant nostril based on $TH_{ROf1}$ and $TH_{ROf2}$.

2. The system of claim 1, wherein each CAM from among the at least one CAM weighs below 10 g, comprises multiple sensing elements, and is physically coupled to a frame configured to be worn on the user's head; wherein the frame is configured to hold each CAM less than 15 cm from the user's face and above the user's upper lip.

3. The system of claim 1, further comprising a frame configured to be worn on the user's head; wherein the at least one CAM comprises first and second inward-facing head-mounted thermal cameras (CAM1 and CAM2, respectively) configured to take $TH_{ROf1}$ and $TH_{ROf2}$, respectively; wherein the frame is configured to hold CAM1 and CAM2 less than 15 cm from the user's face; and wherein CAM1 is physically coupled to the right half of the frame and captures the exhale stream from the right nostril better than it captures the exhale stream from the left nostril, and CAM2 is physically coupled to the left half of the frame and captures the exhale stream from the left nostril better than it captures the exhale stream from the right nostril.

4. The system of claim 1, wherein the computer is further configured to learn typical sequence of switching between the dominant nostrils based on previous measurements of the user taken over more than a week, and to issue an alert upon detecting an irregularity in the sequence of switching between the dominant nostrils.

5. The system of claim 1, wherein the computer is further configured to identify balanced breathing when breaths through the right and the left nostrils are equal, and to notify the user accordingly.

6. The system of claim 1, wherein the computer is further configured to monitor nostril dominance over a certain period, and issue an alert when at least one of the following occurs: (i) a ratio between the total times of the right and left nostril dominance during the certain period reaches a threshold, (ii) an average time to switch from right to left nostril dominance reaches a threshold, and (iii) an average time to switch from left to right nostril dominance reaches a threshold.

7. The system of claim 1, wherein the computer is further configured to detect that the user is experiencing an asthma attack or has a headache, and to command a user interface to update the user about the dominant nostril and to suggest the user to switch the dominant nostril.

8. The system of claim 1, wherein the computer is further configured to provide, via a user interface, biofeedback that helps the user to achieve a required breathing pattern.

9. The system of claim 1, wherein $TH_{ROf1}$ and $TH_{ROf2}$ are indicative of length of the exhale stream, and the computer is further configured to calculate a level of excitement of the user based on the length of the exhale stream.

10. The system of claim 1, wherein the computer is further configured to identify a shape of the exhale stream (SHAPE) based on $TH_{ROf1}$ and $TH_{ROf2}$, and to differentiate between at least first and second shapes of the exhale stream (SHAPEs).

11. The system of claim 10, wherein the first SHAPE is identified based on a first set of $TH_{ROf1}$ and $TH_{ROf2}$ taken during multiple exhales over a first duration longer than a minute, the second SHAPE is identified based on a second set of $TH_{ROf1}$ and $TH_{ROf2}$ taken during multiple exhales over a second duration longer than a minute, and the first duration precedes the second duration.

12. The system of claim 10, wherein the computer is further configured to learn a sequence of typical changes between different SHAPEs based on previous measurements of the user taken over more than a week, and to issue an alert upon detecting an irregularity in a sequence of changes between the different SHAPEs.

13. The system of claim 10, wherein the computer is further configured to suggest the user to eat a first type of food responsive to identifying the first SHAPE, and suggest the user to eat a second type of food responsive to identifying the second SHAPE.

14. The system of claim 13, wherein the computer is further configured to receive data about types of foods consumed by the user, store the data in a memory, and find correlations between the SHAPEs and the types of foods.

15. The system of claim 10, wherein the computer is further configured to prioritize activities for the user based on the identified SHAPE, such that a first activity is prioritized over a second activity responsive to identifying the first SHAPE, and the second activity is prioritized over the first activity responsive to identifying the second SHAPE.

16. The system of claim 10, wherein the computer is further configured to receive an indication of the user's breathing rate, and to: (i) suggest to the user, via a user interface, to perform a first activity in response to detecting that the breathing rate reached a threshold while identifying the first SHAPE, and (ii) suggest to the user to perform a second activity, which is different from the first activity, in response to detecting that the breathing rate reached the threshold while identifying the second SHAPE.

17. The system of claim 10, wherein the computer is further configured to receive an indication of the user's breathing rate, and to: (i) alert the user, via a user interface, in response to detecting that the breathing rate reached a threshold while identifying the first SHAPE, and (ii) not alert the user in response to detecting that the breathing rate reached the threshold while identifying the second SHAPE.

18. The system of claim 10, wherein the computer is configured to identify the SHAPE by comparing $TH_{ROI1}$ and $TH_{ROI2}$ to one or more reference patterns that were generated based on previous $TH_{ROI1}$ and $TH_{ROI2}$ of the user taken on different days.

19. The system of claim 10, wherein identifying the SHAPE comprises: generating feature values based on $TH_{ROI1}$ and $TH_{ROI2}$, and utilizing a model to classify $TH_{ROI1}$ and $TH_{ROI2}$ to a class corresponding to the first shape or the second shape, based on the feature values; and wherein the model is trained based on previous $TH_{ROI1}$ and $TH_{ROI2}$ of the user taken during different days.

20. The system of claim 10, wherein the first and second SHAPEs are indicative of at least one of the following: two of the five great elements according to Vedas, two different emotional states of the user, two different moods of the user, two different energetic levels of the user, and a healthy state of the user versus an illness state of the user.

* * * * *